(12) United States Patent
Linder et al.

(10) Patent No.: US 10,842,747 B2
(45) Date of Patent: *Nov. 24, 2020

(54) NANO-SIZED PARTICLES COMPRISING MULTI-HEADED AMPHIPHILES FOR TARGETED DRUG DELIVERY

(71) Applicant: Ben-Gurion University of the Negev Research and Development Authority, Beer-Sheva (IL)

(72) Inventors: Charles Linder, Rehovot (IL); Sarina Grinberg, Meitar (IL); Eliahu Heldman, Rehovot (IL)

(73) Assignee: Ben-Gurion University of Negev R & D, Beer-Sheva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/590,862

(22) Filed: May 9, 2017

(65) Prior Publication Data

US 2017/0367980 A1 Dec. 28, 2017

Related U.S. Application Data

(63) Continuation of application No. 13/318,869, filed on Mar. 15, 2012, now Pat. No. 9,642,803, which is a continuation of application No. PCT/IL2010/000359, filed on May 4, 2010.

(60) Provisional application No. 61/213,065, filed on May 4, 2009.

(51) Int. Cl.
| | |
|---|---|
| *A61K 9/127* | (2006.01) |
| *A61K 9/51* | (2006.01) |
| *A61K 9/00* | (2006.01) |
| *C07C 229/22* | (2006.01) |

(52) U.S. Cl.
CPC .......... *A61K 9/1272* (2013.01); *A61K 9/0019* (2013.01); *A61K 9/127* (2013.01); *A61K 9/51* (2013.01); *C07C 229/22* (2013.01)

(58) Field of Classification Search
None
See application file for complete search history.

(56) References Cited

U.S. PATENT DOCUMENTS

| | | | | |
|---|---|---|---|---|
| 4,801,614 | A * | 1/1989 | Plotnikoff | A61K 38/33 514/18.5 |
| 5,049,395 | A | 9/1991 | Chang | |
| 2006/0039962 | A1 | 2/2006 | Heldman et al. | |
| 2007/0185042 | A1 | 8/2007 | Tsai et al. | |

FOREIGN PATENT DOCUMENTS

| | | |
|---|---|---|
| WO | 03/047499 A2 | 6/2003 |
| WO | 2009/049089 A1 | 4/2009 |
| WO | 2009/056955 A1 | 5/2009 |

OTHER PUBLICATIONS

European Patent Examination Report issued for corresponding European Patent Application No. 10 725 503.6 dated Jul. 19, 2016.
Wiesman et al., "Novel cationic cesicle platform derived from vernonia oil for efficient delivery of DNA through plant cuticle membranes", Journal of Biotechnology, ElsevierScience Publishers, Amsterdam, NL LNKD- DOI:10.1016/J.JBIOTEC.2007.01.040, vol. 130, No. 1, pp. 85-94, Apr. 26, 2007.
Australian Patent Examination Report No. 1 issued for corresponding Austrailian Patent Application No. 2010245629 dated Sep. 22, 2015.
Grinberg et al., "Synthesis of novel cationic bolaamphiphiles from vemonia oil and their aggregated structures", 2008, Chemistry and Physics of Lipids, pp. 85-97.
Non-Final Office Action issued for U.S. Appl. No. 13/318,869 dated Nov. 5, 2013.
Extended European search issued for corresponding European Patent Application No. 18191342.7, dated Jul. 12, 2019.
Grinberg et al., "Asymmetric bolaamphiphiles from vemonia oil designed for drug delivery", European Journal of Lipid Science and Technology, vol. 112, No. 1, Jan. 2010, pp. 137-151.
Popov et al., "Cationic vesicles from novel bolaamphiphilic compounds", Journal of Liposome Research, vol. 20, No. 2, Jun. 2010, pp. 147-159.

\* cited by examiner

*Primary Examiner* — Michael G. Hartley
*Assistant Examiner* — Lance W Rider
(74) *Attorney, Agent, or Firm* — Myers Wolin, LLC

(57) ABSTRACT

Nano-sized particles are provided comprising at least one multi-headed amphiphilic compound, in which at least one headgroup of said multi-headed amphiphilic compound is selectively cleavable or contains a selectively cleavable group, and at least one biologically active agent, which is both encapsulated within the nano-particle and non-covalently associated thereto.

35 Claims, 7 Drawing Sheets

NANO-SIZED PARTICLES COMPRISING MULTI-HEADED AMPHIPHILES FOR TARGETED DRUG DELIVERY

This application is a continuation of U.S. patent application Ser. No. 13/318,869, filed on Nov. 4, 2011, which is a continuation of International Application No. PCT/IL2010/000359 filed May 4, 2010, which in turn claims priority from U.S. Provisional Application Ser. No. 61/213,065, filed May 4, 2009, the contents of each of which are hereby incorporated by reference herein.

FIELD OF THE INVENTION

The present invention is in the field of drug delivery and, more particularly, relates to nano-sized particles comprising at least one multi-headed amphiphilic compound and a biologically active agent.

BACKGROUND ART

The use of proteins, peptides and polynucleotides such as DNA and RNA (including small interference (si) RNA) in therapy or in preventive medicine is limited because they are generally impermeable through various biological barriers (e.g., blood-brain barrier (BBB) and membrane barriers of the circulatory system, intestinal track, skin and lungs) and sensitive to proteolytic enzymes, thus not surviving the passage from the site of administration to the site of action. These limitations result in poor pharmacokinetics (PK), preventing or limiting their use in the treatment of neurological diseases and in diseases in other organs of the body.

Many drugs and biologically active molecules cannot penetrate the BBB and thus require direct administration into the CNS tissue or the cerebral spinal fluid (CSF) in order to achieve a biological or therapeutic effect. Even direct administration into a particular CNS site is often limited due to poor diffusion of the active agent because of local absorption/adsorption into the CNS matrix. Present modalities for drug delivery through the BBB entail disruption of the BBB by, for example, osmotic means (hyperosmotic solutions) or biochemical means (e.g., use of vasoactive substances such as. bradykinin), processes with serious side effects.

In order to fulfill the therapeutic potential of peptides, proteins and nucleotides and other agents with poor PK, a non invasive delivery method is required that will distribute the agent at the desired area of the target site (e.g., a wide area of an organ such as the brain), will have good blood circulatory lifetime for the delivery platform, will penetrate through biological barriers and will have a selective disruption mechanism.

Small interference RNAs (siRNAs) are an example for polynucleotides which would have a highly promising therapeutic potential if only their PK could be improved. RNA interference is a powerful strategy to inhibit gene expression through specific mRNA degradation mediated by siRNAs. However, in vivo application of siRNAs is severely limited by their instability and poor delivery to target cells and target tissues. siRNAs could be an alternative therapy of glioblastoma, a brain tumor highly resistant to chemotherapy and radiotherapy. Gene silencing is a promising approach for inhibiting the proliferation of this type of tumor and several target genes may be considered for this therapeutic strategy, such as epidermal growth factor receptor variant III, which is expressed in 40-50% of gliomas, and the phosphoinositide 3-kinase (PI3K)/Akt pathway, which plays a crucial role in medulloblastoma biology. Targeting of such oncogenic pathways can be achieved by gene silencing with RNA interference. However, before RNA interference can be exploited for brain tumor therapy, several obstacles have to be overcome, such as the instability of siRNAs in the blood stream and their impermeability through the BBB.

An efficient delivery system for proteins, peptides, polynucleotides and other biologically active agents should protect the agents while they are being transported, allow them to pass intact through biological barriers such as the BBB, and target them to the site of action by a mechanism that releases them specifically at that site. In order to achieve such performance, such a delivery system should preferably comprise nano-sized drug carriers which are stable in biological fluids, penetrate intact various biological membranes and have a selective disruption mechanism. In addition, such a carrier should be able to encapsulate significant amounts of the active agent whereby many molecules per vesicle or carrier are targeted to a particular site or organ. There are, however, no currently efficient delivery systems wherein all these necessary properties are combined within one delivery system.

Complexation of the anionic carboxyfluorescein (CF) with single headed amphiphiles of opposite charge in cationic vesicles, formed by mixing single-tailed cationic and anionic surfactants has been reported (Danoff et al. 2007). Wang et al. (2006) disclose complexation of the anionic CF with bilayered vesicles formed from cetyl trimethylammonium tosylate (CTAT) and sodium dodecylbenzenesulfonate (SDBS). The CTAT-rich (cationic) vesicles were shown to capture the CF with high efficiency (22%). The ability of these vesicles to capture and hold dyes is very high (>20%) when the excess charge of the vesicle bilayer is opposite to that of the solute (i.e., CTAT-rich vesicles capture anionic solutes very efficiently, whereas SDBS-rich vesicles efficiently capture cationic solutes).

U.S. Pat. No. 6,358,523 discloses macromolecule-lipid complexes, macromolecule targeting and delivery to various biological systems.

WO 02/055011 and WO 03/047499, both of the same applicant, disclose amphiphilic derivatives composed of at least one fatty acid chain derived from natural vegetable oils such as vemonia oil, lesquerella oil and castor oil, in which functional groups such as epoxy, hydroxy and double bonds were modified into polar and ionic headgroups. The amphiphiles of WO 02/055011 and WO 03/047499 comprise one or more ionic or polar headgroups and at least one hydrogen-bonding group located either within said headgroup and/or in close proximity thereto. These amphiphiles are capable of spontaneously forming vesicles and micelles owing to their polar and ionic headgroups.

WO 03/047499 discloses bolaamphiphiles (vesicle-forming amphiphilic compounds bearing two headgroups), having at least one headgroup containing a selectively cleavable group or moiety such as a residue of a choline or phenylalanine derivative. The cleavable group or moiety is cleaved and the vesicles disrupt and release their load under selective conditions, which include change of chemical, physical or biological environment. These vesicles are preferably cleaved enzymatically in a biological environment such as the brain or the blood. The vesicles or liposomes made from these amphiphilic compounds are highly stable, beyond what is achievable with the lipids and surfactants used in the current state of the art, and suitable for delivery of a therapeutic substance or a diagnostic agent specifically to a target organ or tissue.

The prior art does not emphasize the benefits of using multi-headed amphiphiles for targeted delivery. Simultaneous complexation and encapsulation of small molecules and macromolecules such as peptides, proteins and nucleotides within vesicles of bolaamphiphiles or multi-headed amphiphiles bearing selectively cleavable groups, is not disclosed in the prior art either. However, it is the use of such multi-headed amphiphiles and particularly bolaamphiphiles that can achieve the desired combination.

SUMMARY OF INVENTION

In one aspect, the present invention relates to a nano-sized particle comprising at least one multi-headed amphiphilic compound, in which at least one headgroup of said multi-headed amphiphilic compound is selectively cleavable or contains a selectively cleavable group, and at least one biologically active agent, which is both encapsulated within the nano-particle and non-covalently associated thereto.

The nanoparticles of the invention are useful for delivery of the biologically active agent to a target organ or tissue.

Thus, in another aspect, the present invention relates to a pharmaceutical composition comprising nano-sized particles of the invention and a pharmaceutically acceptable carrier.

Depending on the biologically active agent comprised within the nanoparticles of the invention, the nanoparticles or the pharmaceutical composition comprising them can be used for treatment or diagnosis of diseases or disorders selected from: (i) diseases or disorders associated with the central nervous system (CNS), in particular neurological and/or neurodegenerative diseases or disorders such as Parkinson's disease, Alzheimer's disease or multiple sclerosis; (ii) cancer such as breast cancer and brain tumors; (iii) diabetes; (iv) immunodeficiency diseases; and (v) viral and bacterial infections.

DETAILED DESCRIPTION OF THE INVENTION

Figure 1:
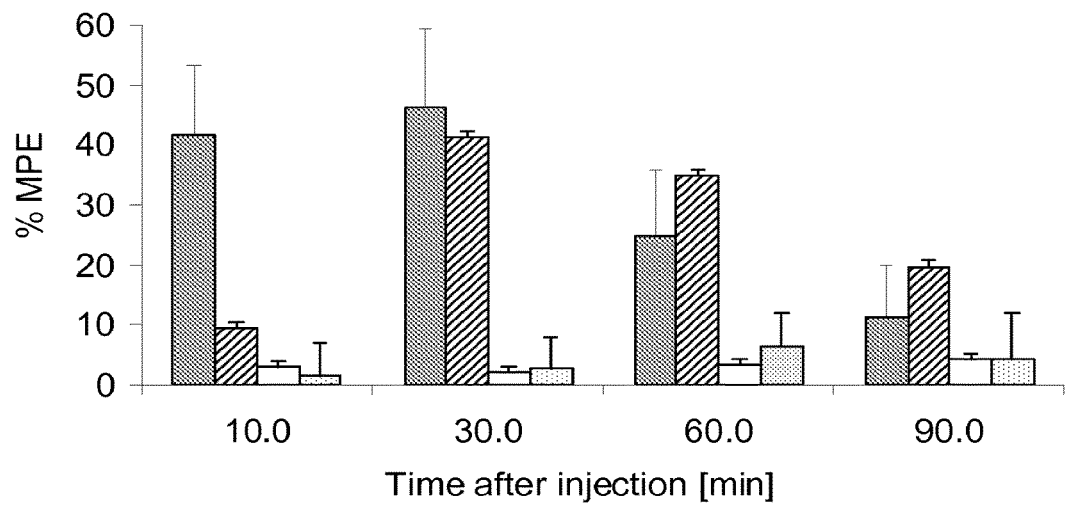
FIG. 1 is a graph showing the analgesic effect as percent of the maximal possible effect (MPE) in a hot plate test conducted on mice treated with morphine (5 mg/kg) (gray column), Derivative 4-nanoparticles loaded with 5 mg/kg leu-enkephaime (Hatched column), empty Derivative 4-nanoparticle 20 mg/kg (empty column), and free leu-enkephalin (20 mg/kg) (dotted column). The values are means±SEM of 5 mice.

It has been found by the present inventors that when multi-headed amphiphiles, particularly double-headed amphiphiles also termed "bolaamphiphiles", comprising cationic headgroups were mixed with marker molecules with opposite anionic carboxylic charge (e.g., carboxyfluorescein (CF)), vesicles were formed with a very high encapsulation efficiency than would be expected from vesicle size: 10 to 30% instead of 5%. Good encapsulation efficiency for a given active agent was obtained when bolaamphiphiles such as those disclosed in WO 03/047499 of the same inventors, incorporated herein by reference as if fully described herein, were used for the preparation of nano-sized vesicles in the presence of active agent solutes selected from peptides, proteins, polynucleotides or non-polymeric molecules. Surprisingly efficient encapsulation occurred when the net ionic charges on the amphiphiles' head group and on the encapsulated molecule were opposite (e.g., cationic versus anionic). The unexpected high loading efficiency could not be attributed solely to encapsulation of the peptides, proteins, polynucleotides or non-polymeric molecules within the vesicles' core, and other kind of interactions that associated the molecules to the vesicles had to be considered.

In other experiments performed by the inventors, when molecules with anionic carboxylic groups such as cholesterol hemisuccinate were mixed with cationic bolaamphiphiles, stable vesicles were formed wherein cholesterol hemisuccinate was shown to be taken up in the outer surface of the vesicles. At the same time, the use of cholesterol hemisuccinate reduced the percentage encapsulation of CF, indicating that CF may form a counter ion to the bolaamphiphile headgroups on the inside and outside surfaces of the vesicular membrane. The fact that the encapsulation efficiency of CF was still relatively high in the presence of cholesterol hemisuccinate suggests that CF may be associated with the vesicles in some other manners besides being encapsulated within the vesicle core.

It is assumed that non-covalent interactions such as ionic interactions between the solute and the oppositely charged headgroups result in attachment of solutes onto the vesicles' inner and outer surface. In addition, it is believed that some solute molecules may be embedded or immersed in the vesicular membrane as well as within the core. Thus, the delivery platform obtained is probably a nano-sized particle comprising amphiphiles and active agent molecules, which are associated with the amphiphiles by way of encapsulation within vesicles formed from the amphiphiles, ionic interactions of oppositely charged groups and/or other non-covalent interactions, as well as immersion or incorporation within the vesicular matrix.

It was further found by the present inventors that for properly chosen headgroups and amphiphiles, nano-sized particles were obtained which possessed excellent targeting delivery properties after i.v. and oral administration. Proper headgroups were headgroups that could serve as substrates for enzymes found in significant concentrations at the target site, and could enhance penetration through different biological barriers.

The present inventors further found that use of amphiphiles with cationic headgroups such as choline ester headgroups, improved penetration of the vesicles made therefrom through biological barriers. Penetration of nanoparticles via the BBB was shown to be accelerated by providing them with cationic surface groups.

It is well known, however, that cationic particles are cleared from the blood circulation within a period of less than one hour. The present inventors have surprisingly found that particles comprising nano-sized vesicles (as a non limiting example ~80 nm) having a monolayer membrane significantly slowed down the rapid particles clearance.

The present inventors also found that attaching certain additives such as chitosan, chitosan derivatives and polyamines to the nanoparticles surface enhanced penetration through the intestinal tract as well as other biological barriers. These additives proved particularly useful in oral dosage forms for delivery to the CNS or other organs such as the heart, muscles or lungs.

Thus, in one aspect, the present invention provides a nano-sized particle comprising at least one multi-headed amphiphilic compound, in which at least one headgroup of said multi-headed amphiphilic compound is selectively cleavable or contains a selectively cleavable group, and at least one biologically active agent, which is both encapsulated within the nano-sized particle and non-covalently associated thereto.

Non-covalent interactions, which may exists include, but are not limited to, ionic and polar interactions, hydrogen bonding, electrostatic forces, hydrophobic interactions and Van der Waals forces.

In particular embodiments, the biologically active agent is associated to the nano-sized particle via ionic interactions.

In other particular embodiments, the biologically active agent forms a salt complex with the nanoparticle. In a more particular embodiment the active agent is associated with the nanoparticle via ionic interactions between the multi-headed amphiphilic compound and oppositely charged groups of the active agent itself.

The nano-sized particle of the invention (also termed herein "nanoparticle") may comprise molecules of non-encapsulated active agents that are embedded or immersed or incorporated in its matrix. Thus, in certain embodiments, the nano-sized particle comprises an amphiphilic compound and a biologically active agent encapsulated therein, non-covalently associated thereto and, in addition, incorporated or embedded therein.

The nano-sized particles most often are in the form of vesicles or liposomes formed from the multi-headed amphiphiles having a core (which may be liquid or solid or gel) and a membrane surrounding the core, made at least in part from these amphiphiles.

In particular embodiments, the nano-vesicles have an outer diameter of less than 500 nm, preferably less than 150 nm. Such vesicles or liposomes may encapsulate within their core the active agent, which in particular embodiments is selected from peptides, proteins, nucleotides and or non-polymeric agents. The active agent in most cases is also associated via one or more non-covalent interactions to the vesicular membrane on the outer surface and/or the inner surface, optionally as pendant decorating the outer or inner surface, and may further be incorporated into the membrane surrounding the core. Particularly, biologically active peptides, proteins, nucleotides or non-polymeric agents that have a net electric charge, may associate ionically with oppositely charged headgroups on the vesicle surface and/or form salt complexes therewith.

Nano-sized particles wherein the biologically active molecules are complexed with the vesicles are also referred to herein as "vesicular complexes".

Complexation of multi-headed amphiphiles with the active agent may be obtained by way of forming salt complexes of the ionic headgroups and the active agents. Formation of such salt complexes may influence the final size of the nanoparticles and their morphology. Such complexation increases the effectiveness of the encapsulation process and imparts surface properties to the nanoparticles that would influence their pharmacokinetics, bioavailability and targeted drug delivery properties.

The hydrophobic moieties or other groups of the active agent may also interact by secondary forces with the different components of the multi headed amphiphiles, for example by hydrophobic-hydrophobic interactions.

The multi-headed amphiphilic compound, herein sometimes also termed "amphiphile" or "amphipathic compound", constitutes the infrastructure of the nano-sized delivery system of the invention, and its structure and chemical properties determines to a great extent the stability and efficiency of delivery.

In a particular embodiment, the multi-headed amphiphiles is a bolaamphiphile.

As used herein, the term "headgroup" is interpreted in the context of an amphiphilic compound and refers to a polar or ionic group attached to the aliphatic chain of the amphiphile, either directly or indirectly (e.g., via a linker), and promotes or supports spontaneous self-aggregation of the amphiphiles in aqueous media.

When amphiphilic compounds are mixed with water, the polar or charged regions and the non-polar regions (aliphatic chains) of the amphiphiles experience conflicting tendencies; the polar or charged hydrophilic regions interact favorably with the solvent and tend to dissolve, but the non-polar, hydrophobic regions have the opposite tendency, to avoid contact with the water. The non-polar regions of the amphiphiles cluster together to present the smallest hydrophobic area to the solvent, and the polar regions are arranged to maximize their interactions with the aqueous solvent.

Ionic groups in amphiphiles often function as headgroups, however not all polar groups are headgroups. A polar group is a head group when it supports (spontaneous) self-aggregation of the amphiphiles. This occurs when the polar group has sufficient water solubility or attractive powers. Thus, amides (—CO—NH—), epoxies, ethers (e.g., ethylene oxide) and even single hydroxyl groups are not sufficiently water attracting or solubilizing to be considered headgroups. Sugars, however, with multiple hydroxyl groups and polyethylene glycols or polyethylene oxides with multiple ethylene oxide groups, are highly water attracting with a large degree of water of hydration, and function as headgroups. In certain embodiments of the invention, the nanoparticles comprise amphiphilic compounds that have polar headgroups.

The amphiphiles used according to the invention have a low critical aggregation concentration (CAC), preferably of less than $10^{-4}$, more preferably less than $10^{-5}$, most preferably less than $10^{-6}$ moles.

For convenience, the term "selectively cleavable head group" shall be used throughout the description to denote both a headgroup that is cleaved under selective conditions and a headgroup containing removable group or moiety that is cleaved under selective conditions, wherein said selective conditions include change of chemical, physical or biological environment such as, but not limited to, change of pH or temperature, oxidative or reducing conditions, and/or enzymatic conditions. The term "removable group" denotes a specific functional group within the selectively cleavable group or moiety that is removed from the molecule when the cleavage occurs, often together with the linker that connects it to the hydrophobic chain.

In certain embodiments of the invention, the selectively cleavable headgroup is cleaved enzymatically in a biological environment, particularly in the brain or blood, by degradatives enzymes such as hydrolases, esterases, phosphatases, oxidases, decarboxylases, deaminases and isomerases, some of which are restricted to the brain or exist also in the brain and in the periphery. Examples of such enzymes include, but are not limited to, cholinesterases (ChE), acetylcholine esterase (AChE) and aromatic L-amino acid decarboxylase (AADC).

Preferred headgroups according to the invention are those which serve as substrates to enzymes at a target site of a biological environment, e.g. hydrolytic enzymes, enhance transport of the nanoparticles through biological barriers and/or stabilize a vesicular structure of the nanoparticles. At least one of these preferred headgroups is a selectively cleavable headgroup.

Non-limiting examples of such headgroups include: (i) choline or thiocholine, O-alkyl, N-alkyl or ester derivatives thereof. O-alkyl derivatives of choline or thiocholine are derivatives in which the H atom of the hydroxy group is replaced with a straight or branched C1-C20 alkyl and include methyl, ethyl, propyl, butyryl, pentyl, hexyl and octyl choline/thiocholine. N-alkyl derivatives of choline and thiocholine are derivatives in which one, two or three of the methyl groups attached to the quaternary nitrogen atom are replaced by a straight or branched C1-C20 alkyl. Choline and thiocholine esters include, for example, acetylcholine, acetylthiocholine, propionyl choline/thiocholine, butanoyl choline/thiocholine, pentanoyl choline/thiocholine, hexanoyl choline/thiocholine, octyanoyl choline/thiocholine. Such choline and thiocholine derivatives may be cleaved by choline or acetylcholine esterases found in the brain; (ii) non-aromatic amino acids with functional side chains such as glutamic acid, aspartic acids, lysine or cysteine, or an aromatic amino acid such as tyrosine, tryptophan, phenylalanine and derivatives thereof such as levodopa (3,4-dihydroxy-phenylalanine) and p-aminophenylalanine. The carboxyl group of the aromatic amino acids is selectively cleaved by aromatic AADCs found in brain cells; (iii) a peptide or a peptide derivative that is specifically cleaved by an enzyme at a diseased site. Non-limiting examples include enkephalin which is cleaved by enkephalinase primarily in the brain; N-acetyl-ala-ala, which is cleaved by elastase that is overexpressed in certain types of cancer and aneurysms; a peptide that constitutes a domain recognized by beta and gamma secretases (which are over expressed in the brain of Alzheimer's disease patients), or a peptide that is recognized by stromelysins. Nanoparticles comprising these peptides will release their content in inflammatory sites; (iv) saccharides such as glucose, mannose and ascorbic acid; (v) other compounds such as nicotine, cytosine, lobeline, polyethylene glycol, or cannabinoids.

In certain embodiments, one or more of the headgroups of the multi-headed amphiphiles are amphoteric and have a pI point. Examples of such headgroups are amino acids, which may have a net anionic charge at a pH above their pI point or a net cationic charge at a pH below their pI point. The pH during the formation of the nanoparticles can be adjusted such that the headgroups on the amphiphiles will have an opposite charge to that of the active agent. In some cases, the pH may be changed after nanoparticle formation in order to facilitate complexation with the active agent.

In certain embodiments, the active agents e.g., proteins and peptides may have both fixed anionic and cationic groups or amphoteric groups, and complexation with charged headgroups of the amphiphiles is facilitated as a function of the pH in which the nanoparticles are formed: at a pH below the pI point of the peptides or proteins, they may have a net cationic charge and can form complexes with amphiphiles having a net anionic charge at this pH, whereas at a pH above the pI point of the peptides or proteins they may have a net anionic charge and form complexes with amphiphiles having a net cationic charge.

In certain embodiments, the active agent molecules which bear charged groups are encapsulated within the vesicular core at a certain pH where they cannot complex with the headgroups of the amphiphiles since they both have the same ionic charge. After vesicle formation and encapsulation, the pH is changed such that residual non-encapsulated active agent changes its net charge and forms ionic complexes with the headgroups. Such complexation strengthen the nanoparticle structure.

In certain embodiments, when the net charges of the active agent and the amphiphiles are opposite, the active agent is predominantly complexed with ionic groups on the inner and outer surface of the vesicles while a minor amount is within the core. In certain additional embodiments, when the headgroups of the amphiphiles are partially or all saturated with active agent molecules or with non-active additives that are added to the nanoparticle, a larger fraction of the active molecules is also encapsulated within the vesicle core. Non-active additives, which are added mostly in order to enhance stability, can form counter salt moieties to the charged headgroups. An example of such an additive is cholesterol hemmisuccinate in which the hemmisuccinate forms a counter salt moiety to cationic headgroups such as acetyl choline.

In certain embodiments, the biological active agent may facilitate stable vesicles structures by being, at least in part, incorporated or embedded into the membrane of the vesicles. In these embodiments, the active agent has amphiphilic properties and is a molecule comprising an ionic group(s) and a predominant hydrophobic structure.

The structure of the nano-sized particle of the inventions is determined not only by the chemical composition of its components but also by the chemical conditions in which it was formed such as ionic strength, pH, buffers and concentrations of the various components. The nanoparticle structure may also be a function of the method by which it was prepared, which for example can be film hydration followed by sonication (FHS) or film hydration followed by extrusion (FHE), or solvent (e.g., ethanol) injection, optionally followed by sonication and/or extrusion.

Substantial properties of the nanoparticles of the invention include: (i) small, stable size of less than 200 nm, preferably less than 100 nm diameter, mainly due to optimized packing of the amphiphile components; (ii) protection of the encapsulated material from enzymatic and otherwise chemical modifications; (iii) good blood circulatory life time in order to reach target sites; (iv) penetration through biological barriers; and (v) a selective disruption mechanism at the target site or organ.

Nano-sized particles encompassed by the present invention may have configurations or aggregate structures other than spherical vesicular complexes. For example, a peptide, protein or polynucleotide may be surrounded by a sheet of amphiphiles, preferably bolaamphiphiles, such that headgroups of the bolaamphiphiles and counter charged groups on the peptide interact. This arrangement can change the hydrophobic/hydrophilic structure of a biologically active peptide or protein.

A spherical or a particle approaching a spherical shape is a preferred shape for targeted release application of active molecules, particularly for injectable formulations and oral dosage forms, which enter the blood circulatory system. Other configurations have other applications such as implants of anti cancer drugs at tumor sites for slow controlled release or anti microbial activity in organs like the heart or lungs.

Bolaamphiphiles are the preferred amphiphiles for the purpose of the present invention, particularly since they form monolayer vesicles. Monolayer vesicles are advantageous since they are far more stable in a biological system due to substantially reduced lipid exchange with the cell membrane, as compared to bilayer and multilayer vesicles and liposomes, let alone vesicles and liposomes comprising phospholipids. Lipid exchange is crucial for intact penetration through biological barriers and increased blood circulatory lifetime. Minimal lipid exchange of the vesicular membrane with cellular membrane increases stability.

Though highly stable structures, monolayer vesicles made from bolaamphiphiles bearing the proper selectively cleavable headgroups can nevertheless be disrupted at a given site, which contains enzymes in sufficient concentrations for facilitating hydrolysis. Selective disruption mechanisms are more easily obtained with monolayer membranes compared to bilayer membranes as bolaamphiphiles readily change their self aggregate structures upon relative small changes in their molecular structures. Thus, removing the headgroups on monolayer vesicles made from bolaamphiphiles may more readily disrupt the vesicular structure and release the encapsulated material at the site of hydrolysis.

In particular embodiments of the invention at least one hydrogen-bonding group such as, but not limited to, —OH, —SH, —NH—, —N$^+$H$_2$—, —NH$_2$, —N$^+$H$_3$, —NH—CO—, —O—CO—NH—, —NH—CO—NH—, —C=NOH, —C(NH$_2$)=NOH, —C(NH$_2$)=NO— and —CO—NH$_2$, is found either within the selectively cleavable headgroup or within the headgroup containing the selectively cleavable group or moiety and/or in close proximity thereto, thus imparting more stability and other features to the vesicles made from such amphiphilic compounds. By "close proximity" it is meant herein that the hydrogen-bonding group is located at the atom vicinal to the atom of the aliphatic chain to which the headgroup is bound and/or at a distance of up to 6 atoms in the aliphatic chain. Bolaamphiphiles comprising the aforementioned hydrogen bonding groups suitable for the purpose of the invention are those disclosed in WO 30/0474499 incorporated herein by reference as if fully disclosed herein.

In particular embodiments, the nanoparticles of the invention comprise at least one bolaamphiphile compounds having the formula I:

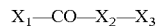

$$X_1\text{—CO—}X_2\text{—}X_3 \qquad [\text{I}]$$

wherein $X_1$ is -$Q_1$-$R_0$, wherein $Q_1$ is —NH—, —O—, —S—, or —O—PO(OH)—O—;

$R_0$ is —$X_4$—$X_5$—$X_6$ or —(CH$_2$)r'—$X_7$;

$X_2$ and $X_5$, the same or different, each is an alkylene chain of at least 5 carbon atoms;

$X_3$ and $X_6$, the same or different, each is an aliphatic chain of at least 5 and at most 18 carbon atoms optionally carrying at least one double bond, said aliphatic chain being substituted by at least one polar, ionic and/or epoxy groups and/or by at least one moiety containing at least one polar, ionic and/or epoxy groups, said at least one polar, ionic and/or epoxy groups and at least one moiety containing at least one polar, ionic and/or epoxy groups being, in relation to their substitutions, in any combination of 1-2, 1-2-3, 1-2-3-4, 1-2-4-5, 1-2-3-4-5, 1-2-4, 1-2-5, 1-3-4, 1-3, 1-5, 1-4, or 1-2-6 positions of the chain, the position 1 being arbitrarily assigned to the substitution most remote from the CO group;

$X_4$ is a spacer group consisting of a linear or branched aliphatic chain of up to 16 carbon atoms, optionally interrupted by $Q_2$ or by —CO-$Q_2$-, wherein $Q_2$ is —NH—, —O—, —S—, or —O—PO(OH)—O—, and optionally containing at least one polar and/or ionic group or at least one moiety containing at least one polar and/or ionic group;

$X_7$ is hydrogen, $C_6$-$C_{14}$ aryl, preferably phenyl, or a heterocyclic radical;

r' is an integer from o to 12; and wherein at least one polar and/or ionic group and/or at least one moiety containing at least one polar and/or ionic group of $X_3$, $X_4$ and/or $X_6$ is a headgroup, and wherein at least one of said headgroup is a selectively cleavable headgroup or a headgroup containing a selectively cleavable group or moiety and, optionally, at least one hydrogen-bonding group is located within and/or in close proximity to said selectively cleavable headgroup or headgroup containing a selectively cleavable group or moiety.

In other particular embodiments, the nanoparticles of the invention comprise amphiphilic compounds having the formula II:

$$X_6\text{-}X_5\text{-}X_4\text{-CO-}Q_1\text{-}X_2\text{-}X_3 \qquad [\text{II}]$$

wherein $Q_1$ is —NH—, —N(CH$_3$)$_{1\ to\ 2}$—, —O—, —S—, or —O—PO(OH)—O—;

$X_4$ is a spacer group consisting of a linear or branched aliphatic chain of up to 16 atoms, optionally interrupted by —CO-Q$_2$-, wherein Q$_2$ is —NH—, —N(CH$_3$)$_{1\ to\ 2}$—, —O—, —S—, or —O—PO(OH)—O—, and optionally containing at least one polar and/or ionic group or at least one moiety containing at least one polar and/or ionic group;

$X_2$ and $X_5$, the same or different, each is an alkylene chain of at least 5 carbon atoms;

$X_3$ and $X_6$, the same or different, each is an aliphatic chain of at least 5 and at most 18 carbon atoms optionally carrying at least one double bond, said aliphatic chain being substituted by at least one polar, ionic and/or epoxy groups and/or by at least one moiety containing at least one polar, ionic and/or epoxy groups, said at least one polar, ionic and/or epoxy groups and at least one moiety containing at least one polar, ionic and/or epoxy groups being, in relation to their substitutions, in any combination of 1-2, 1-2-3, 1-2-3-4, 1-2-4-5, 1-2-3-4-5, 1-2-4, 1-2-5, 1-3-4, 1-3, 1-5, 1-4, or 1-2-6 positions of the chain, the position 1 being arbitrarily assigned to the substitution most remote from the CO group; and wherein at least one polar and/or ionic group and/or at least one moiety containing at least one polar and/or ionic group of X3, X4 and/or X6 is a headgroup, and wherein at least one of said headgroup is a selectively cleavable headgroup or a headgroup containing a selectively cleavable group or moiety and, optionally, at least one hydrogen-bonding group is located within and/or in close proximity to said selectively cleavable headgroup or headgroup containing a selectively cleavable group or moiety.

In one embodiment, the bolaamphiphiles of the formula I or II are composed of two fatty acid chains, formed by the —X$_2$—X$_3$ and —X$_5$—X$_6$ groups, each comprising a selectively cleavable polar or ionic headgroup or a polar or ionic headgroup containing a selectively cleavable group or moiety. In certain embodiments, at least one of the fatty acid chains contains a ionic or polar hydrogen-bonding group in close proximity to said headgroup and/or attached to a site within said headgroup. The two fatty acid chains are separated by a non-fatty acid midsection or spacer, for example a C$_2$-C$_{16}$ alkylene chain optionally interrupted by —O—, —S— or —NH—, and each fatty acid chain is bound to the midsection through an amide (a hydrogen-bonding group), ether, ester, thioester, and/or phosphoester bond.

In certain embodiments, said two fatty acid chains may be derived from the same or different fatty acids, selected from, but not limited to, vernolic acid (12,13-epoxyoctadec-9-enoic acid), lesquerolic acid (14-hydroxyeicosa-11-enoic acid), ricinoleic acid (12-hydroxyoctadec-9-enoic acid), partially or totally epoxidized linoleic, linolenic, and arachidonic acid, or from a derivative thereof obtained by reaction of the epoxy group and/or of a double bond and/or of a hydroxy group, or the aforementioned fatty chains may also be derived from a fatty acid selected from lauric, myristic, palmitic, stearic, arachidic, beherric, lignoceric, or undecylenic acid or from a derivative thereof. The sources of some epoxidized and hydroxylated fatty acids are vernonia oil, lesquerella oil, castor oil, and epoxidized soya and linseed oil.

In a particular embodiment, the nanoparticles of the invention comprise at least one bolaamphiphile of the formula Ia:

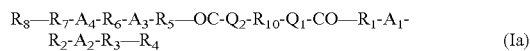

(Ia)

wherein:

$R_1$ and $R_5$, the same or different, each is —(CH$_2$)$_n$;

$A_1$ is selected from —(CH$_2$)$_{m+2}$—, —CH—CH—(CH$_2$)$_m$—, —CH—CH—CH(Y$_1$)—, —CH$_2$—CH$_2$—CH(Y$_1$)—, —CH$_2$—CH(Y$_1$)—(CH$_2$)$_m$—, —CH(Y$_1$)—CH$_2$—(CH$_2$)$_m$—, —CH(Y$_1$)—CH(Y$_2$)—(CH$_2$)$_m$—, wherein Y$_1$ and Y$_2$ each is halogen, —OH, —O—CO—(CH$_2$)$_m$—Y$_3$, —NH—CO—Y$_3$, —SH, —SR$_{11}$, —NH$_2$, or —N(R$_{11}$)(R$_{12}$), or Y$_1$ and Y$_2$ together with the carbon atoms to which they are attached form a 2,3-oxiranylene group; and Y$_3$ is halogen, —OH, —SH, —NH$_2$, or —N(R$_{11}$)(R$_{12}$);

$R_2$ and $R_6$, the same or different, each is C1-C4 alkylene, preferably methylene, optionally substituted by halogen, amino or hydroxy;

$A_2$ is selected from —CH(R$_{13}$)—, —CH$_2$—CH(R$_{13}$)—, —CH(R$_{13}$)—CH$_2$—, —CH(OH)—CH(R$_{13}$)—, —CH(R$_{13}$)—CH(OH)—, —CH(OH)—CH$_2$—CH(OH)—CH(R$_{13}$)—, —CH(OH)—CH$_2$—CH(R$_{13}$)—CH(OH)—, -G1-(C6-C14 arylene)-(CH$_2$)$_q$R$_{14}$, —N(CH$_3$)$_2$R$_{14}$, or —SR$_{14}$;

$R_3$ and $R_7$, the same or different, each is —(CH$_2$)$_o$—;

$R_4$ is H or CH$_3$, and wherein the total sum of carbon atoms in the R$_1$-A$_1$-R$_2$-A$_2$-R$_3$-R$_4$ chain is at most 23;

$Q_1$ is —NH—, —O—, —S—, or —O—PO(OH)—O—;
$Q_2$ is —NH—, —O—, —S—, or —O—PO(OH)—O—;

$R_{10}$ is a group selected from —(CH$_2$)$_p$—; —CH$_2$(CH$_3$)—(CH$_2$)$_p$—; —CH(CH$_3$)—(CH$_2$)$_p$—CH(CH$_3$)—; —(CH$_2$—CH$_2$—O—)$_p$—CH$_2$—CH$_2$—; —(CH$_2$—CH$_2$—S—)$_p$—CH$_2$—CH$_2$—; —(CH$_2$—CH$_2$—NH—)$_p$—CH$_2$—CH$_2$—; —C6-C14 arylene-; —(C6-C14 arylene)-R—(C6-C14 arylene)-, wherein R is C1-C4 alkylene, —C(CH$_3$)$_2$—, —O—, —S—, —NH— or —SO$_2$—;

$A_3$ is as defined for A$_1$, or is —(CH$_2$)$_m$, phenyl or —CH$_2$-phenyl, wherein the phenyl ring may be substituted by C1-C4 alkyl and/or by halogen;

$A_4$ is as defined for A$_2$, or is —(CH$_2$)$_m$;

$R_8$ is as defined for R$_4$;

$R_{11}$ and $R_{12}$, the same or different, each is C1-C18 alkyl optionally substituted by halogen; phenyl or —CH$_2$-phenyl, wherein the phenyl ring may be substituted by C1-C4-alkyl and/or by halogen, and wherein one of R$_{11}$ and R$_{12}$ may be H;

$R_{13}$ is -G1-(CH$_2$)$_m$R$_{14}$ or -G1-CO(CH$_2$)$_m$R$_{14}$;

G1 is —O—, —S—, —NR"—, —CH$_2$NR"—, —CH$_2$S— or —CH$_2$O—, —NH—CO—, —O—CO—NH—, —NH—CO—NH—, —C═NO—, —C(NH$_2$)═NO—, wherein R" is H or C1-C18 alkyl;

$R_{14}$ is either a selectively cleavable head group or a head group containing a selectively cleavable group or moiety, or is as defined for R$_{15}$ or for R$_{15}$ substituted by a selectively cleavable group or moiety;

$R_{15}$ is —NH$_2$; —NR$_{11}$R$_{12}$; —N$^+$R$_{11}$R$_{12}$R$_{16}$ wherein R$_{16}$ is as defined for R$_{11}$ and R$_{12}$; —O—CO—(C2-C6 alkenyl); —O—CO—(CH$_2$)$_r$—NR$_{11}$R$_{12}$; —O—CO—(CH$_2$)$_r$—N$^+$R$_{11}$R$_{12}$R$_{16}$; —O—CO—(CH$_2$)$_r$—COOH; —O—CO—(CH$_2$)$_r$—SO$_3$H; —O—CO—(CH$_2$)$_r$—O—PO(OH)$_2$; —NH—(CH$_2$)$_r$—COOH; —NH—(CH$_2$)$_r$—SO$_3$H; —NH—(CH$_2$)$_r$—O—PO(OH)$_2$; —NH—PO(OH)$_2$; —N$^+$(CH$_3$)$_2$—R$_{17}$; —O—PO(OH)—O—(CH$_2$)$_2$—N$^+$R$_{11}$R$_{12}$R$_{16}$; —O—PO(OH)—O—(CH$_2$)$_2$—NH$_3^+$; —O—PO(OH)—NH—PO(OH)—O—; —O—PO(OH)—O—CH$_2$—CH(N$^+$H$_3$)—COO$^-$; —CH$_2$—CH═CH$_2$; —CO—CH═CH$_2$; —CO—C(CH$_3$)═CH$_2$; —(CH$_2$)$_r$—COOH; —(CH$_2$)$_r$—O—SO$_3$H; —(CH$_2$)$_r$—O—PO(OH)$_2$; —SR$_{18}$; -G1-(C6-C14 arylene)-NR$_{11}$R$_{12}$; -G1-(C6-C14 arylene)-N$^+$R$_{11}$R$_{12}$R$_{16}$; -G1-(C6-C14 arylene)-COOH; -G1-(C6-C14 arylene)-SO$_3$H; -G1-(C6-C14 arylene)-O—PO(OH)$_2$; -G1-(C6-C14 arylene)-(CH$_2$)$_r$—NR$_{11}$R$_{12}$; -G1-(C6-C14 arylene)-(CH$_2$)$_n$—N$^+$R$_{11}$R$_{12}$R$_{16}$; -G1-(C6-C14 arylene)-(CH$_2$)—COOH; -G1-(C6-C14 arylene)-(CH$_2$)$_r$—SO$_3$H;

R$_{17}$ is —CH$_2$—CH═CH$_2$, —CO—CH═CH$_2$, —CO—C(CH$_3$)═CH$_2$, —(CH$_2$)$_q$—N$^+$R$_{11}$R$_{12}$R$_{16}$, —(CH$_2$)$_q$—NH—(CH$_2$)$_q$—SO$_3$H, —(CH$_2$)$_q$—NH—(CH$_2$)$_q$—COOH, —(CH$_2$)$_q$—NH—(CH$_2$)$_q$—O—PO(OH)$_2$, —PO(OH)$_2$, or —O—PO(OH)—O—(CH$_2$)$_2$—N$^+$R$_{11}$R$_{12}$R$_{16}$;

R$_{18}$ is hydrogen, C1-C18 alkyl, C2-C6 alkenyl with a terminal double bond, —CO—CH═CH$_2$, or —CO—C(CH$_3$)═CH—NR$_{11}$R$_{12}$;

n is an integer from 5 to 10; m is an integer from 0 to 4; o is an integer from 0 to 10; p is an integer from 1 to 16; q is an integer from 0 to 3; r is an integer from 1 to 6; and t is an integer from 1 to 14, and salts thereof.

In one embodiment, the amphiphilic compound Ia is symmetric and comprises two identical fatty acid chains, to each of which the same selectively cleavable headgroup or the same headgroup containing the same selectively cleavable group or moiety are attached along with the same stabilizing polar hydrogen-bonding group. The hydrogen-bonding group may be either attached to the aliphatic chain in the same proximity to said headgroup or situated within each of the headgroups.

As used herein the term "C1-C18 alkyl" typically refers to a straight or branched alkyl radical having 1-18 carbon atoms and includes, for example, methyl, ethyl, n-propyl, isopropyl, n-butyl, iso-butyl, tert-butyl, n-heptyl, 2,2-dimethylpropyl, n-hexyl, n-dodecyl, n-octadecyl and the like. The term "C2-C16 alkylene" refers to straight or branched alkylene groups having 2-16 carbon atoms and includes for example methylene, ethylene, propylene, butylene and the like. The term "C2-C6 alkenyl" refers to straight or branched hydrocarbon radicals having 2-6 carbon atoms and at least one terminal double bond and includes for example vinyl, prop-2-en-1-yl, but-3-en-1-yl, pent-4-en-1-yl, and hex-5-en-1-yl. The term "aliphatic chain of up to 16 atoms optionally interrupted by Q$_2$ or —CO-Q$_2$" means that the chain including the heteroatoms represented by Q$_2$ has up to 16 atoms.

The term "C6-C14 aryl" refers to an aromatic carbocyclic group having 6 to 14 carbon atoms consisting of a single ring or multiple condensed rings such as phenyl, naphthyl, and phenanthryl optionally substituted by C1-C6 alkyl. The term "heterocyclic" refers to a monocyclic, bicyclic or tricyclic fused-ring heteroaromatic group. Particular examples are pyridyl, pyrrolyl, furyl, thienyl, imidazolyl, oxazolyl, quinolinyl, thiazolyl, pyrazolyl, 1,3,4-triazinyl, 1,2,3-triazinyl, benzofuryl, isobenzofuryl, indolyl, imidazo[1,2-a]pyridyl, benzimidazolyl, benzthiazolyl and benzoxazolyl. The term "halogen" refers to fluoro, chloro, bromo or iodo.

For the preparation of some of the compounds of formula Ia and IIa, methods similar to those described in WO 03/047499 and WO 02/055011, both of the same applicant, can be used.

Some of the amphiphilic derivatives used for the preparation of nanoparticles according to the invention are new and their synthesis is described in the examples disclosed herein.

Symmetric amphiphilic compounds of the formula Ib, for example, can be synthesized starting from vernolic acid, which acyl residue has the formula:

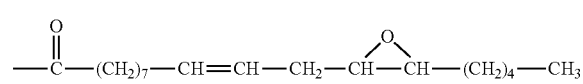

by reaction with an alkylene diamine, e.g. ethylene diamine, and opening of the oxiranyl ring with a carboxylic acid derivative, to obtain a derivative Ib:

R$_{19}$—CO—NH—(CH$_2$)$_2$—NH—CO—R$_{19}$ (Ib)

wherein R$_{19}$ is —(CH$_2$)$_7$—CH═CH—CH$_2$—CH(OH)—CH(R$_{20}$)—(CH$_2$)$_4$—CH$_3$ and R$_{20}$ is —OCOCH$_2$CH$_2$NH-phenyl-CH$_2$—CH(NH$_2$)—COOH.

In this example, R$_{20}$ is the headgroup moiety containing the selectively cleavable moiety p-aminophenylalanine that is linked to the fatty acid chain R$_{19}$ through an ester linkage, and said headgroup contains the hydrogen-bonding —NH group at the para position of the phenyl group and another hydrogen-bonding —OH group on the vicinal carbon atom (positions 1-2), both contributing to the stabilization of the nanoparticles based thereon.

Instead of ethylene as the spacer X4, another longer linear spacer or, for example, a branched spacer can be formed by reaction with a diamine such as: NH$_2$—CH$_2$—CH(CH$_3$)—CH$_2$—CH(CH$_3$)—CH$_2$—NH$_2$.

In another embodiment, the two fatty acid chains can be linked to the spacer by an ester instead of amide linkages, when the reaction is conducted with a dihydroxy compound such as diethylene glycol, thus obtaining, for example a compound of formula Ic:

R$_{19}$—CO—O—(CH$_2$)$_2$—O—CO—R$_{19}$ (Ic)

wherein R$_{19}$ is as defined for compound Ib above.

In a further embodiment, the bolaamphiphile has the formula Id:

R'$_{19}$—CO—NH—(CH$_2$)$_2$—NH—CO—R'$_{19}$ (Id)

wherein R'$_{19}$ is —(CH$_2$)$_7$—CH═CH—CH$_2$—CH(OH)—CH(R$_{21}$)—(CH$_2$)$_4$—CH$_3$; and R$_{21}$ is —NHCO—CH$_2$CH$_2$NH-phenyl-CH$_2$—CH(NH$_2$)—COOH.

In a still further embodiment, the amphiphilic compound has the formula Ie:

R'$_{19}$—CO—NH—(CH$_2$)$_2$—NH—CO—R"$_{19}$ (Ie)

wherein R'$_{19}$ is as defined above, R"$_{19}$ is —(CH$_2$)$_7$—CH═CH—CH$_2$—CH(OH)—CH(R$_{23}$)—(CH$_2$)$_4$—CH$_3$ and R$_{23}$ is —NH—CH$_2$CH$_2$NH-phenyl-CH$_2$—CH(NH$_2$)—COOH.

In the compounds of the formulas Id and Ie, the headgroup moiety R$_{21}$ or R$_{23}$ containing the p-aminophenylalanine group is linked to the fatty acid chain R'$_{19}$ or R"$_{19}$ through an amido or amino linkage, respectively, and said headgroup contains the hydrogen-bonding —NH group at the para position of the phenyl group and the hydrogen-bonding —CONH— or —NH— group two carbon atoms further, besides the hydrogen-bonding —OH group on the vicinal carbon atom. These compounds can be obtained from vemonia oil by amidation (Id) or aminolysis of the epoxide ring (Ie).

In certain embodiments of the present invention, nanoparticles are provided containing asymmetric bolaamphiphiles in which the aliphatic chains on both sides of the spacer X4 are identical, except for the headgroups, and wherein at least the bulkier headgroup contains the selectively cleavable group or moiety and will be on the outside of the nanoparticle surface. An example of such an asymmetric compound is a compound of formula If:

R$_{24}$—CO—NH—(CH$_2$)$_2$—NH—CO—R'$_{19}$ (If)

wherein R"$_{19}$ is as defined above, and contains the bulkier headgroup R$_{21}$ with the selectively cleavable moiety —NH—CH$_2$CH$_2$NH-phenyl-CH$_2$—CH(NH$_2$)—COOH;

$R_{24}$ is —$(CH_2)_7$—CH=CH—$CH_2$—CH(OH)—CH$(R_{25})$—$(CH_2)_4$—$CH_3$, and $R_{25}$ is —NH—CO—$CH_2$—COOH, a headgroup with no selectively cleavable group.

In still another embodiment, the nanoparticles comprise the symmetric bolaamphiphile of the formula Ig:

$$R_{27}\text{—CO—NH—}(CH_2)_2\text{—NH—CO—}R_{26} \quad (Ig)$$

wherein $R_{26}$ is —$(CH_2)_{12}$—CH(OH)—$CH_2$—$R_{23}$
$R_{27}$ is —$(CH_2)_{12}$—CH(OH)—$CH_2$—$R_{23}$ and
$R_{23}$ is —$NHCH_2CH_2NH$-phenyl-$CH_2$—$CH(NH_2)$COOH.

The compound Ig is a compound of formula Ia wherein $R_1$ and $R_5$ are —$(CH_2)_{10}$, $A_1$ and $A_3$ are —$CH_2$—$CH_2$—CH$(Y_1)$—, $Y_1$ is —OH, $R_2$ and $R_6$ are —$CH_2$, $A_2$ and $A_4$ are $R_{23}$, $R_3$ and $R_7$ are absent and $R_4$ and $R_8$ are H.

Compounds Ih-In below are some specific examples of amphiphilic compounds in which a hydrogen-bonding group is located within the headgroup containing the selectively cleavable group or moiety.

$$R_{28}\text{—CO—NH—}(CH_2)_2\text{—NH—CO—}R_{28} \quad (Ih)$$

wherein $R_{28}$ is —$(CH_2)_{12}$—$R_{23}$, and $R_{23}$ is —$NHCH_2CH_2NH$-phenyl-$CH_2$—$CH(NH_2)$COOH Compound Ih has the headgroup $R_{23}$ that contains both the selectively cleavable phenylalanine (levodopa-type) moiety and the hydrogen-bonding —NH— group attached to a $(CH_2)_{12}$ aliphatic chain with no further hydrogen-bonding groups in the aliphatic chain.

$$R_{29}\text{—CO—NH—}(CH_2)_2\text{—NH—CO—}R_{29} \quad (Ii)$$

wherein $R_{29}$ is —$(CH_2)_{12}$—$R_{21}$, and $R_{21}$ is —NHCO—$CH_2CH_2NH$-phenyl-$CH_2$—$CH(NH_2)$COOH.

The sole difference between the compounds Ih and Ii is that the headgroup moiety $R_{23}$ in Ih is attached to the $(CH_2)_{12}$ aliphatic chain by an amino linkage while the headgroup moiety $R_{23}$ is attached by an amido linkage.

Compound Ij is an example of an asymmetrical amphiphilic compound with a bulky headgroup $R_{29}$ containing the levodopa-type headgroup on one end and a smaller headgroup with a —COOH group on the other end:

$$R_{30}\text{—CO—NH—}(CH_2)_2\text{—NH—CO—}R_{29} \quad (Ij)$$

wherein $R_{29}$ is —$(CH_2)_{12}$—$R_{21}$, and $R_{21}$ is —NHCO—$CH_2CH_2NH$-phenyl-$CH_2$—$CH(NH_2)$COOH, and $R_{30}$ is —$(CH_2)_{12}$—COOH.

Another example of a symmetrical amphiphilic compound is represented by formula Ik:

$$R_{31}\text{—CO—NH—}(CH_2)_2\text{—NH—CO—}R_{31} \quad (Ik)$$

wherein $R_{31}$ is —$(CH_2)_{12}$—$R_{32}$, and $R_{32}$ is —$NHCH_2CH_2N^+(CH_3)_2$—$CH_2$—$CH_2$—$OCOCH_3$.

$R_{32}$ is an example of a headgroup containing both an acetylcholine-type group and the hydrogen-bonding —NH— group.

Another example of an asymmetrical amphiphilic derivative is a compound of the formula Il:

$$R_{33}\text{—CO—NH—}(CH_2)_2\text{—NH—CO—}R_{31} \quad (Il)$$

wherein $R_{31}$ is —$(CH_2)_{12}$—$R_{32}$, and $R_{32}$ is —$NHCH_2CH_2N^+(CH_3)_2$—$CH_2$—$CH_2$—$OCOCH_3$, and
$R_{33}$ is —$(CH_2)_{12}$—$R_{34}$, and $R_{34}$ is —$NHCH_2CH_2N^+(CH_3)_3$.

In the asymmetrical bolaamphiphile Il, one chain contains the bulkier ionic headgroup $R_{32}$ with the acetylcholine-type group and the hydrogen-bonding —NH— group, while the other aliphatic chain contains the smaller ionic headgroup.

Similarly to the amphiphilic compounds derived from vemolic acid and from saturated fatty acids exemplified above, further amphiphilic derivatives are derived from the lesquerolic acid found in lesquerella oil, which acyl residue has the formula:

—CO—$(CH_2)_9$—CH=CH—$CH_2$—CH(OH)—$(CH_2)_5CH_3$

In one embodiment, a symmetric bolaamphiphile has the formula Im:

$$R_{35}\text{—CO—NH—}(CH_2)_2\text{—NH—CO—}R_{35} \quad (Im)$$

wherein $R_{35}$ is —$(CH_2)_9$—CH=CH—$CH_2$—$CH(R_{36})$—$(CH_2)_5CH_3$; and $R_{36}$ is —$OCH_2CH_2NH$—CO—$CH_2$—$CH_2$—$CH(NH_2)$COOH.

$R_{36}$ is a headgroup containing the selectively cleavable residue of glutamic acid —$CH_2$—$CH_2$—$CH(NH_2)$COOH, and the hydrogen-bonding —CONH— polar group for stabilization.

In an additional embodiment, the nanoparticles of the invention comprise bolaamphiphiles derived from the ricinoleic acid found in castor oil, which acyl residue has the formula:

—CO—$(CH_2)_7$—CH=CH—$CH_2$—CH(OH)—$(CH_2)_5CH_3$

As an example, a symmetrical derivative has the formula In:

$$R_{37}\text{—CONH}(CH_2)_2\text{NH—CO—}R_{37} \quad (In)$$

wherein $R_{37}$ is —$(CH_2)_7$—CH=CH—$CH_2$—$CH(R_{38})$—$(CH_2)_5CH_3$, and
R38 is —$OCH_2CH_2NH$-phenyl-$CH_2$—$CH(NH_2)$COOH.

In a different embodiment of the invention, the nanoparticle comprise an amphiphilic compound that has, besides the polar or ionic cleavable headgroups or headgroups containing the selectively cleavable groups and optionally hydrogen-bonding groups, additional hydrophobic pendants either on the aliphatic chain and/or on the cleavable headgroup or headgroup containing the selectively cleavable group or moiety.

In one embodiment, a symmetric amphiphilic compound having a hydrophobic pendant on the headgroup containing the selectively cleavable group has the formula Io:

$$R_{39}\text{—CONH}(CH_2)_2\text{NH—CO—}R_{39} \quad (Io)$$

wherein $R_{39}$ is —$(CH_2)_{12}$—$N(R_{40})CH_2CH_2NH$-phenyl-$CH_2$—$CH(NH_2)$COOH; and $R_{40}$ is a C4-C16 alkyl.

In the above compound, the headgroups that contain the selectively cleavable levodopa-type group and the H-bonding group —NH—, also have a relatively long aliphatic chain $R_{40}$ attached to an amino group in both headgroup moieties to give extra stability due to hydrophobic interactions.

In another embodiment, an additional hydrophobic group of the amphiphilic compound ($R_{40}$) is not located in the headgroup moiety as above, but is bound to the fatty acid chain through an ether linkage, as shown in formula Ip:

$$R_{41}\text{—CONH}(CH_2)_2\text{NH—CO—}R_{41} \quad (Ip)$$

wherein $R_{41}$ is —$(CH_2)_7$—CH=CH—$CH_2$—$CH(OR_{40})$—$CH(R_{38})$—$(CH_2)_4CH_3$
$R_{40}$ is C4-C16 alkyl, and
$R_{38}$ is —$OCH_2CH_2NH$-phenyl-$CH_2$—$CH(NH_2)$COOH.

In particular embodiments, the nanoparticles of the invention comprise a bolaamphiphile of the formula IIa comprising a —CO—$R_{10}$—CO— midsection as follows:

$$R_8\text{-}R_7\text{-}A_4\text{-}R_6\text{-}A_3\text{-}R_5\text{-}Q_2\text{-CO—}R_{10}\text{—CO-}Q_1\text{-}R_1\text{-}A_1\text{-}R_2\text{-}A_2\text{-}R_3\text{-}R_4 \quad (IIa)$$

wherein all groups are as defined hereinabove and $Q_2$ and $Q_1$ are identical.

Such bolaamphiphiles can be synthesized starting, for example, from hexadecanoic acid [HO$_2$C(CH$_2$)$_{14}$CO$_2$H] and 11-hexadecen-1-ol [CH$_3$(CH$_2$)$_3$CH=CH(CH$_2$)$_{10}$OH], to obtain the following symmetric derivatives IIb and IIc with a headgroup containing a glutamic acid residue or a p-aminophenylalanine residue, respectively:

$$R_{42}-O-CO-(CH_2)_{14}-CO-O-R_{42}$$

wherein $R_{42}$ is —(CH$_2$)$_{10}$—CH(OH)—CH(R$_{43}$)—(CH$_2$)$_3$—CH$_3$, and $$R_{43} \text{ is } -O-CO-CH_2CH_2CH(NH_2)CO_2H \tag{IIb}$$

$$\text{or } R_{43} \text{ is } R_{21}: -NH-CO-CH_2CH_2CH-NH\text{-phenylalanine} \tag{IIc}$$

An asymmetric bolaamphiphile can be made having one bulkier headgroup containing a p-aminophenylalanine residue and a second smaller headgroup containing a glutamic acid residue, as shown by formula IId:

$$R_{44}-O-CO-(CH_2)_{14}-CO-O-R_{45} \tag{IId}$$

wherein $R_{44}$ is —(CH$_2$)$_{10}$—CH(OH)—CH(R$_{46}$)—(CH$_2$)$_3$—CH$_3$;
$R_{45}$ is —(CH$_2$)$_{10}$—CH(OH)—CH(R$_{47}$)—(CH$_2$)$_3$—CH$_3$;
$R_{46}$ is —NHCO—CH$_2$CH$_2$CH—NH-phenyl alanine;
and $R_{47}$ is —NHCO—CH$_2$CH$_2$CH$_2$CO$_2$H In particular embodiments, a symmetric bolaamphiphiles do not have hydrogen-bonding —OH group on the vicinal carbon atom as in compounds IIb-IId above, but rather the hydrogen-bonding group is located within the headgroup containing an ionic selectively cleavable group, as shown in formula IIe:

$$R_{48}-O-CO-(CH_2)_{16}-CO-O-R_{48} \tag{IIe}$$

wherein $R_{48}$ is —(CH$_2$)$_{11}$—NH—(CH$_2$)—N$^+$(CH$_3$)$_2$(CH$_2$)$_2$O—CO—CH$_3$ Cl$^-$;

This symmetric bolaamphiphile has a headgroup $R_{48}$ containing both the acetylcholine-type moiety and the hydrogen-bonding —NH— group, and can be prepared starting from HOOC—(CH$_2$)$_{16}$—COOH and 11-bromo-1-undecanol [Br(CH$_2$)$_{11}$OH].

In a further embodiment, starting again from HOOC—(CH$_2$)$_{16}$—COOH and 11-bromo-1-undecanol, the following asymmetric bolaamphiphile of formula IIf can be made with one acetylcholine headgroup and one glucosamine headgroup:

$$R_{49}-O-CO-(CH_2)_{16}-CO-O-R_{50} \tag{IIf}$$

wherein $R_{49}$ is —(CH$_2$)$_{11}$—NH—(CH$_2$)—N$^+$(CH$_3$)$_2$(CH$_2$)$_2$O—CO—CH$_3$ Cl$^-$;
and $R_{50}$ is —(CH$_2$)$_{11}$—NH—(CH$_2$)—NH—C$_6$H$_{11}$O$_5$
wherein —NH—C$_6$H$_{11}$O$_5$ is the glucosamine moiety, useful for transport across the biological barriers.

In particular embodiments, the nanoparticles of the invention comprise one or more bolaamphiphiles of the formulas IIa, comprising a —CO—R$_n$—CO— midsection, wherein n is 2-12, and a hydrogen-bonding group —OH located adjacent to the selectively cleavable headgroup on the vicinal carbon atom (positions 1-2). In more particular embodiments the bolaamphiphiles are the symmetric bolaamphiphiles herein designated Derivative 1, Derivative 4 and Derivative 5, or the asymmetric bolaamphiphile herein designated Derivative 3.

Derivative 4 is a known compound extensively used for preparation of nanoparticles according to the present invention. The symmetric Derivative 1 and Derivative 4 comprise the same selectively cleavable headgroup acetylcholine. In Derivative 1 the acetylcholine is linked through the oxygen atom of the acetyl moiety, whereas in Derivative 4 the acetylcholine is linked through one of the N$^+$-methyl groups. The way by which acetylcholine is bound to the fatty chain influences the ability of AChE to hydrolyze the headgroup and determines the selective disruption mechanism. When the choline ester is bound to the alkyl chain via the N+-methyl, AChE hydrolyzes the head group and decapsulates the active agent. However, when the choline ester head group is attached via the oxygen atom of the acetyl moiety, AChE will not as rapidly hydrolyze the head group and release of the encapsulated active agent will be substantially delayed.

In particular embodiments, the nanoparticles comprise one or more asymmetric bolaamphiphiles of the formula Ia. In a more particular embodiment the asymmetric bolaamphiphile is the compound herein designated Derivative 2, which comprises a terminal acetylcholine head group and a non-terminal acetylcholine headgroup located adjacent to an OH group (positions 1-2).

In certain embodiment, the nanoparticles comprise bolaamphiphiles which do not have a hydrogen-bonding group located adjacent to the cleavable headgroup. Such bolaamphiphiles may be prepared from ricinoleic acid based on castor oil. In particular embodiments, these bolaamphiphiles are symmetric bolaamphiphiles of the formula IIa. In more particular embodiments, these bolaamphiphiles are selected from the compounds herein designated Derivative 6, Derivative 7 and Derivative 8.

In further particular embodiments, the bolaamphiphiles are asymmetric bolaamphiphiles of the formula IIa. In more particular embodiments, these bolaamphiphiles are selected from the compounds herein designated Derivative 9 and Derivative 10.

The invention further encompasses the salts of the aforementioned bolaamphiphiles. Examples of salts include, but are not limited to acid addition salts formed with inorganic acids (hydrochloric acid, hydrobromic acid, sulfuric acid, phosphoric acid, nitric acid and the like) and salts formed with organic acids such as acetic acid, oxalic acid, tartaric acid, succinic acid, maleic acid, fumaric acid, maleic acid, ascorbic acid, benzoic acid, and the like. Said compounds can also be quaternary salts known by a person skilled in the art, which specifically include the quaternary salt of the formula —NRR'R"+ Z' wherein R, R', R" is independently hydrogen, alkyl or benzyl and Z is a counterion, including chloride, bromide, iodide, O-alkyl, toluenesulfonate, methylsulfonate, sulfonate, phosphate, or carboxylate.

Base addition salts are formed with metals or amines such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, and N-methylglucamine.

In certain embodiments, the nanoparticles of the present invention comprise additives which themselves are amphiphilic derivatives.

In a particular embodiment, the amphiphilic additive has one headgroup and is capable of forming bilayered vesicles. In a more particular embodiment, this amphiphile comprises two fatty acid chains linked to a midsection/spacer region such as —NH—(CH$_2$)$_2$—N—(CH$_2$)$_2$—N—, or —O—(CH$_2$)$_2$—N—(CH$_2$)$_2$—O—, and a sole headgroup preferably a selectively cleavable headgroup or one containing a polar or ionic selectively cleavable group or moiety, which is localized in said midsection preferably attached to the central N atom in the middle of the midsection region. The midsection also contains hydrogen-bonding groups provided by the —CONH— groups or polar ester groups, —C(=O)O— at the intersection with the fatty acid chains, and the headgroup moiety may also contain hydrogen-bonding groups.

These amphiphilic additives are added to the bolaamphiphile reaction mixture in the process of making nanoparticles in a controlled amount to enable the formation of monolayer vesicles by the predominant bolaamphiphiles. Some examples for different single head amphiphiles with cleavable headgroups are given in WO 03/047499 of the same inventors.

Thus, bolaamphiphiles comprising selectively cleavable headgroups bearing net ionic charge, preferably cationic headgroups, are advantageous according to the invention for three main reasons: (a) they form vesicles with good circulatory survival and ability of penetrating, intact, through biological barriers such as the blood-brain barrier (BBB), for example via transcytosis; (b) they provide vesicles with a selective disruption mechanism in the CNS, which enables the release of the encapsulated material in the brain in a controlled manner; and (c) they exhibit excellent encapsulation efficiency with anionic molecules such as peptides, proteins and nucleotides, via both complexation and encapsulation.

Bolaamphiphiles can be classified as either symmetrical or asymmetrical with respect to their headgroups. In symmetric bolaamphiphiles, both headgroups are the same whereas in asymmetrical bolaamphiphiles the headgroups are different with respect to their structure, electric charge and/or bulkiness.

In certain embodiments, the bolaamphiphiles are asymmetric bolaamphiphiles that have two headgroups of different size or bulkiness. The difference in headgroups size may vary from very small, intermediate, to a very large difference, and can be optimized to maximize amphiphile packing and thus vesicle stability for a bolaamphiphile with a given total size and a given span between the two headgroups on the aliphatic chain. Optimized size calculations for bolaamphiphiles with different headgroups are well known in the art.

Bolaamphiphiles may also be asymmetric with respect to their aliphatic tails or with respect to the nature and/or location of polar or hydrogen bonding groups on the aliphatic chain, relative to the headgroups. Additional asymmetry of bolaamphiphiles may be attributed to differences in aliphatic chain cross-sectional areas, and the presence or absence of aliphatic or aromatic chain pendants.

Asymmetric bolaamphiphiles may more readily form stable vesicles. In small vesicles formed from bolaamphiphiles bearing headgroups of different sizes, the size-difference can accommodate the differences in radii of curvature on the inner and outer surfaces of the vesicles, with the larger headgroups presented on the outer surface to maximize amphiphilic packing and intermolecular interactions.

Symmetrical bolaamphiphiles can form relatively stable structures by the use of additives such as cholesterol and cholesterol derivatives (e.g., cholesterol hemisuccinate, cholesterol oleyl ether, anionic and cationic derivatives of cholesterol and the like), or other additives including single headed amphiphiles with one, two or multiple aliphatic chains such as phopholipids, zwitterionic, acidic, or cationic lipids. Examples of zwitterionic lipids are phosphatidylcholines, phosphatidylethanol amines and sphingomyelins Examples of acidic amphiphilic lipids are phosphatidylglycerols, phosphatidylserines, phosphatidylinositols, and phosphatidic acids. Examples of cationic amphipathic lipids are diacyl trimethylammonium propanes, diacyl dimethylammonium propanes, and stearylamines cationic amphiphiles such as spermine cholesterol carbamates, and the like, in optimum concentrations which fill in the larger spaces on the outer surfaces, and/or add additional hydrophilicity to the particles. Such additives may be added to the reaction mixture during formation of nanoparticles to enhance stability of the nanoparticles by filling in the void volumes of in the upper surface of the vesicle membranes.

Proper design of bolaamphiphiles for a stable delivery system according to the invention will usually include long aliphatic segments spanning between their headgroups, one or more aliphatic chain pendants and asymmetry in head group size.

In certain embodiments, additives which may be bolaamphiphiles or single headed amphiphiles, comprise one or more branching alkyl chains bearing polar or ionic pendants, wherein the aliphatic portions act as anchors into the vesicle's membrane and the pendants (e.g., chitosan derivatives or polyamines or certain peptides) decorate the surface of the vesicle to enhance penetration through various biological barriers such as the intestinal tract and the BBB, and in some instances are also selectively hydrolyzed at a given site or within a given organ. The concentration of these additives is readily adjusted according to experimental determination.

In certain embodiments, the nanoparticles of the invention comprise mixtures of different multi-headed amphiphiles, and mixtures of at least one multi-headed amphiphile and at least one single headed amphiphile, which form vesicles with homogeneous or heterogeneous membrane structure. In any case, according to the invention, at least one of the multi-headed amphiphiles is a bolaamphiphile.

In particular embodiments, the nano-sized particles comprise a mix of bolaamphiphiles with different headgroups. In more particular embodiments, these bolaamphiphiles comprise different alkyl choline derivatives.

In a specific embodiment, the nanoparticle of the invention comprise a mixture of Derivative 1 and Derivative 4, preferably in the ratio 2:1, respectively. These bolaamphiphilic derivatives differ in the way the acetylcholine head group is linked to the aliphatic chain. Nanoparticles comprising said mixture loaded with a biologically active agent such as enkephalin released the encapsulated material more slowly compared to nanoparticle based only on Derivative 4, due to the mush less efficient cleavage of the acetylcholine group of Derivative 1.

In certain additional embodiments, the nanoparticles comprise bolaamphiphiles with alkyl choline headgroups and bolaamphiphiles with amino acid headgroups. Mixtures of different bolaamphiphiles usually form vesicles with heterogeneous or homogeneous monolayer membrane.

A mixture of bolaamphiphiles and single headed amphiphiles may form vesicles with a mosaic membrane morphology, most often a monolayer membrane formed by bolaamphiphiles, containing bilayer domains distributed therein formed by the single-headed amphiphiles. A mixture of bolaamphiphiles and triple-headed amphiphiles may give raise to heterogeneous monolayer membranes as well. The relationship between the chemical composition of the different amphiphiles and their compatibility to form homogeneous membranes vs mosaics is based on well established molecular relationships and may be used by one skilled in the art.

Preferably, the active agents comprise functional groups that may interact with amphiphilic headgroups and/or with other groups on the amphiphiles such as hydroxyl or other hydrogen bonding groups, hydrophobic moieties and the like.

Bioactive agents which may be delivered by the nanoparticles of the present invention include, without being limited to, natural or synthetic peptides, proteins, nucleosides, and polynucleotides, antiviral and antibacterial agents, e.g., antibiotics, antineoplastic and chemotherapeutic agents, and anti-inflammatory drugs. Non-limiting examples of peptides and proteins include analgesics peptides from the enkephalin class, calcitonin, cyclosporin, insulin, insulin analogs, oxytocin, tyrotropin releasing hormone, follicle stimulating hormone, luteinizing hormone, vasopressin and vasopressin analogs, catalase, superoxide dismutase, interleukin-II, interferon, colony stimulating factor, tumor necrosis factor (TNF), and melanocyte-stimulating hormone.

In certain embodiments, the peptides or proteins are selected from the glial cell line derived neurotrophic factor (GDNF) or the Gly-Leu-Phe (GLF) families.

GDNF is a highly conserved neurotrophic factor that is a distant member of the TGF beta superfamily. The GDNF gene product is processed to a disulphide-linked homodimer, which is a ligand for the RET protooncogene. GDNF protects and repairs dopamine-containing neurons, which degenerate in Parkinson's disease, and motor neurons, which die in amyotrophic lateral sclerosis. The use of GDNF in the treatment of Parkinson's disease has shown promise in the clinic. Treatment of spinal cord injuries with GDNF has also produced neurological improvement.

The GLF peptide is an immunostimulating peptide derived from α-lactalbumin, and was shown to prevent alopecia induced by anticancer agents.

In particular embodiments, polynucleotides selected from DNA or RNA fragments are delivered by the nanoparticles of the invention. In a more particular embodiment, the polynucleotide is a small interfering RNA (siRNA), a double-stranded RNA molecule of 20-25 nucleotides. siRNAs play a variety of roles in biology. Most notably, siRNAs are involved in the RNA interference (RNAi) pathway, where they interfere with the expression of a specific gene. In addition to their role in the RNAi pathway, siRNAs also act in RNAi-related pathways, e.g., as an antiviral mechanism or in shaping the chromatin structure of a genome. Some non limiting examples for target genes, or biological pathways which can be interfered by siRNA are epidermal growth factor receptor variant III gene, which is expressed in 40-50% of gliomas, and the phosphoinositide 3-kinase (PI3K)/Akt pathway, which plays a crucial role in medulloblastoma biology.

In additional particular embodiment, the DNA fragment delivered by the nanoparticle of the invention is a DNA plasmid such as the BGFP-N1 reporter gene.

In particular embodiments, the nano-sized particles of the invention are designed for delivering agents for the treatment or diagnosis of diseases or disorders associated with the CNS, particularly neurological/neurodegenerative diseases or disorders such as Parkinson's disease or Alzheimer's disease, or for treatment of brain tumors. According to these embodiments, the nanoparticles comprise multiheaded amphiphiles, preferably bolaamphiphiles, containing headgroups that are hydrolyzed or rearranged by degradative enzymes such as hydrolases, esterases, oxidases, decarboxylases, deaminases and isomerases. The degradative enzymes are either restricted to the brain, or alternatively, the delivery is applied in combination with enzyme inhibitors that do not penetrate the blood-brain-barrier, thereby preventing the premature disruption of the vesicles in the periphery where the degradative enzyme is inhibited. For example, the nanoparticles may contain headgroups which are derivatives of choline or thiocholine, or an aromatic amino acid-type compound and the peripheral enzyme inhibitors may be a choline esterase inhibitor, an aromatic L-amino acid decarboxylase inhibitor, a monoamine oxidase (MAO) inhibitor or a catechol-o-methyltransferase (COMT) inhibitor.

For the treatment of Parkinson's disease, the drugs to be delivered include, but are not limited to, levodopa (L-DOPA), carbidopa/levodopa, apomorphine, dopamine, and growth factors such as GDNF. By way of example, for delivery of levodopa, which is a negatively charged molecule due to a carboxylic group, the nanoparticle delivery vehicle will comprise amphiphiles containing cationic headgroups at a pH above the pKa of the levodopa that will form vesicles complexes with enhanced encapsulation resulting partially from encapsulation within the vesicles cores as well as salt complexes formation due to ionic interactions between the drug and the oppositely charged headgroups on the outer surface of the vesicles.

For the treatment of Alzheimer's disease, the drugs to be delivered include, but are not limited to, antibodies against components of the Alzheimer plaques, anti-inflammatory agents, growth factors, and muscarinic agonists that do not penetrate the BBB such as carbachol.

In particular embodiments, the nano-sized particles of the invention are designed for delivering agents for the treatment of cancer. Antineoplastic and chemotherapeutic agents that can be used include, without limitation, doxorubicin, cyclosporin, epirubicin, bleomycin, cisplatin, carboplatin, vinca alkaloids, e.g. vincristine, Podophyllotoxin, taxanes, e.g. Taxol and Docetaxel, and topoisomerase inhibitors, e.g. irinotecan, topotecan.

According to these embodiments, the therapeutic agent is primarily encapsulated in stable vesicles by known methods, e.g. active loading. In addition, substantial amounts of non-encapsulated and ionically charged drug may further be associated with oppositely charged groups on the outer surface of the vesicular membrane. In more particular embodiments, the vesicles are formed from bolaamphiphiles comprising aromatic L-amino acids headgroups which are presented on the outer vesicular surface (e.g. phenylalanine, tyrosine, levodopa, tryptophan or derivatives thereof). The carboxyl group of these aromatic amino acids is selectively cleaved by aromatic L-amino acid decarboxylase (AADC) in the brain, thus releasing the therapeutic drug in the brain. According to these embodiments, the nanoparticles are administered to a patient in need thereof in combination with a peripheral aromatic L-amino acid decarboxylase inhibitor (e.g. benserazide or carbidopa).

In certain additional embodiments, the surface ionic headgroups of the vesicular membrane are composed of one or more (thio)choline esters such as acetyl, butanoyl and hexanoyl choline/thiocholine, and the peripheral activity of cholinesterases (e.g., AChE present in the serum, liver and pancreas) is inhibited by quaternary cholinesterase inhibitors that do not penetrate the blood-brain barrier, such as neostigmine and pyridostigmine. Pyridostigmine is a carbamate used in humans for the treatment of myasthenia gravis due to its ability to inhibit acetylcholine esterase (AChE) without penetrating into the brain.

In certain additional embodiments, the surface ionic headgroups of the nanoparticles are dicarboxylic amino acids such as glutamic acid and aspartic acid that enhance transport through the BBB and decarboxylate by various enzymes in the CNS.

The hydrolyzing or degrading enzymes inhibitors mentioned above are usually administered to the patient about 15 min up to about 1 hour or 2 hours before the nanoparticles containing the drug are administered.

In certain embodiments, the nano-sized particles of the invention are designed for delivering active agents that exert their action in the blood circulation, have a short lifetime in the intestine and stomach and are poorly absorbed in the gastro-intestinal (GI) tract. According to these embodiments, the nanoparticles are designed to contain polar headgroups on the surface of the vesicular membrane, preferably choline esters that are hydrolyzed by cholinesterases in the blood, thus releasing the therapeutic agent in the blood circulation.

In particular embodiments, such nanoparticles are used for the treatment of diabetes, and may contain insulin. In other particular embodiments, these nano-sized particles are used for the treatment of multiple sclerosis and may contain, for example, Cop 1 (Copaxone), or be used for the treatment of breast cancer and contain antibodies such as Herceptin. Nano-sized particles for the treatment of immunodeficiency diseases may contain a mixture of immunoglobulins. No enzyme inhibitors are needed in these cases.

In certain embodiments, the invention provides nano-sized particles designed to deliver an antibacterial or antiviral agent for the selective treatment of viral and bacterial infections. According to these embodiments, the outer surface of the nanoparticles may contain functional groups (as headgroups or pendants on the outer vesicular membrane) that specifically interact with the viral wall such as, but not limited to, lectins and inactines, or with the bacterial wall such as, but not limited to, antibodies against the sequence LPXTG, which constitutes the cell wall sorting signals in a variety of bacteria as well as specific antibodies such as those against protein A of *Staphylococcus aureus*.

In certain embodiments, the invention provides nano-sized particles for the delivery of nucleic acids/genes for gene therapy. For example, liposome formulations comprising liposome-DNA combinations/complexes for intratracheal gene therapy of lung cancer, ovarian and other cancers as well as for gene therapy of hemophilia, and other diseases.

For the purpose of administering drugs to the brain, the nanoparticles of the invention may contain, besides the aforementioned selectively cleavable headgroups, ligands of specific receptors at the target site, presented as functional groups or pendants on the surface of the nanoparticles for targeting purposes, and/or ligands and surface groups which increase permeability through the BBB.

Examples of ligands for targeting purposes include nicotine, cytisine (nicotinic agonist), lobeline (nicotinic agonist), 1-glutamic acid (a ligand of the NMDA and AMPA receptors, since it has specific transporter that transfers it across the BBB), MK801 (NMDA antagonist), morphine (binds to the opiate receptors), enkephalins (pentapeptides that bind opiate receptors, can also be used as a headgroup that is cleaved specifically by a brain-specific peptidase called enkephalinase), benzodiazepines such as diazepam (valium) and librium (bind to the GABA receptor complex), dopamine agonists (e.g. bromokriptine, pergolide, ropirinol and the like), dopamine antagonists (neuroleptics such as halidol, benzamine (sulpiride), phenothiazines), tricyclic antidepressants (such as amytyptiline and desimipramine), muscarinic agonists (such as oxotremorine, pilocarpine and cis-2-methylspiro [1,3-oxathiolane-5,3'-quinuclidine], muscarinic antagonists (have very high affinity to the muscarinic receptors, such as atropine and scopolamine), cannabinoids such as delta-9-tetrahydro canabbinol (delta-9-THC) and arachidonyl ethanol amide.

Other additives which may be added to enhance BBB penetration are polycationic polymers such as polyethylene amine. Additional cationic surface groups to be introduced will include moieties based on protamine, polylysine or polyarginine, which have been shown to increase BBB penetrability, and peptides and proteins which are known to enhance transport through the BBB such as OX 26, transferrins, polybrene, histone, cationic dendrimer, synthetic peptides and polymyxin B nonapeptide (PMBN).

Other additives used according to the invention for improving brain drug delivery, include modified proteins or antibodies that undergo absorptive-mediated or receptor-mediated transcytosis through the blood-brain barrier, such as bradykinin B2 agonist RMP-7 or monoclonal antibody to the transferrin receptor. Other ligands are monosaccharides such as glucose, mannose, ascorbic acid and derivatives thereof, for example, glucose derivatives which use the glucose transporters GLUT-1 and p-aminophenyl-alpha-mannopyranoside.

Additives which enhance transport across membranes of the intestinal tract are also encompassed by the present invention. Such additives include, but are not limited to, chitosan (CS) and derivatives of chitosan, $Ca^{2+}$ chelators, medium-chain fatty acids or glycerides, steroidal detergents, and other mucoadhesive polymers.

The concentration of the various additives is readily adjusted according to experimental determination.

Chitosan (CS) and derivatives thereof are known intestinal absorption enhancers which are able to increase the paracellular permeability of peptide drugs across mucosal epithelia. The present inventors have shown that CS and particularly a novel CS derivative vernolyl-chitosan, a conjugate of CS and vemolic acid, is a very efficient penetrant of the BBB as well as of membranes of the GI tract and mucosal membranes.

Chitosan is a linear polysaccharide composed of randomly distributed β-(1-4)-linked D-glucosamine (deacetylated unit) and N-acetyl-D-glucosamine (acetylated unit). It is produced commercially by deacetylation of chitin, which is the structural element in the exoskeleton of crustaceans (crabs, shrimp, and the lime) and cell walls of fungi. The properties of CS and CS derivatives that make them important additives are their ability of adhering to the mucosal surface and transiently opening the tight junctions between epithelial cells (Silva et al., 1994) ("Microencapsulation of hemoglobin in chitosan-coated alginate microspheres prepared by emulsification/internal gelation", Silva et al. António J. Ribeiro, 2 Margarida Figueiredo, 3 Domingos Ferreira, 4 and Francisco VeigaPharm. Res. 1994; 11: 1358-1361).

Other chitosan and chitosan derivatives used in accordance with the present invention are commercially available CS or CS reduced in molecular weight (MW) by various processes (e.g., depolymerization of a commercially available CS using enzymatic degradation with cellulose, followed by precipitation at ~pH 7.0 and derivatization e.g., by quaternization of the amino groups with methyl iodide, conjugating chitosan with propylene or ethylene glycol to obtain chitosan-polypropylene glycol (PPG) and chitosan-polyethylene glycol (PEG) conjugates, respectively, and other derivatives known in the art.

In a particular embodiment, a novel chitosan-PEG additive, $CS-PEG_{2000}$ is used.

The aforementioned derivatives of chitosan are generally made by reaction with either the hydroxyl and/or amino groups of the chitosan polymer. The two hydroxyl groups have slightly different reactivity but can be functionalized by hydroxy active agents at high pH on either the acetylated or deacetylated monomers of the chitosan. The primary amine of the deacetylated monomer is available for reaction at moderate pH above 6 or so where a significant number of the amines are deprotonated. These chemistries provide new chitosan compounds bearing different properties from the original chitosan polymer.

Examples of chitosan derivatives made by reaction of the hydroxyl groups include, but are not limited to, carboxyalkylated chitosan, sulfonyl chitosan, carbohydrate-branched N-(carboxymethylidene) chitosan and N-(carboxymethyl) chitosan.

Many derivatives of chitosan are related to reactions of the amino groups on the glucosamine units, for example quaternary ammonium derivatives. Methods for synthesis of quaternary ammonium derivatives are well known in the art. Another example is derivatives resulting from coupling of the amino groups to carboxylic acids using peptide coupling chemistry. Known derivatives of low molecular weight chitosan polymers (less than 10,000 Da) N-conjugated with different amino acids include, but not limited to, chitosan-asparagine, -glycine, -alanine, -aspartic acid, -cysteine, -methionine and chitosan-arginine, wherein the amino acid is bound through a peptidic (amide) bond via its carbonyl to the primary amine on the glucosamines of chitosan.

Low molecular weight chitosan derivatives of about 80 kDa, preferably less than 30 kDa, are preferred according to the invention for the purpose of enhancing paracellular transport. CS of 30-50 kDa is kidney inert.

In particular embodiments, the present invention provides nanoparticles comprising at least one bolaamphiphile selected from the herein designated Derivative 1, Derivative 2, Derivative 3 and Derivative 4, an active agent selected from leu-enkephalin, carboxyfluorescein, $^{125}$I-GDNF and ovalbumin and at least one additive selected from vernolyl chitosan, Derivative 5, PEG-vernonia conjugate, cholesterol and cholesteryl hemisuccinate.

In another aspect, the present invention provides bolaamphiphiles of the formula Ia and IIa above. In certain embodiments, bolaamphiphiles of the formula IIa are provided comprising a —CO—$R_{10}$—CO— midsection. In particular embodiments, these bolaamphiphiles have a hydrogen-bonding group —OH located adjacent to the cleavable headgroup on the vicinal carbon atom (positions 1-2), which contributes to the stabilization of the nanoparticles based thereon. In more particular embodiments, these bolaamphiphiles are symmetric bolaamphiphiles selected from the compounds herein designated Derivative 1 and Derivative 5, or the asymmetric bolaamphiphile herein designated Derivative 3.

In other particular embodiments, symmetric or asymmetric bolaamphiphiles of the formula Ia are provided, which comprise the midsection —N(H)—$R_{10}$—N(H)— and a hydrogen bonding moiety located adjacent to the cleavable headgroup or the headgroup containing the cleavable group or moiety. In a more particular embodiment, the bolaamphiphile is the asymmetric compound herein designated Derivative 2, which comprises a terminal acetylcholine head group and a non-terminal acetylcholine headgroup located adjacent to an OH group (positions 1-2).

In certain embodiment, the present invention provides bolaamphiphiles, which do not have a hydrogen-bonding group located adjacent to the cleavable headgroup. These bolaamphiphiles may be prepared from ricinoleic acid based on castor oil, lesquerella oil and jojoba oil.

In particular embodiments, the bolaamphiphiles are symmetric bolaamphiphiles of the formula IIa. In more particular embodiments, these bolaamphiphiles are selected from the compounds herein designated Derivative 6, Derivative 7 and Derivative 8.

In further particular embodiments, the bolaamphiphiles are asymmetric bolaamphiphiles of the formula IIa. In more particular embodiments, these bolaamphiphiles are selected from the compounds herein designated Derivative 9 and Derivative 10.

In another aspect, the present invention provides pharmaceutical compositions comprising nano-sized particles of the invention and a pharmaceutically acceptable carrier.

The pharmaceutical composition of the invention can be delivered by any suitable route including, but not being limited to, intravenous, intramuscular, subcutaneous, or intraperitoneal injections, oral, nasal, lung or gum administration.

In certain embodiments, the pharmaceutical compositions are formulations for oral uptake. In certain additional embodiments, the formulations are injectable formulations for i.v. administration.

The oral formulations of the present invention preferably comprise agents that enhance penetration through the membranes of the GI tract and enable passage of intact nanoparticles containing the drug. These agents may be any of the additives mentioned above, preferably chitosan and derivatives thereof, serving as vehicle surface ligands, preferably as decorations or pendants on the vesicles, or the agents may be excipients added to the formulation.

In a further aspect, the present invention relates to the use of a nano-sized particle as described above for treatment or diagnosis of diseases or disorders selected from: (i) a disease or disorder associated with the CNS, particularly neurological/neurodegenerative diseases or disorders such as Parkinson's disease, Alzheimer's disease or multiple sclerosis; (ii) cancer such as breast cancer, prostate cancer and brain tumors; (iii) diabetes; (iv) an immunodeficiency disease; and (v) viral and bacterial infections.

In particular embodiments, the nano-sized particles of the invention are used for gene therapy.

In still another aspect, the present invention provides a method for treatment of a disease or disorder selected from: (i) a disease or disorder associated with the CNS, particularly neurological/neurodegenerative diseases or disorders such as Parkinson's disease, Alzheimer's disease or multiple sclerosis; (ii) cancer such as breast cancer and brain tumors; (iii) diabetes; (iv) an immunodeficiency disease; and (v) viral and bacterial infections, comprising administering to an individual in need thereof a nano-sized particle of the invention. When the target site of the drug encapsulated within the nanoparticle is the CNS, the nanoparticle is preferably administered together with a suitable peripheral enzyme inhibitor thus preventing premature disruption of the nanoparticle and release of the active agent outside the desired biological target site.

In a particular embodiment, the present invention provides a method for gene therapy.

EXAMPLES

Chemical Section

Materials

Vernonia oil, containing an average of 2.1 epoxy groups per molecule of oil, was purchased from Ver-Tech, Inc., Bethesda, Md. 5,5'-dithio-bis-(2-nitrobenzoic acid) (DTNB); Acetylcholinesterase (AChE) EC3.1.1.7, type V-S lyophilized from *Electrophorus electricus* (electric eel), catalogue No.: C-2888; Acetylthiocholine (ATC) iodide;

5(6)-Carboxyfluorescein (CF); Pyridostigmine (3-(Dimethylamino-carbonyloxy)-1-methylpyridinium bromide); Triton® X-100 (t-Octylphenoxy-polyethoxyethanol); Triton® X-100-Reduced form; Uranyl acetate dehydrate; Cholesterol (5-Cholesten-3β-ol); [5-Leucine] Enkephalin; L-α-Phosphatidylcholine Distearoyl (C18:0) (DSPC); Cholesteryl Hemisuccinate (5-Cholesten-3β-ol 3-hemisuccinate); Sephadex G-50; Trizma® Base (Tris{hydroxymethyl}aminomethane) and its hydrochloride salt; Perchloric acid (PCA), Trichloro acetic acid (TCA) and 2,2,2-Tribromoethanol (Avertin), all were of analytical grade and purchased from Sigma-Aldrich® Inc. 1,2-Dioleoyl-3Trimethylammonium-Propane(Methyl Sulfate Salt) (DOTAP) was purchased from Avanti Polar Lipids, Inc. Morphine HCl 20 mg/ml was purchased from Teva Pharmaceuticals Industries Ltd. $Na_2HPO_4$ and $KH_2PO_4$ were purchased from Biolab Ltd. $^3$H-cholesteryl oleyl ether ([1 alpha, 2 alpha (n)-$^3$H]Cholesteryl oleyl ether, 30-60 Ci/mmol, 1 mCi/ml), was purchased from Amersham Biosciences Inc. (UK). Solutions for inducing anastasia in animals—Ketamine HCl 100 mg/ml and Xylazine 2%, were obtained from the BGU's animal facility. Other standard chemicals were all purchased from commercial sources.

Methods i. Vesicle Formation

The methods used for nanoparticle preparation are well known in the art (see for example, New R. R. C. (1990) Preparation of liposomes In: Liposomes: A Practical Approach. IRL Press, Oxford) and include ethanol injection optionally followed by sonication or extrusion, and film-hydration-sonication where the sonication may be probe sonication or bath sonication.

Nanoparticle formation was conducted at room temperature (about 25° C.), which is above the transition point of the bolaamphiphilic compounds used in the present study. The preparation of liposomes from DSPC was done by FHE at 65° C., which is above the transition point of DSPC.

a. Vesicle Formation by Ethanol Injection (EI)

The following method was typically used for obtaining vesicle suspensions without additives:

Principle: the bolaamphiphile is dissolved in ethanol and the solution then rapidly injected through a fine needle below the surface of a stirring aqueous solution containing the water-soluble material to be encapsulated (i.e. CF or leu-enkephalin). The force of the injection and the stirring are sufficient to achieve complete and rapid mixing, so that the ethanol is diluted almost instantly in the aqueous phase and the lipid molecules are dispersed evenly throughout the medium. To assure good mixing and vesicle formation, a sonication step is performed following the injection of the bolaamphiphile ethanolic solution.

Standard procedure: 10 mg of a bolaamphiphile was dissolved in 50 µl ethanol. The following steps were done in the dark: 1 ml of the material to be encapsulated (dissolved in the relevant medium) was added to a 5 ml glass vial and stirred vigorously while the bolaamphiphile sample was injected thereto as quickly as possible through a HPLC syringe. The mixture was let to stir for 1-2 minutes, and then sonicated in Elma bath sonicator (50/60 Hz), 30 minutes at RT.

b. Vesicle Formation by Film-Hydration-Sonication (FHS) and Film-Hydration-Extrusion (FHE)

The following method was typically used for obtaining nanoparticles with additives. Unless mentioned otherwise, the molar ratio of bolaamphiphile:cholesteryl hemisuccinate: cholesterol was 2:1:1, respectively. When PEG-vernonia conjugates, was used as additive, the ratio of the bolaamphiphile to the PEG-vernolic acid conjugate was 10:1, respectively.

The bolaamphiphiles (10 mg) and the additives (in respective amounts) were dissolved in an organic solvent (chloroform, 750µ) using vortex. The solution was then placed in a 50 ml round bottom flask and held under vacuum, while rotating, at a rate of 90/min in a Rotarvap for 1-1.5 hours until all the solvent was completely evaporated. A dried thin film of the bolaamphiphile lining the walls of the flask was formed when the evaporation step was completed. Then, the thin film was hydrated by adding 1 ml of a solution containing the material to be encapsulated and mixed until all the film was dissolved. The solution was then either bath sonicated for 30 minutes at RT (FHS), or extruded (FHE) via 0.1/0.2 µm polycarbonate membrane (GE Water & Process Technologies, purchased from Tamar Laboratory Supplies Ltd.) till the solution became transparent (approx. 8-10 times).

When CS pendant were incorporated into the naopartivles, probe sonication was used rather than bath sonication and the method of the vesicle preparation was modified as described below. Unless mentioned otherwise, the molar ratio for CS was 10% relative to the bolaamphiphile.

Ten (10) mg of the bolaamphipiles and other additives (in respective amounts) except for the CS-vernolic acid conjugate were dissolved in chloroform, evaporated to form a thin film and rehydrated as described above. Then 1 ml of the material to be encapsulated dissolved in the relevant medium and containing 1 mg CS-vemolic acid conjugate was added and mixed until all the film was dissolved. The solution was placed in a 5 ml glass vial and sonicated in a probe sonicator (Vibra Cell Model H540/CV54, Sonics and Materials U.S.A) for 15 minutes in ice-cold container under the following conditions: 21% amplitude; pulse mode in cycles: 15 seconds pulse/10 seconds rest.

Under these conditions, the CS-vernolic acid conjugate is incorporated into the membrane of the vesicles and the CS moiety remains as pendant on the vesicle surface.

Example 1

Synthesis of Vernoyl Chitosan

The use of chitosan is limited due to its insolubility at pH higher than 6. One of the most common ways of providing hydrophilic characteristics to this polysaccharide is depolymerization.

i. Degradation of Chitosan by Hydrogen Peroxide

The oxidative degradation of chitosan was performed with hydrogen peroxide according to methods known in the art (e.g., Wu et al., 2005), using chitosan of an average molecular weight of 5-10 kDa, as follows:

Chitosan (5 g, Mn=54 KDa, degree of deacetylation 70-80%) was dispersed in 150 ml of water at RT for 1 hour. A solution of hydrogen peroxide (5 ml, 30%) was added dropwise to the chitosan dispersion and the reaction mixture was heated at 60° C. for 6 hours. The pH of the solution was then adjusted to pH=7 with a 1 M NaOH solution. The insoluble chitosan was filtered, the filtrate was evaporated, and absolute ethanol was added to the residue to precipitate the product that was repeatedly washed with absolute ethanol, and dried under vacuum to give 2.5 g (50% yield) of the water soluble chitosan oligomer.

The weight-average molecular weight (Mw), number-average molecular weight (Mn), and molecular weight dispersion Mw/Mn were measured by GPC in 0.2 mol/l $CH_3COOH/0.1$ mol/1 $CH_3COONa$ solutions as the eluent, using a TSKgel G4000PWXD column with a refractive index detector. The water soluble chitosan had Mn~1500-2000 Da, Mw=2800-3500 Da, and Mw/Mn=1.7-2.1.

Elemental analysis (%): C 38.88; H 6.63; N 6.12. The amount of $NH_2$ groups was about 45-50% and the amount of carboxylic groups determined by titration with NaOH was 1.1 mmol/g.

According to MALDI-TOF mass spectrometry the soluble chitosan obtained had the following structure:

$$\left[ \begin{array}{c} \text{OH} \\ \text{H} - \text{O} - \text{HO} - \text{O} \\ \text{NH} \\ \text{O} \end{array} \right]_{0.4} \left[ \begin{array}{c} \text{COOH} \\ \text{HO} - \text{O} - \text{OH} \\ \text{NH}_2 \end{array} \right]_{0.6}$$

MW of the unit 203  MW of the unit 175

The water soluble product was also characterized by FT-IR spectroscopy. FT-IR spectra showed that the intensity of the absorption band at 1593 $cm^{-1}$ characteristic of $NH_2$ in the degraded chitosan has higher intensity compared to the starting material.

ii. Preparation of Vernolic Acid N-Hydroxysuccinimide (Ver-NHS)

Ver-NHS was prepared following the procedure of Lapidot et al. (1967): to a mixture containing stoichiometric amounts of vernolic acid (2.4597 g, 0.00831 mol) and N-hydroxysuccinimide (0.9564 g, 0.00831 mol) in 40 ml of dry ethyl acetate, N,N'-dicyclohexylcarbodiimide (DCC; 1.7146 g, 0.00831 mol) in 5 ml of dry ethyl acetate was added. The mixture was stirred overnight at RT, the dicyclohexylurea (DCU) formed was filtered, and the solvent was removed under reduced pressure to yield the crude material comprising Ver-NHS and residual DCC and DCU. The pure Ver-NHS (1.5 g, Rf=0.2) was separated by flash-chromatography with a mixture of petroleum ether (60-80): diethyl ether 1:1(v/v) as the eluent. Yield: 48% iii. Preparation of Vernoyl Chitosan

The water-soluble chitosan obtained in (i) above, was reacted with Ver-NHS in order to covalently bind the vernonia moiety to the chitosan, as follows:

Chitosan obtained after treatment with hydrogen peroxide (0.2543 g, 0.8718 mmol of the amino groups of chitosan) was dissolved at 60-70° C. in dry DMSO. The solution was cooled to RT and triethyl amine was added. A 5.0 ml solution of Ver-NHS (0.0686 g, 0.1745 mmol) in dry DMSO was dropwise added to the chitosan solution and the reaction mixture was stirred at RT for 72 h. The triethyl amine was removed by evaporation and the remaining clear solution was freeze-dried. The dried powder was washed with diethyl ether, several times with ethanol and dried in a vacuum desicator at RT. A light-yellow powder was obtained. The product was characterized by FT-IR and $^{13}C$-NMR ($d_6$-DMSO).

Example 2

Synthesis of Vernolyl Glycol Chitosan

The water-solubility of chitosan (CS) can be substantially enhanced by attaching glycol units to it. Vernolyl glycol chitosan serves as an additive that enhances the penetrability and stability of the nanoparticles of the invention.

Vernolyl glycol chitosan was prepared based on the process of Kwon et al. (2003) for the preparation of hydrophobically modified glycol chitosans (HGCs), by the covalent attachment of vernolic acid N-hydroxysuccinimide (Ver-NHS) to glycol chitosan via an amide bond to a free amino group of a glucosamine unit. The synthesis of vernolyl glycol chitosan starting from glycol chitosan is depicted in Scheme 1.

A solution of Ver-NHS (0.1133 g, 0.000283 mol), prepared according to Example 1, in 60 ml of absolute ethanol was dropwise added to 40 ml of a 0.055 N $NaHCO_3$ solution of glycol chitosan (0.2364 g, 0.001153 mol). The mixture was stirred for 72 h in darkness. The reaction mixture was concentrated by reducing the solvent under reduced pressure at 45° C. down to a volume of 40 ml. The resulting aqueous dispersion of the polymer was extracted with diethyl ether (3×100 ml) and left to stand for 24 h in a fume hood for evaporating residual ether, then dialyzed against water (51) over 24 h, and finally freeze-dried to give a cotton-like-solid.

The polymer obtained was of ~400 units, MW of a unit 205 Da.

$$\left[ \begin{array}{c} \text{OH} \\ \text{O} \\ \text{O} - \text{HO} - \text{O} \\ \text{NH}_2 \end{array} \right]_n$$

and $NHCOCH_3$
n = 400

Different ratios of chitosan and Ver-NHS (5:1; 8:1; 10:1) were used to study the degree of substitution of the product and its properties as penetration enhancers via the intestinal membrane. The study of different rations of the components that make up the nanoparticle is needed to achieve an optimum composition of components for stability, penetrability through different biological barriers and a selective disruption at the target site.

Example 3

Preparation of PEG-Vernonia Conjugates

PEG derivatives of vernolic acid are used as additives in the preparation of the nanoparticles of the invention and were synthesized as follows:
i. Synthesis of $PEG_{2000}$-Vernonia Conjugate Two kinds of PEG-vernonia derivatives were prepared. The first kind was obtained by opening the epoxy ring and binding PEG to the oxygen atom via an ether bond (see Scheme 2). These derivatives are termed herein "PEG-ether derivatives" or "PEG(202)".

The second kind was obtained through an enzymatic reaction between vernolic acid and PEG to form an ester bond at the carboxylic group of vernolic acid, as shown in Scheme 3. These derivatives are termed herein "PEG-ester derivatives" or PEG(201)".

$PEG_{2000}$-Ether Derivative(PEG(202))

To a mixture containing 12.95 gr (0.006452 mol) of $PEG_{2000}$ and $BF_3$ etherate (600 µl), 2 gr (0.006452 mol) of methyl vernolate was injected every 5 to 10 minutes to in portions of 0.2 ml. The reaction mixture was refluxed at 80-86° C. for 7 hours. After cooling to RT, the reaction mixture was dissolved in ether and filtered. The crude product was purified by flash column chromatography using a mixture of chloroform:methanol as the eluent.

$PEG_{2000}$-Ester Derivative(PEG(201))

A mixture containing 1 gr (0.0034 mol) vemolic acid, 10 gr $PEG_{2000}$ (0.005 mol) and 0.0688 gr *Candida antarctica* (Novozym 435) lipase in toluene was refluxed at 75-80° C.

for 7 hours. The reaction mixture was cooled, the lipase was and filtered and the solvent was removed under reduced pressure. The crude product was purified by flash column chromatography using a mixture of chloroform:methanol as the eluent. Both kind of derivatives were characterized by FT-IR, NMR and MALDI Example 4

Synthesis of Derivative 1

The synthesis of Derivative 1 is schematically shown in Scheme 4.

i. Synthesis of Precursor 1 (Decane Divernolate)

A mixture of 92.1 g (0.31 mol) of vernolic acid and 27.5 g (0.155 mol) of 1,10-decandiol was refluxed with 0.77 g of lipase acrylic resin from *Candida antarctica* (Novozym 435) in 300 ml of toluene. Water formed during the reaction was removed by azeotropic distillation under reduced pressure (130-170 mm Hg). The temperature in the oil bath was held at 75-90° C. After 5 h, the reaction mixture was cooled, the lipase was filtered off, and the reaction mixture was concentrated to about 20 ml Thereafter, 400 ml of methanol were added, and the suspension obtained was left to stand overnight in a refrigerator. The precipitate was filtered off and washed with cold methanol to give 96.2 g of Precursor 1 in 85.7% yield (purity 89% HPLC).

(ii) Synthesis of Precursor 2 (Decane Divernolate Diglutaric Acid)

Precursor 2 was obtained by opening of the epoxy rings of the vernolate moieties of Precursor 1 with glutaric acid, as follows.

A mixture of 6.1 g (8.3 mmol) of decane divernolate and 16.5 g of glutaric acid in 50 ml of 1,2-dichloroethane were refluxed for 48 h. After cooling the reaction mixture, 200 ml of chloroform were added, and the solution was washed with a saturated solution of NaCl until the pH reached 6. The chloroform solution was dried over magnesium sulfate and filtered, and the solvent was removed under reduced pressure to give 7.8 g of crude Precursor 2. Purification of the crude product by column chromatography on silica gel 60 using hexane:ether:acetic acid 5:5:0.1 as the eluent yielded 3.5 g of pure product (41.6% yield) with 98% purity.

iii. Synthesis of Precursor 3

Precursor 3 was obtained by esterification of Precursor 2, as follows:

A solution of 10.3 g of 1-ethyl-3-(3,3-dimethylaminopropyl)carbodiimide (EDCI) in 100 ml of dry dichloromethane was added dropwise to an ice-cooled solution of 50 ml of dry dichloromethane containing 12.9 g (0.013 mol) of Precursor 2, 8.85 g of 4-dimethylaminopyridine (DMAP), and 16 ml of N,N-dimethyl amino ethanol. The reaction mixture was stirred for two days, and chloroform was then added. The organic solution was washed several times with a saturated NaCl solution until the pH reached 7. The organic solvent was dried over anhydrous magnesium sulfate and the solvent was removed under reduced pressure to yield 9 g of crude product (70% HPLC, methanol:water (0.15% trifluorocicetic acid) 95:5; Rt-6.9 min, flow 0.5 ml/min, TLC chloroform:methanol 8:2). The product, Precursor 3, was purified by flash column chromatography with acetone as the eluent.

iv. Synthesis of Derivative 1.

Precursor 3 was quaternized to obtain the symmetric bolaamphiphile Derivative 1 as follows:

A mixture of 0.7 g Precursor 3 and 1 ml of CH$_3$I in 20 ml of dry dichloromethane was stirred for 24 h in a cooling bath. The solvent was removed under reduced pressure, and the iodide was exchanged with chloride on an ion-exchange resin (Amberlyst CG-400-I) to yield 0.67 g of the pure product Derivative 1 (see Scheme 4).

Example 5

Synthesis of Derivative 2

The asymmetric bolaamphiphile Derivative 2 was synthesized starting from the synthesis of vernol monoaminoamide as follows:

i. Synthesis of Precursor 5 (Vernol Monoaminoamide)

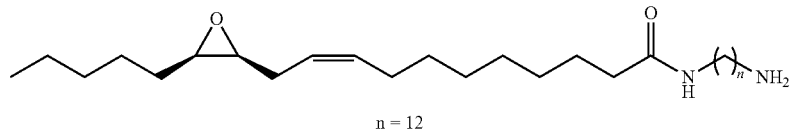

Precursor 5 n = 12

A mixture containing 3.1 g (0.0155 mol) of 1,12-diaminododecane in 30 ml of dry toluene and 2.0 ml (0.001 mol) of a 0.5 N sodium methoxide solution in absolute ethanol was heated to 70° C. To this solution, 4.8 g (0.0155 mol) of methyl vernolate in 20 ml of toluene were dropwise added during 3.5 h, and the reaction mixture was heated for two more hours. After cooling, the solidified reaction mixture was triturated with hexane, filtered and washed with water until pH=7. The crude product was purified by column chromatography on Silica gel using a mixture of CHCl$_3$:CH$_3$OH:25% NH$_4$OH in the ratio 100:10:1. The pure compound (MP=124-126° C.) was characterized by FT-IR, NMR, an ESI-MS (m/z: 479.6[M+H]$^+$).

ii. Synthesis of Precursor 6 (Mono-Chloroacetatae of Vernol Monoaminoamide)

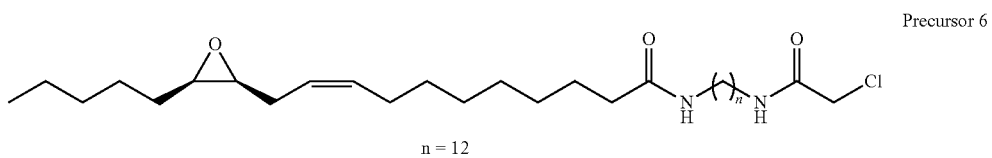

Precursor 6 n = 12

Into a three-neck round-bottom flask, Precursor 5 prepared in (i) above was introduced (0.01 mol), along with 20 ml of dry chloroform and 1.4 ml (0.01 mol) triethyl amine. The reaction mixture was cooled to −12° C. and a solution of chloroacetyl chloride (0.66 ml, 0.0083 mol) in 5 ml of dry chloroform was dropwise added during 40 minutes. The temperature of the reaction raised to 10° C. After an additional hour at RT, chloroform was added to the reaction mixture and the organic phase was washed with a 5% solution of $NaHCO_3$ until pH=7, and then with water until no more $Cl^-$ ions could be detected. The organic phase was separated and dried over anhydrous magnesium sulfate. The solvent was removed under reduced pressure and the crude product was purified by column chromatography on silica gel with a mixture of chloroform:acetone (8:2) as the eluent. The pure product was obtained in a 58% yield as a white solid (MP=115-116), and was characterized by FT-IR, NMR, and ESI-MS.

iii. Synthesis of Precursor 7 (Di-Chloroacetatae of Vernol Monoaminoamide)

of dry acetone was refluxed for about 10 hours. after cooling to RT, 5 ml of dichloromethane and 15 ml of diethyl ether were added and the reaction mixture was refrigerated overnight. The supernatant was separated by decantation to leave a viscous liquid. This procedure was repeated several times to remove the unreacted N,N-dimethylamino ethyl acetate. Solvent residues were removed under reduced pressure to give the product Derivative 2 in a 48% yield as a colorless viscous liquid that was characterized by FT-IR, NMR, ESI-MS (m/z: 420.1$[M-2Cl]^{2+}/2$).

$^1$H NMR ($d_6$ DMSO) δ ppm 9.15 (1H, m, N$\underline{H}$—C(O)—$CH_2$—$N^+$), 7.86 (1H, m, $CH_2$—$CH_2$—N$\underline{H}$—C=O), 5.41, 5.32, (2H, 2 m, C$\underline{H}$=C$\underline{H}$), 5.23, 5.08 (1H, 2 d, J=5.5 Hz, CH—OH), 4.81 (1H, m, C$\underline{H}$—O—C=O), 4.68 (2H, m, $^+$N—C$\underline{H}_2$—C=O), 4.45 (4H, m, O—C$\underline{H}$—$CH_2$—$N^+$), 4.30 (2H, s, $^+$N—C$\underline{H}_2$—C=O), 3.94, 3.90 (4H, 2 m, O—$CH_2$—C$\underline{H}_2$—$N^+$), 3.50 (1H, m, C$\underline{H}$—OH), 3.32 (6H, m, $(CH_3)_2$—$N^+$), 3.28 (6H, s, $(C\underline{H}_3)_2$—$N^+$), 3.08 (2H, q, $^3$J=6.3 Hz, $CH_2$—C$\underline{H}_2$—NH—C(O)—$CH_2$—$N^+$), 2.98 (2H, q, $^3$J=6.3 Hz, $CH_2$—C$\underline{H}$—NH—C(O)—$CH_2$—$CH_2$), 2.31, 2.12 (2H, 2 m, CH—C

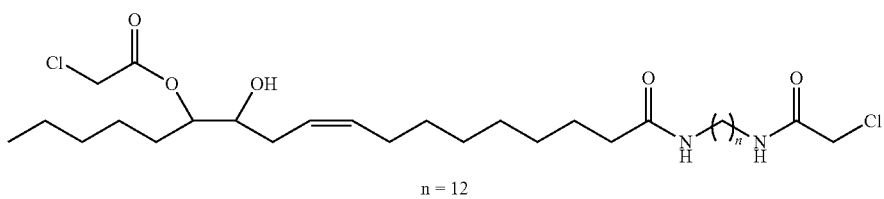

Precursor 7 n = 12

A solution containing Precursor 6 (0.001 mol) in 4 ml of dry toluene and chloroacetic acid (0.13 g, 0.0014 mol) was heated at 75° C. for 12 h. Chloroform was added and the organic phase was washed with a 5% solution of $NaHCO_3$ until pH=7, and then with water. The organic phase was separated and dried over anhydrous magnesium sulfate. The solvent was removed under reduced pressure and the crude product was purified by column chromatography on silica gel with a mixture of chloroform:acetone (7:3) as the eluent. The pure product was obtained in a 44% yield as a sticky white solid (MP=115-116), and was characterized by FT-IR, NMR, ESI-MS (m/z: 671.9$[M+H]^+$).

iv. Synthesis of Derivative 2

Derivative 2 was obtained by quaternization of Precursor 7, as follows:

$\underline{H}_2$—CH=CH), 2.04, 2.03 (6H, 2 s, C$\underline{H}_3$—C=O), 2.03 (2H, m, $CH_2$—$CH_2$C=O), 1.98 (2H, m, CH=CH—C$\underline{H}_2$—$CH_2$), 1.22-1.60 (38H, m, $(C\underline{H}_2)_n$), 0.84 (3H, m, $CH_2$—C$\underline{H}_3$); $^{13}$C NMR ($d_6$ DMSO) δ ppm 171.9 (NH—$\underline{C}$(O)—$CH_2$—$CH_2$), 169.8 and 169.7 ($CH_3$—$\underline{C}$=O), 164.8 and 164.6 (CH—O—C=O), 163.0 (NH—$\underline{C}$(O)—$CH_2$—$N^+$), 132.4, 131.0 and 125.6, 124.1 ($\underline{C}H$=$\underline{C}H$), 78.6, 78.4 ($\underline{C}H$—O—C=O), 70.2 and 69.7 ($\underline{C}H$—OH), 62.5 and 62.4 (O—$CH_2$—$\underline{C}H_2$—$N^+$) 62.3 and 61.3 ($^+$N—$\underline{C}H_2$—C=O), 57.6 (O—$\underline{C}H$—$CH_2$—$N^+$), 51.7 and 51.5 (($\underline{C}H_3)_2$—$N^+$), 38.5 and 38.2 ($\underline{C}H_2$—NH—C=O), 35.3 ($\underline{C}H_2$—C=O), 32.3, 31.5, 31.2, 31.0, 30.7, 29.6-28.6, 27.8, 26.8, 26.7, 26.4, 25.3, 24.8, 24.4, 22.0 and 21.9 ($\underline{C}H_2$—$CH_3$), 20.6 ($\underline{C}H_3$—C=O), 13.9 and 13.8 ($CH_2$—$\underline{C}H_3$); FT-IR (neat) $v_{max}$ 3303 (OH), 3318 (NH), 3063, 3020, 2927, 2857, 1745 (C=O), 1673, 1646 and 1554 (amide bands), 1460, 1373, 1234 (acetate band), 1055, 953, 722

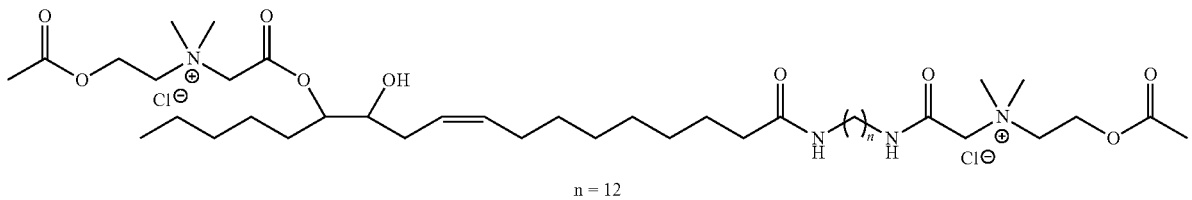

Derivative 2 n = 12

A mixture containing Precursor 7 (0.001 mol) and 0.294 g (0.0022 mol) of N,N-dimethylamino ethyl acetate in 2 ml $cm^{-1}$; ESI-MS m/z: 420.1 $[M-2Cl]^{+2}/2$; Argentometric titration calcd for $C_{46}H_{88}Cl_2N_4O_9$: 7.77% $Cl^-$ found 8.20% $Cl^-$.

Example 6

Synthesis of Derivative 3

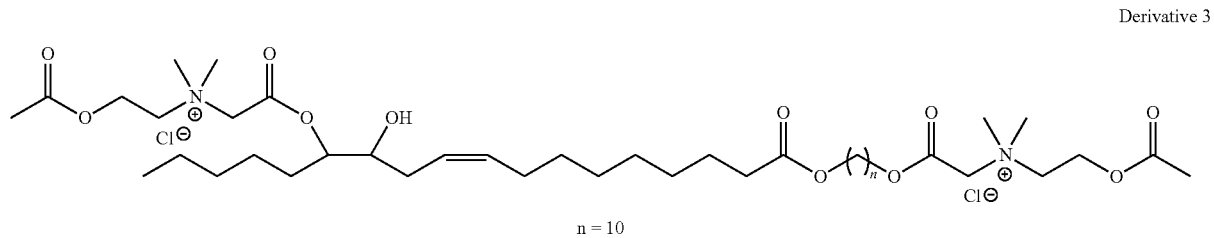

Derivative 3 n = 10

Derivative 3 was synthesized similarly to the synthesis Derivative 2 starting with vernol-monohydroxyester instead of vernol monoaminoamide, via formation of the dichloro acetate of venolmonoester and then quaternization with N,N-dimethylamino ethyl acetate to give the respective Derivative 3.

Example 7

Synthesis of Derivative 5

The symmetric bolaamphiphile Derivative 5, which bears two glutamic acid head groups, can be used as an additive in the formation of nanoparticles comprising asymmetric bolaamphiphiles such as Derivative 3 and or symmetric Derivative 4, and constitutes only about 10% of the total amphiphiles' mass. Addition of this bolaamphiphile resulted in nanoparticles having improved blood circulatory. Nanoparticles comprising Derivative 5 as the major amphiphilic component can also be used for targeted delivery of active agent.

Derivative 5 was synthesized from Precursor 1 (decane divernolate) which in turn was obtained form vernolic acid according to the procedure described in Grinberg et al., 2008. The synthesis of Derivative 5 is depicted in Scheme 6.

A mixture of protected glutamic acid Z-Glu-OBzl (1.83 g, 4.93 mmol) and Precursor 1 (1.5 g, 2.052 mmol) was heated to melt (100-110° C.) under a nitrogen atmosphere. Tetramethyl ammonium bromide (TMABr) (0.2134 g) was added, and the mixture was stirred and heated for about 12 hours.

After cooling, a yellow viscous liquid was separated and dissolved in diethyl ether. The TMABr that did not dissolve in the ether solution, was filtered out. The crude (2.3744 g; ~67.5% yield) Precursor 8 was purified with a silica gel column using a mixture of Hexane:EtOAc, 2:1 as the eluent to give 0.9196 g; 30.4% yield with a 99% purity.

Catalytic hydrogenation in the presence of Pd/C removed the two protecting groups of each head groups in one stage and Derivative 5 was obtained as follows:

Into a pressure resistant vessel, a solution of Precursor 8 (0.9196 g; 0.621 mmol) in 25 ml MeOH, and the catalyst were added (10% Pd/C). Hydrogen was bubbled into the reactor ($H_2$ pressure of 40 Lb./in$^2$ was produced in the vessel). The hydrogenation of the product (for purposes of removing the protective groups) was carried out for about 1 hour with continuous shaking.

The catalyst was filtered, the solvent was removed under reduced pressure to obtain white-opaque, very tough solid flakes Derivative 5 (0.4397 g; 0.42 mmol; 68.5% yield with 99.7% HPLC purity).

Example 8

Synthesis of Derivatives 6, 7 and 8

The synthesis of symmetric and asymmetric bolaamphiphilic compounds from castor oil based on ricinoleic acid or methyl ricinoleate with the acetylcholine head group attached through the nitrogen atom of acetyl choline is as follows.

i. Synthesis of Precursor 9 (1,10-Decandiricinoleate)

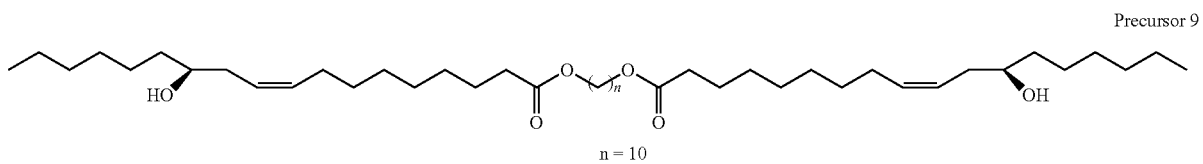

Precursor 9 n = 10

A mixture of 2.121 g (7.12 mMol) of ricinoleic acid, 0.7 g (3.6 mMol) of 1,10-decandiol and 100 mg of lipase acrylic resin from *Candida Antarctica* in 6.9 ml of toluene was boiled. Water formed during the reaction was removed by azeotropic distillation under diminished pressure of 130 mm-170 mm Hg. The temperature in the bath oil was 75-90° C. After 5 hours the reaction mixture was cooled, the lipase was filtered and the solvent was evaporated. Silica gel Column chromatography in Petroleum Ether/Diethyl Ether 6/1, 6/4 led to 2.647 g of pure Precursor 9 as a white powder. M. P 45-47° C.

FT-IR $v_{max}$ 3383 (OH), 3017 (CH=CH), 2927, 2855, 1736 (O—C=O), 1461, 1246, 1175, 1081 cm$^{-1}$.

ii. Synthesis of Precursors 10 and 11

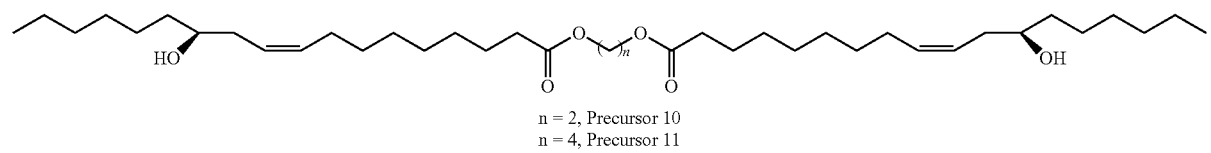

n = 2, Precursor 10
n = 4, Precursor 11

A mixture of the diols HO—(CH$_2$)$_2$—OH and HO—(CH$_2$)$_4$—OH (1.25 mole), methyl ricinoleate (2 moles) and lipase acrylic resin from *Candida antartica* (Novozym 435) (10% of the weight of reagents) was stirred at room temperature in CHCl$_3$ overnight. The reaction was monitoring by TLC (Petroleum Ether/Ether: 1/1). The slurry mixture obtained was dissolved in ether, the lipase was filtered off and the outcome solution was evaporated under vacuum. The mixture of esters was purified by column chromatography with increasing polarity Petroleum ether/Ether: 7/1; 6/4; 1/1. Precursor 10 was obtained at 34.7% yield (0.35 g), and Precursor 10 was obtained at 35.6% yield (0.72 g).

iii. Synthesis of Precursors 12 and 13

Precursors 12 and 13 were synthesized from methyl ricinoleate (2.58 g, 8.27 mMol), and 1,2-ethandiol or (0.321 g, 5.17 mMol) or 1,10-decandiol (0.85 g, 4.91 mMol), and 4 ml CHCl$_3$ as described above for Precursor 11.

Precursors 12 was obtained at 65% yield (0.35 g). FT-IR $v_{max}$ 3396; 3007; 2927; 2855; 1737; 1455; 1388; 1255; 1081; 1040; 876 cm-1.

and Precursors 13 was obtained at 60% yield (0.64 g).

FT-IR $v_{max}$ 3258 (OH), 3174 (CH=CH), 3070, 2956, 2852, 1735, 1461, 1260, 1177, 1051, 883, 796, 721 cm-1.

iv. Synthesis of Precursors 14-18

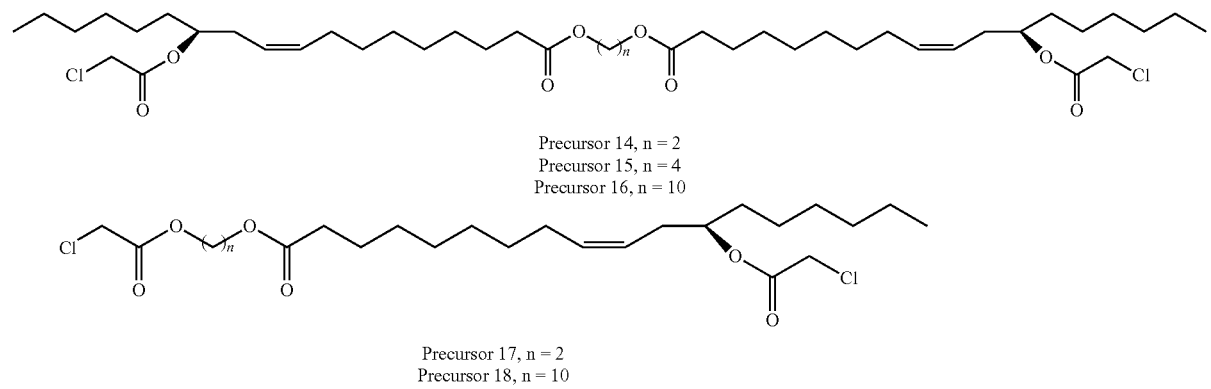

Precursor 14, n = 2
Precursor 15, n = 4
Precursor 16, n = 10

Precursor 17, n = 2
Precursor 18, n = 10

A mixture of Precursors 9-13 (1 mole) and chloroacetyl chloride (6 moles) in 2 ml of dry diethyl ether was magnetically stirred at room temperature for 3 hours. The reaction was monitored by TLC. The reaction mixture was dissolved in diethyl ether, washed with a solution of 5% NaHCO$_3$ and distilled water till pH 5.39. The organic phase was separated, dried with MgSO$_4$, filtered and the solvent was removed under reduced pressure and crude products were obtained and characterized by FT-IR, $^1$H and $^{13}$C NMR and MS.

Precursor 14 (dichloroacetate 1,2-ethandiricinoleate) was obtained at 89% yield (0.39 g).

FT-IR $v_{max}$ 3017, 2954, 2928, 2856, 1756 (COCH$_2$Cl), 1741, 1466, 1369, 1285 (CH$_2$Cl), 1260, 1171, 1037, 797 cm$^{-1}$.

Precursor 15 (dichloroacetate 1,4-butandiricinoleate) was obtained at 90% yield (0.80 g).

FT-IR $v_{max}$ 3017, 2926, 2854, 1756 (COCH$_2$Cl), 1734, 1455, 1365, 1312, 1286 (CH$_2$Cl), 1180, 1091, 1030, 876, 805 cm-$^1$.

Precursor 16 (dichloroacetate 1,10-decandiricinoleate) was obtained at 94% yield (1.07 g).

FT-IR $v_{max}$ 3022, 2930, 2922, 2855, 1759 (COCH$_2$Cl), 1737, 1453, 1426, 1371, 1291 (CH$_2$Cl), 1264, 1185, 1083, 1015, 964, 849, 719 cm-1.

Precursor 17 (dichloroacetate 1,2-ethanmonoricinoleate) was obtained at 92% yield (0.47 g).

FT-IR $v_{max}$ 3014, 2962, 2927, 2856, 1759 (COCH$_2$Cl), 1740, 1468, 1416, 1384, 1309, 1291 (CH$_2$Cl), 1254, 1172, 1037, 964, 863, 778 cm$^{-1}$.

Precursor 18 (dichloroacetate 1,10-decanmonoricinoleate) was obtained at 94% yield (0.8 g).

FT-IR $v_{max}$ 3011, 2928, 2856, 1760, 1736, 1472, 1286, 1257, 1175, 1009, 787 cm$^{-1}$.

$[\alpha]^{20}_{58}$=+14.7 (solvent: CHCl$_3$; 0.1313 g/ml)

v. Synthesis of Derivatives 6-10

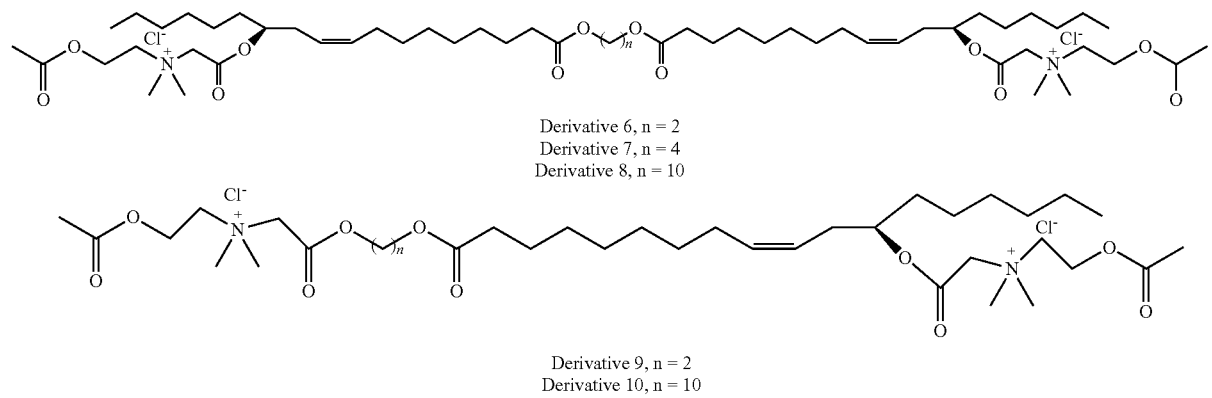

Derivative 6, n = 2
Derivative 7, n = 4
Derivative 8, n = 10

Derivative 9, n = 2
Derivative 10, n = 10

A mixture of dichloroacetate Precursors 14-18 (1 mole) and N,N-dimethylaminoethyl acetate (8 moles) was stirred at 75-80° C. for 3 hours. After cooling, the reaction mixture was purified by silica gel column chromatography eluted with acetonitrile:water (10:1) or washed several times with CH$_2$Cl$_2$ and diethyl ether to remove excess of N,N-dimethylaminoethylacetate and pure amphiphilic products were obtained.

Derivative 6 was obtained at 50% yield after CC (130 mg)

FT-IR $v_{max}$ 3007, 2950, 2923, 2854, 1743, 1645, 1471, 1367, 1238, 1158, 1021, 876 cm-1.

$^1$H NMR (CDCl$_3$, 500 MHz) δ ppm 5.52 (2H, m, CH$_2$—CH=CH—CH$_2$—CH(O)), 5.31 (2H, m, CH$_2$—CH=CH—CH$_2$—CH(O)), 4.95 (2H, m, CH=CH—CH$_2$—CH(O)), 4.95, 4.87 (4H, 2 d, 17.0 Hz, O—CO—CH—N$^+$), 4.56 (4H, m, N$^+$—CH$_2$CH$_2$—O), 4.34 (4H, m, N$^+$—CHCH$_2$—O), 3.73, 3.73 (12H, 2 s, CH$_3$—N$^+$—CH$_3$), 4.27 (4H, s, CH$_2$—CH$_2$—O—CO), 2.32 (8H, 2 t, 7.5 Hz, O—CO—CH$_2$—CH$_2$, CH=CH—CH$_2$—CH(O)), 2.02 (4H, m, CH$_2$—CH=CH—CH$_2$—CH(O)), 2.10 (6H, s, CH$_3$—CO), 1.60, 1.30 (40H, m, CH$_2$), 0.88 (6H, t, 6.5 Hz, CH$_3$—CH$_2$). $^{13}$C NMR (CDCl$_3$, 500 MHz) δ ppm 173.57 (CO—CH$_2$—CH$_2$), 169.81 (CO—CH$_3$), 164.52 (CO—CH$_2$—N$^+$), 133.60 (CH$_2$—CH=CH—CH$_2$—CH(O)), 123.22 (CH$_2$—CH=CH—CH$_2$—CH(O)), 62.69 (CH=CH—CH$_2$—CH(O)), 62.21 (O—CO—CH$_2$—N$^+$), 57.73 (N$^+$—CH$_2$CH$_2$—O), 62.21 (N$^+$—CH$_2$CH$_2$—O), 52.62 (CH$_3$—N$^+$—CH$_3$), 62.69 (CH$_2$—CH$_2$—O—CO), 33.29 (O—CO—CH$_2$—CH$_2$), 34.15 (CH=CH—CH$_2$—CH(O)), 27.38 (CH$_2$—CH=CH—CH$_2$—CH(O)), 20.83 (CH$_3$—CO), 31.59, 29.40, 29.07, 25.26, 24.86, 22.56 (CH$_2$), 14.03 (CH$_3$—CH$_2$). MS (ESI) m/z: 483.66[(M–2Cl$^-$+H$^+$)/2], 1037.32 Calcd for C$_{54}$H$_{98}$O$_{12}$Cl$_2$N$_2$.

Derivative 7 was obtained at 67% yield after CC (486.5 mg).

FT-IR $v_{max}$ 3018, 2930, 2856, 1740, 1650, 1462, 1387, 1238, 1208, 1155, 1065, 943, 872, 794 cm-1.

$^1$H NMR (CDCl$_3$, 500 MHz) δ ppm 5.50 (2H, m, CH$_2$—CH=CH—CH$_2$—CH(O)), 5.30 (2H, m, CH$_2$—CH=CH—CH$_2$—CH(O)), 4.95 (2H, m, CH=CH—CH$_2$—CH(O)), 4.88, 4.84 (4H, 2 d, 17 Hz, O—CO—CH—N$^+$), 4.58 (4H, m, N$^+$—CH$_2$CH$_2$—O), 4.35 (4H, m, N$^+$—CH$_2$—CH$_2$—O), 3.73, (12H, s, CH$_3$—N$^+$—CH$_3$), 4.09 (4H, 2 t, 5.0 Hz, CH$_2$—CH$_2$—O—CO), 2.34 (4H, m, O—CO—CH$_2$—CH$_2$) 2.29 (4H, t, 7.5 Hz, CH=CH—CH$_2$—CH(O)), 2.02 (4H, q, 5.5 Hz, CH$_2$—CH=CH—CH$_2$—CH(O)), 2.10 (6H, s, CH$_3$—CO), 1.70, 1.60, 1.30 (44H, m, CH$_2$), 0.88 (6H, t, 7.0 Hz, CH$_3$—CH$_2$)). $^{13}$C NMR (CDCl$_3$, 500 MHz) δ ppm 173.84 (CO—CH$_2$—CH$_2$), 169.80 (CO—CH$_3$), 164.50 (CO—CH$_2$—N$^+$), 133.61 (CH$_2$—CH=CH—CH$_2$—CH(O)), 123.20 (CH$_2$—CH=CH—CH$_2$—CH(O)), 63.73 (CH=CH—CH$_2$—CH(O)), 62.64 (O—CO—CH$_2$—N$^+$), 57.80 (N$^+$—CH$_2$CH$_2$—O), 62.64 (N$^+$—CH$_2$CH$_2$—O), 52.67 (CH$_3$—N$^+$—CH$_3$), 63.73 (CH$_2$—CH$_2$—O—CO); 34.30 (CH=CH—CH$_2$—CH(O)), 33.27 (O—CO—CH$_2$—CH$_2$), 27.37 (CH$_2$—CH=CH—CH$_2$—CH(O)), 20.85 (CH$_3$—CO), 31.59, 29.38, 29.04, 25.35, 25.25, 24.92, 22.56 (CH$_2$), 14.03 (CH$_3$—CH$_2$). MS (ESI) m/z: 497.62[(M–2Cl$^-$)/2], 1066.24 calcd for C$_{56}$H$_{102}$O$_{12}$Cl$_2$N$_2$. Argentometric titration calcd: Cl$^-$ 6.67%; found: 6.41%.

Derivative 8 was obtained at 65% yield after washing (220.9 mg).

FT-IR (NaCl) $v_{max}$ 3016, 2926, 2856, 1741, 1638, 1460, 1427, 1379, 1236, 1172, 1038, 946 cm-1.

$^1$H NMR (CDCl$_3$, 500 MHz) δ ppm 5.53 (2H, m, CH$_2$—CH=CH—CH$_2$—CH(O)), 5.30 (2H, m, CH$_2$—CH=CH—CH$_2$—CH(O)), 4.96 (2H, m, CH=CH—CH$_2$—CH(O)), 4.91, 4.83 (4H, 2 d, 17.0 Hz, O—CO—CH$_2$—N$^+$), 4.59 (4H, m, N$^+$—CH$_2$CH$_2$—O), 4.37 (4H, m, N$^+$—CH$_1$CH$_2$—O), 3.75 (12H, s, CH$_3$—N$^+$—CH$_3$), 4.07 (4H, t, 6.5 Hz, CH$_2$—CH$_2$—O—CO), 2.36 (4H, m, O—CO—CH$_2$—CH$_2$), 2.31 (4H, t, 7.5 Hz, CH=CH—CH$_2$—CH(O)), 2.03 (4H, q, 7.0 Hz, CH$_2$—CH=CH—CH$_2$—CH(O)), 2.12 (6H, s, CH$_3$—CO), 1.62, 1.32 (56H, m, CH$_2$), 0.89 (6H, t, 7.0 Hz, CH$_3$—CH$_2$)). $^{13}$C NMR (CDCl$_3$, 500 MHz) δ ppm 173.83 (CO—CH$_2$—CH$_2$), 169.87 (CO—CH$_3$), 164.11 (CO—CH$_2$—N$^+$), 133.86 (CH$_2$—CH=CH—CH$_2$—CH(O)), 123.16 (CH$_2$—CH=CH—CH$_2$—CH(O)), 64.36 (CH=CH—CH$_2$—CH(O)), 62.69 (O—CO—CH$_2$—N$^+$), 57.73 (N$^+$—CH$_2$CH$_2$—O), 62.69 (N$^+$—CH$_2$CH$_2$—O), 52.68 (CH$_3$—N$^+$—CH$_3$), 64.36 (CH$_2$—CH$_2$—O—CO), 34.36 (CH=CH—CH$_2$—CH(O)), 33.27 (O—CO—CH$_2$—CH$_2$), 27.37 (CH$_2$—CH=CH—CH$_2$—CH(O)), 20.81 (CH$_3$—CO), 31.58, 29.38, 39.33, 29.10, 29.05, 28.60, 25.88, 25.24, 24.96, 22.55 (CH$_2$), 14.01 (CH$_3$—CH$_2$). MS (ESI) m/z: 539.7 [(M–2Cl$^-$)/2], 1150.4 calcd for C$_{62}$H$_{114}$O$_{12}$Cl$_2$N$_2$. Argentometric titration calcd: Cl$^-$ 6.18%; found: 6.17%.

Asymmetric Derivative 9 was Obtained at 37% Yield (220 mg).

FT-IR $v_{max}$ 3011, 2930, 2856, 1756, 1743, 1667, 1456, 1378, 1238, 1204, 1160, 1090 cm-1.

Asymmetric Derivative 10 was Obtained at 47% Yield (330 mg).

FT-IR $v_{max}$ 3031, 2926, 2855, 1746, 1652, 1467, 1376, 1239, 1059, 754 cm$^{-1}$.

$^1$H NMR (CDCl$_3$, 500 MHz) δ ppm 5.50 (1H, m, CH$_2$—CH=CH—CH$_2$—CH(O)), 5.30 (1H, m, CH$_2$—CH=CH—CH$_2$—CH(O)), 4.98 (2H, s, CH$_2$—CH$_2$—O—CO—CH—N$^+$), 4.94 (1H, m, CH=CH—CH$_2$—CH(O)—CO), 4.79 (2H, s, CH—O—CO—CH—N$^+$), 4.59, (2H, m, CH—O—CO—N$^+$—CH$_2$CH$_2$—O), 4.55 (2H, t, 5.0 Hz, CH$_2$—O—CO—N$^+$—CH$_2$CH$_2$—O), 4.31 (2H, m, CH—O—CO—N$^+$—CH$_2$CH$_2$—O), 4.28 (2H, m, CH$_2$—O—CO—N$^+$—CH$_2$CH$_2$—O), 4.17 (2H, t, 7.0 Hz, CH$_2$—CH$_2$—O—CO—CH$_2$N$^+$), 4.06 (2H, t, 6.5 Hz, CH$_2$—CH$_2$—O—CO—CH$_2$), 2.88 (12H, s, CH$_3$—N$^+$—CH$_3$), 2.34 (2H, m, O—CO—CH$_2$—CH$_2$, CH$_2$), 2.29 (2H, t, 7.5 Hz, CH=CH—CH$_2$—CH(O)), 2.09, 2.07 (6H, 2 s, CH$_3$—CO), 2.03 (2H, q, 7.5 Hz, CH$_2$—CH=CH—CH$_2$—CH(O)), 1.62, 1.30 (26H, m, CH$_2$), 0.87 (3H, t, 7.0 Hz, CH$_3$—CH$_2$). $^{13}$C NMR (CDCl$_3$, 500 MHz) δ ppm 173.88 (CO—CH$_2$—CH$_2$), 170.23, 169.788 (CO—CH$_3$), 165.09, 164.49 (CO—CH$_2$N$^+$), 133.58 (CH$_2$—CH=CH—CH$_2$—CH(O)), 123.21 (CH$_2$—CH=CH—CH$_2$—CH(O)), 66.71 (CH=CH—CH$_2$—CH(O)—CO), 64.25 (CH$_2$—CH$_2$—O—CO—CH$_2$N$^+$), 62.62 (CH—O—CO—CH$_2$—N$^+$), 62 (CH$_2$—CH$_2$—O—CO—CH$_2$—N$^+$), 58.07 (CH(O)CO—CH$_2$—N$^+$—CH$_2$—CH$_2$—O), 57.84 (CH$_2$—O—CO—CH$_2$—N$^+$—CH$_2$—CH$_2$—O), 62 (N$^+$—CH$_2$—CH$_2$—O), 52.79 (CH$_3$—N$^+$—CH$_3$), 62.73 (CH$_2$—CH$_2$—O—CO—CH$_2$), 34.41 (CH=CH—CH$_2$—CH(O)), 33.29 (O—CO—CH$_2$—CH$_2$), 27.35 (CH$_2$— CH=CH—CH$_2$—CH(O)), 31.57, 30.82, 29.34, 29.25, 29.13, 29.01, 28.57, 28.25, 25.85, 25.60, 25.22, 24.99, 22.52 (CH$_2$), 13.96 (CH$_3$—CH$_2$). MS (ESI) m/z: 399.54 [(M−2Cl$^-$)/2], 870.08 Calcd for C$_{44}$H$_{82}$O$_{10}$Cl$_2$N$_2$.

Example 9

Preparation of Derivative 4-Nanoparticles Loaded with Leu Enkephalin

Derivative 4, presented in Scheme 5, was synthesized as described in Grinberg et al. (Grinberg et al., 2008). This bolaamphiphile, bearing two acetylcholine headgroups, wherein the acetyl choline is linked to the amphiphile via its nitrogen atom, was used for the preparation of nanoparticles comprising leu-enkephalin. The additives cholesterol and cholesteryl hemisuccinate were added to Derivative 4 in order to confer more stability to the vesicles which form from the symmetric bolaamphiphile.

The following stock solutions were prepared: 10 mg/kg leu-enkephalin in TBS (TBS), pH 8.5; Derivative 4 (10 mg/ml); dissolved in chloroform together with the additives cholesteryl hemisuccinate and cholesterol (1:1). From these stock solutions, a thin film was prepared and hydrated in the following procedure:

Derivative 4, cholesterol and cholesteryl hemisuccinate in molar ratio of 100:25:25, respectively, mixed in chloroform were placed in a round bottom flask attached to a vacuum evaporator. Evaporation took place for 2 hours under vacuum to obtain a dry film.

One (1) ml of the leu-enkephalin solution was added into the round bottom flask containing the dry film, and the film was hydrated for 20 min while rotating the flask (without vacuum) to obtain a suspension. This suspension was extruded through a membrane 100 nm microporous (Nucleopore) until the solution becomes transparent (approx. 8-10 times).

The leu-enkephalin was encapsulated at a pH above its pI point and thus had a net negative charge, which interacted with the oppositely charged headgroups of Derivative 4. The percentage of encapsulation was to 2 to 4 times higher than when leu-enkephalin was encapsulated at a pH below its pI point, where it had a net cationic charge.

Example 10

Preparation of Nano-Sized Particles Comprising Distearyl Phosphatidyl Choline and Leu Enkephalin Nanoparticles comprising distearyl phosphatidyl choline (DSPC) as the amphiphilic compound and cholesterol as an additive where made by the FHE technique as described in Example 9, at 65° C., which is above the transition point of DSPC.

Example 11

Preparation of Nano-Sized Particles Comprising Derivative 1 or Derivative 4 and Leu Enkephalin Nanoparticles comprising leu-enkephalin encapsulated within vesicles made form Derivative 1 or Derivative 4 were prepared by the ethanol injection technique. The bolaamphiphiles Derivative 1 and 4 have a similar amphiphilic backbones but the acetyl choline headgroups [CH$_3$—C(O)—O—(CH$_2$)$_2$—N$^+$(CH$_3$)$_3$] are bonded to the backbone differently: via the quaternary nitrogen in Derivative 4 (see Scheme 5) and via the methyl group in Derivative 1 (see Scheme 4).

An ethanolic solution of Derivative 1 or Derivative 4 (10 mg bolaamphiphile in 50 μl ethanol) was prepared and injected into a 1 ml stirring aqueous solution (saline, 0.9% NaCl) containing 2.5 mg leu-enkephalin. The resulting suspension was sonicated in a bath sonicator (36 KHz) at 35° C. for 1 hour to form nanoparticles of about 100 nm in diameter. These nanoparticles were used (administered to mice) no later than 1 hour after preparation thereof.

Example 12

Preparation of Nano-Sized Particles Comprising Derivative 2 or Derivative 3

Asymmetric bolaamphiphiles Derivatives 2 and 3 were synthesized as described in Examples 5 and 6, respectively, and nanoparticles based on these amphiphiles were prepared by the ethanol injection technique, as follows:

An ethanolic solution of Derivative 2 or Derivative 3 (10 mg bolaamphiphile in 50 μl ethanol) was injected into a stirring aqueous solution of PBS 0.9% NaCl. The resulting suspension was sonicated in a bath sonicator (36 KHz) at 35° C. for 1 hour to form opalescent solutions.

Examination of the solutions under transmission electron microscopy (TEM) showed that Derivative 2 formed vesicles and ribbons while Derivative 3 formed primarily nano sized vesicles.

The stability of nano vesicles formed from the asymmetric Derivative 3 was studied by dynamic light scattering (DLS) and TEM and compared to the stability of vesicles made from the symmetric bolaamphiphile Derivative 4 by exactly the same procedure. Suspensions containing the vesicles were left to stand for 1, 5, 10 and 30 days to assess the stability of the nanoparticle solution/suspension, and then analyzed by DLS and TEM. The results showed that vesicles made from asymmetric Derivative 3 were considerably more stable with respect to size and homogeneity.

Example 13

Preparation of Nano-Sized Particles Comprising the Additive Vernoyl Chitosan

Nanoparticles comprising various active agents encapsulated within vesicles made from various amphiphiles along with the additive vernolyl chitosan were prepared by the thin film technique as described in Example 9. Nanoparticles comprising chitosan additive are most suitable for the preparation of oral formulations.

i. Nanoparticles Comprising Derivative 4 Encapsulating Leu-Enkephalin

Solutions of 10 mg/kg leu-enkephalin in TBS pH 8.5, 10 mg/ml Derivative 4 in 300 µl chloroform, was mixed with the additives cholesteryl hemisuccinate and cholesterol (1:1) each separately dissolved in 300 µl of chloroform to form a solution with a molar ratio of 100:25:25 for Derivative 4, cholesterol and cholesteryl hemisuccinate, respectively. The solution was evaporated under for 2 hours under vacuum to obtain a dry film. One (1) ml solution of 2.5 mg leu-enkephalin were added, and the film was hydrated for 20 min to obtain a suspension.

The suspension was transferred into a 5 ml glass vial, and 10 molar percent (or 1 mg) of vernolyl chitosan (MW ~80K) obtained according to Example 1 were added (the molar ratio of Derivative 4:cholesterol:cholesteryl hemisuccinate: chitosan was 100:25:25:10, respectively). Dissolution of chitosan in the bolaamphiphile-active agent reaction mixture simultaneously with its incorporation into the vesicles membrane and vesicle formation was carried out in the same solution by sonication (probe sonication: sonicate 30% power, pulses 10 seconds, rest 10 seconds for 15 minutes until complete. The chitosan appeared to dissolve as indicated by the disappearance of turbidity).

ii. Nanoparticles Comprising Derivative 4 Encapsulating Carboxyfluorescein

The marker carboxyfluorescein (CF) was used as a model of non polymeric active agents. Nanoparticles comprising Derivative 4/cholesterol/cholesteryl hemisuccinate/vernoyl chitosan (molar ratio 100:25:25:10, respectively) encapsulating CF, were prepared as described above using a solution of 1 mg/ml CF for hydration of the thin film.

iii. Nanoparticles Comprising Distearyl Phosphatidyl Choline Encapsulating Leu-Enkephalin Nanoparticles comprising distearyl phosphatidyl choline (DSPC), and cholesterol (molar ratio 100:30, respectively) encapsulating leu-enkephalin, were prepared as described in (i) but the amount of DSPC dissolved in chloroform was 20 mg instead of 10 mg and twice as that of Derivative 4.

Example 14

Preparation of Nano-Sized Particles Comprising a Mixture of Bolaamphiphiles

For the purpose of optimizing the delivery efficiency, active agent targeted release efficiency, stability and durability in the blood stream, nanoparticles comprising mixtures of different bolaamphiphiles were prepared.

(i) Nanoparticles Comprising Derivative 4, Derivative 5 and Leu-Enkephalin

Nanoparticles comprising a mixture of the symmetric bolaamphiphiles Derivative 4 and Derivative 5 and encapsulated leu-enkephalin, were prepared according to the procedure described in Example 9, starting with a solution comprising these two derivatives in a weight ratio of 9:1 Derivative 4:Derivative 5, respectively dissolved in chloroform.

(ii) Nanoparticles Comprising Derivative 1, Derivative 4 and Leu-Enkephalin

Nanoparticles comprising a mixture of the symmetric bolaamphiphiles Derivative 1 and Derivative 4 and leu-enkephalin, and vernoyl chitosan as additive were prepared according to the procedure described in Example 13, starting with a solution comprising these two derivatives in a weight ratio of 2:1 Derivative 1:Derivative 4, respectively dissolved in chloroform.

Example 15

Preparation of Nano-Sized Particles Comprising Derivative 4, Vernoyl Chitosan and Various Amounts of Leu Enkephalin For the purpose of optimizing the nanoparticles' packing, delivery efficiency, stability, or surface properties, nanoparticles were prepared form Derivative 4 and vernoyl chitosan as additive, and various amounts of leu-enkephalin. Nanoparticles were prepared as described in Example 13 using solutions of 5, 10 or 20 mg/kg leu-enkephalin in TBS pH 8.5. Instead of extrusion through a filter the solution containing the nanoparticles was probed sonicated at RT until the temperature raised to 40° C.

Example 16

Preparation of Nano-Sized Particles Comprising Derivative 4, Carboxyfluorescein and PEG-Vernonia Derivatives Nanoparticles comprising the fluorescent marker carboxyfluorescein (CF) encapsulated within vesicles made from Derivative 4 and decorated with $PEG_{2000}$-vemonia derivatives, cholesteryl hemisuccinate and cholesterol as pendants were prepared by the thin film technique as described in Methods and in Example 9. Two kinds of PEG-vemonia derivatives were used: PEG-ether derivatives, wherein PEG is bound via an ether bond to the oxygen of the opened epoxy ring of vernolic acid (PEG(202)), and PEG-ester derivatives, wherein PEG is bound via an ester bond to the carboxylic group of vernolic acid (PEG(201)). These PEG-vernonia derivatives were prepared as described in Example 3.

Solutions of 20 mg/ml CF in PBS pH 8.0, 10 mg/ml Derivative 4 in a solution of the additives cholesteryl hemisuccinate and cholesterol (1:1) in chloroform were prepared. PEG(201) and PEG(202) were added as solids and dissolved to obtain a solution comprising Derivative 4, cholesterol, cholesteryl hemisuccinate and PEG(201) or PEG(202) in a molar ratio of 100:25:25:10, respectively. A dry film was obtained as described in Example 9. Then, 1 ml of the PBS solution of CF were added, and the film was hydrated for 20 min. The particles were not isolated and used in the solution they were made.

The percentage of CF encapsulation was 20%. This relatively high encapsulation percentage is attributed to electrostatic interactions between the anionic groups of CF and the cationic headgroups of the bolaamphiphile.

Example 17

Preparation of Nano-Sized Particles Comprising Derivative 4 and Ovalbumin

Nanoparticles comprising tritiated ovalbumin encapsulated within vesicles made from Derivative 4 and the additives cholesteryl hemisuccinate and cholesterol were prepared by the FHE technique as described in Methods and in Example 9.

Briefly, the following solutions were prepared: 10 mg/kg tritiated ovalbumin in PBS at a pH 8.0, above its pI point, 10 mg/ml Derivative 4 in 300 µl in chloroform, cholesteryl hemisuccinate and cholesterol (1:1) each dissolved in 300 µl chloroform. The solutions of Derivative 4, cholesterol and cholesteryl hemisuccinate were mixed to give a molar ratio of 100:25:25, added to a round bottom flask and a dry film was obtained. The thin film was hydrated for 20 min with 1 ml of the ovalbumin solution and the suspension thus obtained was extruded through a membrane 100 nm microporous (Nucleopore) until the solution becomes transparent (approx. 8-10 times).

Example 18

Preparation of Nano-Sized Particles Comprising Derivative 4 and $^{125}$I-GDNF

Nanoparticles comprising $^{125}$I-GDNF (glial cell line-derived neurotrophic factor) encapsulated within vesicles made from Derivative 4 and the additives cholesteryl hemisuccinate and cholesterol are prepared by the thin film technique as described in Example 17, using a stock solution of 2 mg/kg $^{125}$I-GDNF in TBS at pH 9.5 for hydrating the thin film and forming nanoparticles encapsulating $^{125}$I-GDNF.

Example 19

Preparation of Nano-Sized Particles Comprising Derivative 1 and a DNA Plasmid

Nanoparticles comprising Derivative 1 and a DNA plasmid were prepared by the FHS technique as follows:

10 mg of Derivative 1 was prepared by dissolving it in 1 ml chloroform in a 50 ml round-bottom flask. The solvent was removed under reduced pressure and the thin film so obtained was dried overnight in a vacuum desiccator to remove traces of solvent. To this dried film, 1 ml of phosphate-buffered saline containing 0.1 mg of the BGFP-N1 reporter gene encoding a red-shift variant of the wild-type green fluorescent protein (GFP) was added. The mixture was then sonicated to form nanoparticles encapsulating the DNA.

Biological Section

Materials

Mice. Eight weeks old male ICR mice, weighing between 25-30 g, were maintained on a standard mice chow and tap water ad lib. The mice were kept in a 12 hours light/dark cycles with temperature of 25±3° C. All animals were handled and tested according to an approved protocol (# IL-24-04-2008).

Cells. COS-7 cells, used as target cells for transfection, were grown in 96-well plates or in 30-mm petri dishes to 40-50% confluence.

Methods i. Transfection. Transfection with DEAE-dextran was used both as a positive control and as a reference method. Transfection efficiency was determined by counting the number of transfected cells (green fluorescent cells) per total number of cells seen in the same field by a fluorescent microscope.

ii. Determination of Analgesic Effect (Hot Plate Test)

The response of mice to a transient painful stimulus was measured following administration of the test material (either i.v. into the tail vein or per os by gavages). The analgesic effect was determined by placing the mouse on a hot plate (55° C., IITC model 39) and recording the time for withdrawing/licking the hind limb (hot plate test). To prevent tissue damage and suffering of the animal, the experiment was terminated after 20 sec if no response was evoked. The response latencies were recorded and either used by themselves for comparison or normalized as percent of maximal possible effect (MPE) using the equation:

$$\% \; MPE = \frac{(RT - RT_0)}{(RT_{max} - RT_0)} \cdot 100$$

where: RT—is the response latency after treatment; $RT_0$—is the response latency of a mouse without treatment and $RT_{max}$—is the maximal response time allowed (20 sec).

iii. Tissue Distribution of Carboxyfluorescein (CF)

For tissue distribution of CF, tissue specimens dissected out from mice that were sacrificed 30 min after injection of nanoparticles loaded with CF, were weighed and homogenized in PBS at a dilution of 1:4 (w/w tissue to PBS). TCA (10%) was added to the homogenates at a ratio of 1:1 to achieve a final concentration of 5% TCA. The specimens were transferred to Eppendorf tubes and centrifuged for 5 minutes at 13,200 rpm. NaOH was added to neutralize the acid (the volume of the NaOH was predetermined by titrating 5% TCA until a pH 7.0 was obtained). The supernatants were used for the fluorimetric determinations at an excitation wavelength of 492 nm, using the scan program.

iv. Brain Uptake of Fluorescein Isothiocyanate (FITC)-Albumin

The amount of FITC-albumin in the brain was measured using the method for assessing the distribution of CF.

Example 20

Analgesic Effect in Mice Treated with Nanoparticles Comprising Leu-Enkephalin

Derivative 4-nanoparticles comprising leu-enkephalin, prepared as described in Example 9 by FHS (film hydration flowed by sonication), were administered to mice and their ability to exert an analgesic effect was measured by the hot plate test described in Methods.

Nanoparticles were made from 10 mg/ml Derivative 4 with cholesterol and cholesteryl hemisuccinate as additives (2:1:1) and 10% molar ratio chitosan (CS)-vemolic acid conjugate in presence of 2.5 mg/ml leu-enkephalin. In these nanoparticles, CS-vemolic acid conjugate serves as a pendant on the nanoparticles/vesicles in order to enhance penetrability.

Nanoparticles were injected into the tail vein at a dose of 20 mg/kg bolaamphiphile, which corresponds to 5 mg/kg leu-enkephaime. Empty nanoparticles and free leu-enkephalin injected in a dose of 20 mg/kg, were used as a negative control and morphine at a dose of 5 mg/kg was used as a positive control. Mice were pretreated with 0.5 mg/kg pyridostigmine 15 min prior to the injection of the nanoparticles. Pyridostigmine inhibits the activity of acetylcholine esterase and thus prevents hydrolysis of the acetyl choline headgroups in the periphery. The drug does not penetrate into the CNS and cannot prevent hydrolysis of the acetylcholine headgroups in the CNS. By itself, pyridostigmine does not evoke an analgesic response.

The results shown on FIG. 1 represent the effect as percent of the maximal possible effect (MPE).

As shown in FIG. 1, nanoparticles comprising leu-enkephalin induced a response which was 3 to 8 times greater than free enkephalin (depending on the time after injection), and approached the efficacy of morphine 30 min after injection. At 60 and 90 minutes, encapsulated leu-enkephalin was more efficient than morphine.

Empty nanoparticles without leu-enkephalin had no effect beyond the control. When the nanoparticles with leu-enkephalin were checked without a pre-injection of pyridostigmine they were about 3 to 7 times less effective than with pre-injection of pyridostigmine (not shown).

Example 21

Analgesic Effect in Mice i.v. Treated with Nanoparticles Comprising Leu-Enkephalin Analgesic effect studies (hot plate test) in mice were carried out using nanoparticles comprising Derivative 1 or Derivative 4 and prepare by the ethanol injection technique described in Example 10. The hot plate test was preformed as described in Example 19. All mice treated with encapsulated leu-enkephalin, were pre-injected with the periphery acetylcholine esterase inhibitor pyridostigmine (0.5 mg/kg).

The response time (in seconds) was checked 10, 30 and 60 minutes after injection and showed for free leu-enkephalin a response time of 3, 2 and 2 sec respectively, while the formulation with leu-enkephalin in nanoparticles of Derivative 1 showed a response time of 5, 5 and 5 sec respectively, and the formulation of leu-enkephalin encapsulated in Derivative 4-nanoparticles showed a response time of 11, 13 and 6 sec respectively. The results demonstrate that leu-enkephalin encapsulated in Derivative 4 nanoparticles had a significant analgesic effect compared to non-encapsulated leu enkephalin. These results also show that the efficacy of nanoparticles comprising Derivative 4 prepared by the ethanol injection technique to deliver enkephalin into the CNS is the same as that of corresponding nanoparticles prepared by the thin film technique. In addition, nanoparticles comprising Derivative 1 are clearly less efficient than those comprising Derivative 4, but still more efficient compared to non-encapsulated enkephalin.

Example 22

Analgesic Effect in Mice Orally Treated with Nanoparticles Comprising Leu-Enkephalin The efficacy of delivering leu-enkephalin in various nanoparticles in oral formulations versus i.v. injectable formulations were tested (a hot plate test of Example 20). Thus, formulations comprising leu-enkephalin encapsulated in the following nanoparticles were prepared: (a) nanoparticles comprising Derivative 4, cholesterol, cholesteryl hemisuccinate and vemolyl-chitosan prepared according to Example 13(i); (b) nanoparticles comprising distearyl phosphatidyl choline (DSPC) as the amphiphilic compound, cholesterol, prepared as described in Example 13 (iii).

Figure 2:
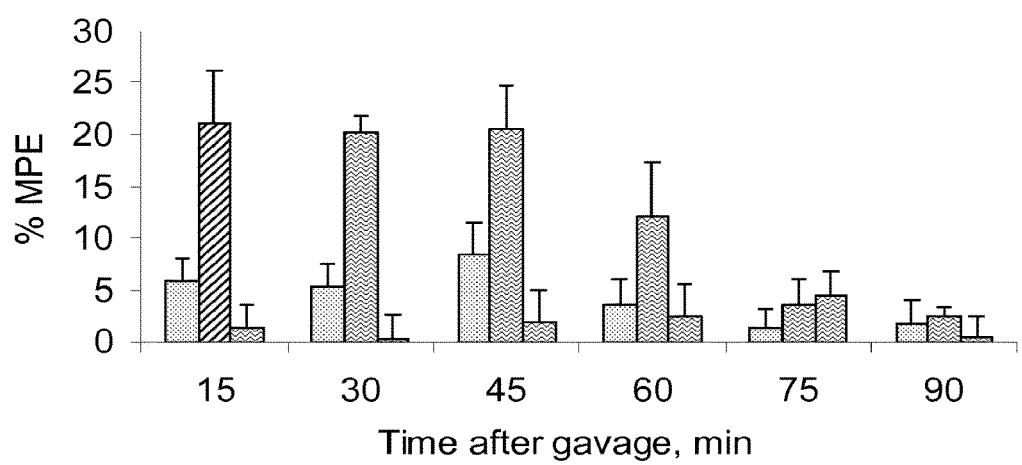
FIG. 2 is a graph showing the analgesic effect as percent of the maximal possible effect (MPE) in a hot plate test conducted on mice treated with free leu-enkephalin (25 mg/kg) (dotted column), Derivative 4-nanoparticles loaded with 25 mg/kg leu-enkephalin (Hatched column), and DSPC liposomes loaded with leu-enkephalin (50 mg/kg) (waves). The values are means±SEM of 5 mice.

Formulations comprising free leu-enkephalin loaded nanoparticles were administered by gavages at a dose of 100 mg/kg bolaamphiphile, which corresponds to 25 mg/kg leu-enkephalin. The same dose of free leu-enkephalin was administered by gavages as a control. The results were compared to liposomes made from 20 mg/ml DSPC in presence of 5 mg/ml leu-enkephalin and administered at a dose of 200 mg/kg phospholipid, which corresponds to 50 mg/kg leu-enkephalin. The mice were preinjected with pyridostigmine as in example 20. The results, are shown in FIG. 2, represent the analgesic effect as percent of maximal possible response (MPE).

The results show that formulations of leu-enkephalin encapsulated in Derivative 4-nanoparticles showed a significantly stronger effect than free enkephalin by a factor of more than 3. The analgesic effect of the oral DSPC liposome was similar to the control of three leu-enkephalin and two to three times less than the Derivative 4-nanoparticles.

Example 23

Brain Uptake of Carboxyfluorescein Delivered in Nanoparticles Comprising Derivative 4 and $PEG_{2000}$-Vernonia Derivatives The ability of nanoparticles of the invention to penetrate into the brain tissue was assessed by using the fluorescent marker CF encapsulated in nanoparticles comprising the bolaamphiphile Derivative 4, a $PEG_{2000}$-vernonia derivative (PEG(202)) and the additives cholesteryl hemisuccinate. The nanoparticles were prepared as described in Example 16.

Two group of mice (2 mice in each) were pre-injected with pyridostigmine (0.5 mg/kg), and then treated as follows: group (i) was i.v. injected with free (non-encapsulated) CF (0.333 mg/Kg); group (ii) was i.v. injected with a formulation containing Derivative 4/cholesterol/cholesteryl hemisuccinate/PEG(202) nanoparticles (10 mg/kg) loaded with CF (0.333 mg/Kg). Brain uptake was determined after 30 minutes as described in Method, and the results are shown in FIG. 3.

Figure 3:
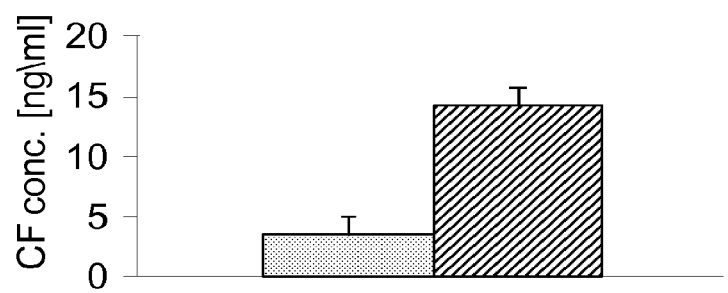
FIG. 3 is a graph showing the brain uptake of carboxy-fluorescein delivered in nanoparticles comprising Derivative 4 and $PEG_{2000}$-vernonia derivatives. Dotted column: free CF(0.333 mg/Kg), column with waves: formulation containing Derivative 4/cholesterol/cholesteryl hemisuccinate/PEG (202) nanoparticles (10 mg/kg) loaded with CF (0.333 mg/Kg).

As seen in FIG. 3, the formulation containing nanoparticles comprising PEG(202) as pedant or additive was taken up by the brain 6 time more than free CF, and twice as much as the formulation containing nanoparticles comprising the ester derivative PEG(201) as pendant (this last comparison is not shown in FIG. 3). This experiment shows that by using the nanoparticles of the invention, low molecular compounds which do not normally enter or distribute into certain organs may nevertheless be delivered to such organs. This demonstrates the potential of the present invention as a delivery system for non polymeric/macromolecular materials Example 24

Brain Uptake of Ovalbumin Delivered in Nanoparticles Comprising Derivative 4

Nanoparticles comprising FITC-albumin prepared as described in Example 17 are administered to mice and their ability to be taken up by the brain was measured.

Two groups of mice (3 mice in each) are treated as follows: group (i) is i.v. injected with free (non-encapsulated) FITC-albumin (30 mg/Kg); group (ii) is i.v. injected with a formulation containing Derivative 4/cholesterol/cholesteryl hemisuccinate nanoparticles (10 mg/kg) loaded with ovalbumin (30 mg/Kg). The mice are sacrificed after 30 minutes and brain uptake is determined, by well known flouremetric techniques for FITC conjugates (see Methods section).

The results are expected to show a significantly greater uptake in the brain of the encapsulated oval albumin as compared to the free oval albumin.

Example 25

Brain Uptake of $^{125}$I-GDNF Delivered in Nanoparticles Comprising Derivative 4

Nanoparticles comprising $^{125}$I-GDNF prepared as described in Example 18 are administered to mice and their ability to be taken up by the brain is measured.

Two groups of mice (3 mice in each) are treated as follows: group (i) is i.v. injected with free (non-encapsulated) $^{125}$I-GDNF (10 mg/Kg); group (ii) is i.v. injected with a formulation containing Derivative 4/cholesterol/cholesteryl hemisuccinate nanoparticles (10 mg/kg) loaded with ovalbumin (10 mg/Kg). The mice are sacrificed after 30 minutes and brain uptake is determined as for CF (see Methods).

The results are expected to show a significantly greater uptake in the brain of the encapsulated $^{125}$I-GDNF as compared to the free $^{125}$I-GDNF.

Example 26

Biodistribution of Carboxyfluorescein Delivered in Nano-Sized Particles

The organ distribution following i.v. injection or oral administration of CF encapsulated in Derivative 4/cholesterol/cholesteryl hemisuccinate nanoparticles, herein also referred to as "basic nanoparticles" was determined and compared to biodistribution of CF encapsulated in Derivative 4/cholesterol/cholesteryl hemisuccinate/vernolyl-chitosan nanoparticles, herein also referred to as "chitosan-nanoparticles" (prepared according to Example 12(ii)). Biodistribution of encapsulated CF was further assessed relative to i.v. or oral administration of free CF.

For biodistribution study following i.v. injection of free and encapsulated CF, three groups of mice (5-7 mice per group) were treated as follows: group (i) was i.v. injected with a formulation containing the basic nanoparticles (10 mg/kg) loaded with 0.2 mg/ml CF; group (ii) was i.v. injected with a formulation containing the chitosan-nanoparticles (10 mg/kg) loaded with 0.2 mg/ml CF; group (iii) was pre-injected with the cholinesterase inhibitor pyridostigmine (0.5 mg/kg) and then i.v. injected with chitosan-nanoparticles loaded with 0.2 mg/ml CF.

Mice were sacrificed 30 minutes after i.v. administration and their brain, lungs, kidneys, muscle, heart and liver were dissected out. The organs were then homogenized, diluted, deproteinated with trichloroacetic acid (TCA), brought to basic pH, and fluorescence intensity was measured. The results are shown in FIGS. 4A-4D.

Figure 4A:
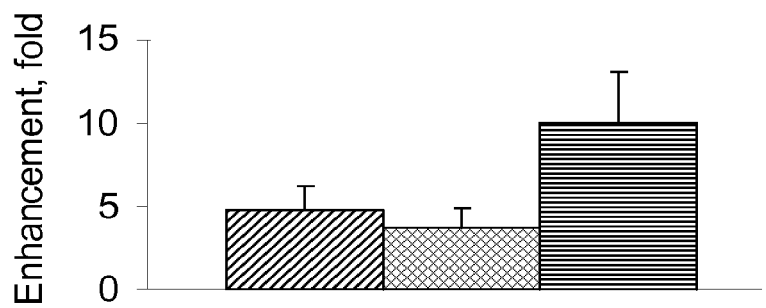
FIGS. 4A-4D are graphs showing the distribution of i.v. administered carboxyfluorescein in the brain (4A), heart (4B), lungs (4C) and kidneys (4D). Hatched: mice injected with a formulation containing the basic nanoparticles (10 mg/kg) loaded with 0.2 mg/ml CF; grid: mice were i.v. injected with a formulation containing chitosan-nanoparticles (10 mg/kg) loaded with 0.2 mg/ml CF pre-injected with pyridostigmine (0.5 mg/kg); and horizontal lines: mice i.v. injected with a formulation containing chitosan-nanoparticles loaded with CF without pre-injected of pyridostigmine.
Figure 4B:
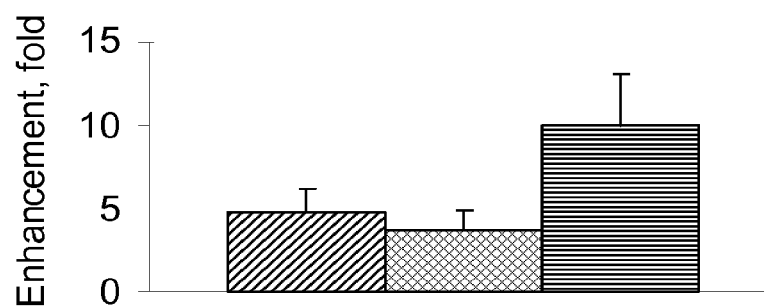
Figure 4C:
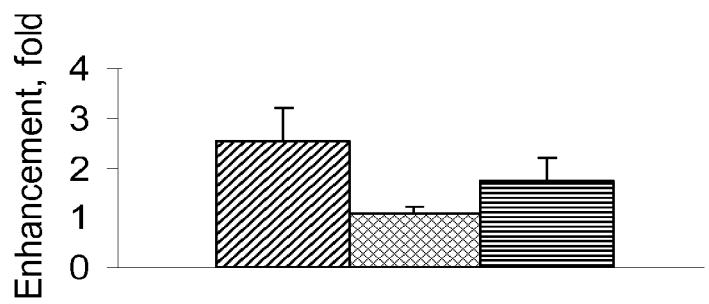
Figure 4D:
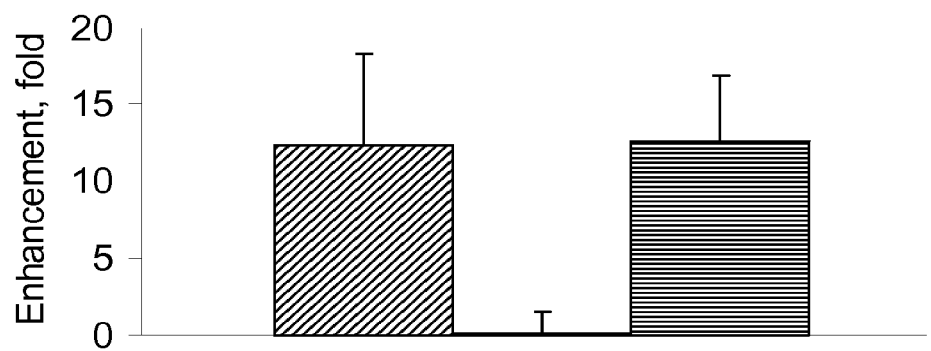
Figure 5A:
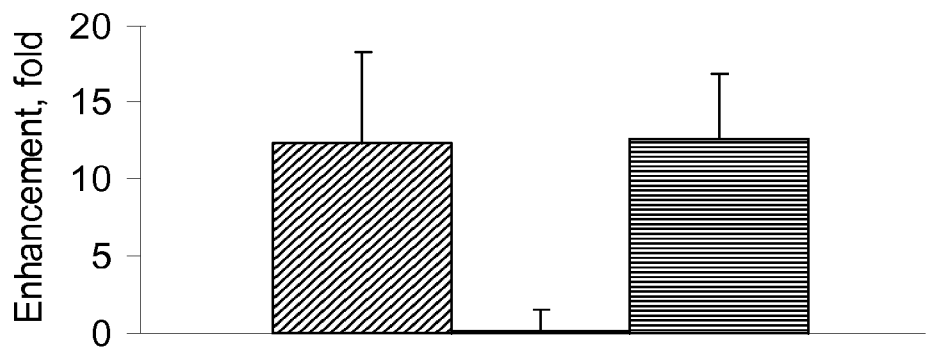
FIGS. 5A-5D are graphs showing the distribution of orally administered carboxyfluorescein in the brain (5A), heart (5B), lungs (5C) and kidneys (5D). Hatched: mice gavaged with a formulation containing the basic nanoparticles (10 mg/kg) loaded with 0.2 mg/ml CF; grid: mice were gavaged with a formulation containing chitosan-nanoparticles (10 mg/kg) loaded with 0.2 mg/ml CF pre-injected with pyridostigmine (0.5 mg/kg); and horizontal lines: mice gavaged with a formulation containing chitosan-nanoparticles loaded with CF without administration of pyridostigmine.
Figure 5B:
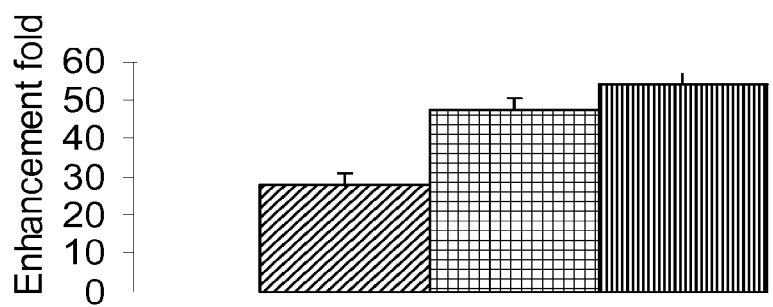
Figure 5C:
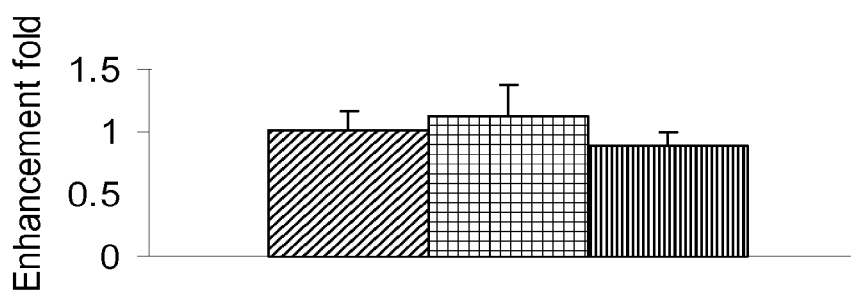
Figure 5D:
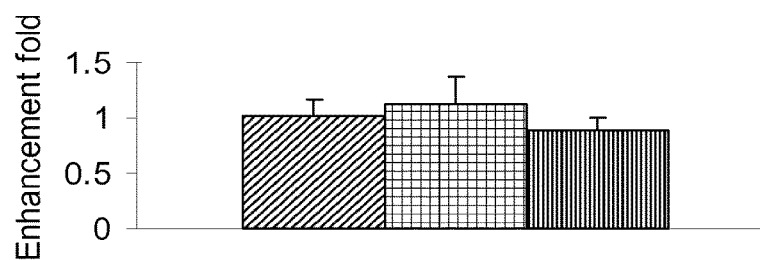

As shown in FIG. 4A, enhanced uptake of CF delivered in chitosan-nanoparticles in mice pre-treated with pyridostigmine (group (iii)) was detected in the targeted organ the brain and also in organs which contain high levels of AChE enzyme, namely, heart (FIG. 4B) and muscle (FIG. 4D). In the lungs (which also served used as a control) the level of CF remained low (FIG. 4C).

The selective uptake by the brain, heart and muscles following i.v. administration proves that these and similar nanoparticles can be used for delivery of therapeutic and preventive agents to these organs, particularly the brain. The active agents may be peptides, proteins, polynucleotides and non polymeric compounds, such as antibacterial agents or agents that control bacterial growth and spreading.

In order to asses the organ distribution of orally administered free and encapsulated CF, three groups of mice (5-7 mice per group) were treated as follows: group (i) was gavaged (force-fed) with a formulation containing basic nanoparticles (10 mg/kg) loaded with 0.2 mg/ml CF; group (ii) was gavaged with a formulation containing chitosan-nanoparticles (10 mg/kg) loaded with 0.2 mg/ml CF; and group (iii) was pre-treated with pyridostigmine (0.5 mg/kg)) and then gavaged with chitosan-nanoparticles loaded with 0.2 mg/ml CF.

Mice were sacrificed 30 minutes after oral administration and their brain, lungs, kidneys, muscle, heart and liver were dissected and analyzed as described above. The results are shown in FIGS. 5A-5D.

Example 27

Analgesic Effect in Mice Treated with Nanoparticles Comprising Various Concentrations of Leu-Enkephalin In order to assess an optimized delivery and targeted release efficiencies, the analgesic effect of formulations containing nanoparticles comprising Derivative 4, cholesterol, cholesteryl hemisuccinate and vernoyl chitosan as additives (chitosan nanoparticles), and various amounts of leu-enkephalin was studied by the hot plate test. Nanoparticles were prepared as described in Example 15.

Figure 6:
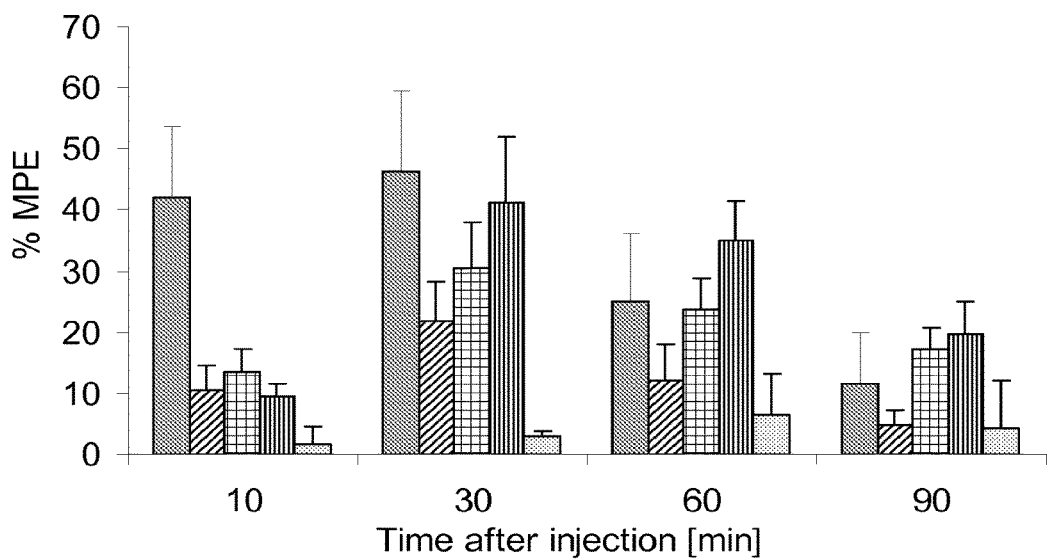
FIG. 6 is a graph showing the analgesic effect as percent of the maximal possible effect (MPE) in a hot plate test conducted on mice treated with various concentrations of leu-enkephalin. Gray: mice treated with morphine (5 mg/kg); hatched: mice treated with Derivative 4-nanoparticles loaded with 20 mg/kg leu-enkephaime; grids: mice treated with Derivative 4-nanoparticles loaded with 10 mg/kg leu-enkephaime; lines: mice treated with Derivative 4-nanoparticles loaded with 5 mg/kg leu-enkephaime; and dotted: mice treated with free leu-enkephalin (20 mg/kg). The values are means±SEM of 5 mice.

Five groups of mice (5 mice in each group) were treated as follows: group (i) i.v. administration of morphine (5 mg/kg). This groups served as the positive control; group (ii) i.v. administration of chitosan nanoparticles (20 mg/kg) loaded with 20 mg/kg leu-enkephalin; group (iii) i.v. administration of chitosan nanoparticles (20 mg/kg) loaded with 10 mg/kg leu-enkephalin; group (iv) i.v. administration of chitosan nanoparticles (20 mg/kg) loaded with 5 mg/kg leu-enkephalin; group and group (v) i.v. injection of free (nonencapsulated) leu-enkephalin (20 mg/Kg). Four mice were checked for each time point (10, 30, 60 and 90 min) after i.v. administration. The mice in group (ii)-(vi) where pre-injected with pyridostigmine in PBS at a concentration of 0.5 mg/kg. Mice before i.v. treatment served as control and as zero point. The hot plate test was conducted as described in Example 19. The results for groups (i)-(iv) and (vi) are shown in FIG. 6.

The results show a greater analgesic effect at lower concentration of enkephalin, 30 and 60 min after administration. Without being bound to a particular theory, the lower quantity of enkephalin in the nanoparticles may give rise to more stable nanoparticles, probably of smaller size, having improved penetrability and/or improved surface properties. Free leu-enkephalin and empty nanoparticles injected to mice pretreated with pyridostigmine had no significant analgesic effect.

These results indicate that the chitosan nanoparticle penetrated the BBB and released the encapsulated leu-enkephalin within the brain. These results also demonstrate that optimization of delivery can be assessed by conventional optimization procedures.

Example 28

Analgesic Effect in Mice Treated with Nanoparticles Comprising Derivative 1 and Derivative 4

In order to optimize delivery efficiency, active agent targeted release efficiency, stability and durability in the blood stream, nanoparticles comprising a mixture of Derivative 1 and Derivative 4 in a weight ratio of 2:1, respectively, and the additives cholesteryl hemisuccinate, cholesterol and vernoyl chitosan were prepared and loaded with enkephalin as described in Example 13(ii). These nanoparticles, also termed herein "Derivative 1+Derivative 4 nanoparticles" were i.v. injected to mice and the analgesic effect of encapsulated versus free active agent was assessed by the hot plate test described in Example 20. For comparison, analgesic effect of leu-enkephalin encapsulated in cation liposomes prepared from dioleoyl trimethylammonium propane (DOTAP) and cholesterol was measured. These liposomes were prepared as described in Methods.

Figure 7:
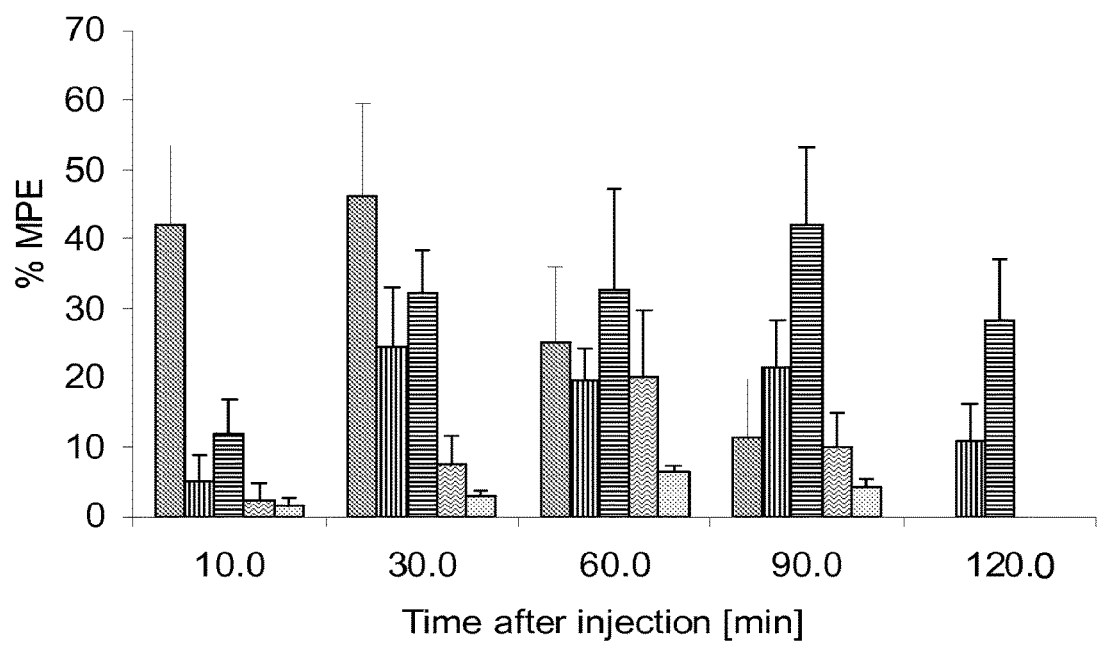
FIG. 7 is a graph showing the analgesic effect as percent of the maximal possible effect (MPE) in a hot plate test conducted on mice treated leu-enkephalin delivered in various nanoparticles. Gray: mice treated with morphine (5 mg/kg); lines: mice i.v. injected with Derivative 1+Derivative 4 nanoparticles (20 mg/kg) loaded with 5 mg/kg leu-enkephalin; group; horizontal lines: mice pre-injected with pyridostigmine and then i.v. injected with Derivative 1+Derivative 4 nanoparticles (20 mg/kg) loaded with 5 mg/kg leu-enkephalin; group; dotted: mice treated with free leu-enkephalin (20 mg/kg). The values are means±SEM of 5 mice.

Five groups of mice (5 mice in each group) were treated as follows: group (i) i.v. administration of morphine (5 mg/kg). This groups served as the positive control; group (ii) i.v. administration of Derivative 1+Derivative 4 nanoparticles (20 mg/kg) loaded with 5 mg/kg leu-enkephalin; group (iii) pre-injected with pyridostigmine in PBS at a concentration of 0.5 mg/kg and then i.v. administration of Derivative 1+Derivative 4 nanoparticles (20 mg/kg) loaded with 5 mg/kg leu-enkephalin; group (iv) i.v. administration of DOTAP liposomes (20 mg/kg) loaded with 5 mg/kg leu-enkephalin; group (v) i.v. injection of free (non-encapsulated) leu-enkephalin (20 mg/Kg). Four mice were checked for each time point (10, 30, 60, 90 and 120 min) after i.v. administration. Mice before i.v. treatment served as control and as zero point. The results are shown in FIG. 7.

The results clearly demonstrate that nanoparticles comprising a mixture of the two related bolaamphiphiles Derivative 1 and Derivative 2, significantly increased the duration of the analgesic affect beyond 60 min as compared to nanoparticle comprising only one bolaamphiphile, Derivative 4 (chitosan nanoparticles) described in Example 26. As shown in FIG. 10, at 90 and 120 after administration, the % MPE for the Derivative 1+Derivative 4 nanoparticles with pre-injection of pyridostigmine (group (iii)) was about 42 and 38, respectively, whereas for the chitosan nanoparticles the % MPE at 90 min was 20 (see FIG. 7. On the other hand, at 30 min, the chitosan nanoparticles of Example 27 had a higher analgesic effect compared to Derivative 1+Derivative 4 nanoparticles.

In addition, the Derivative 1+Derivative 4 nanoparticles provided a significant analgesic effect even without pre-injection of pyridostigmine. The Derivative 1+Derivative 4 nanoparticles had better drug delivery characteristics than cationic liposomes. As expected, free enkephalin had no significant analgesic effect.

Thus by using nanoparticles comprising one type of bolaamphiphile bearing head groups which are more readily hydrolyzed at the target site may provide a strong effect in the short term of 10-30 min, while longer term effects may be achieved with nanoparticle comprising a mixture of bolaamphiphiles bearing head groups which are hydrolyzed at different times.

This example shows that by combining different bolaamphiphiles, the delivery and release of active agents such as peptides proteins and polynucleotides can be optimized.

Example 29

Transfection of Cells with DNA Encapsulated in Nanoparticles

The transfection of a polynucleotide delivered by nanoparticle comprising Derivative 1 was assessed.

Nanoparticles comprising Derivative 1 and a BGFP-N1 reporter gene encoding a red-shift variant of the wild-type green fluorescent protein (GFP were prepared according to Example 19 and added to COS-7 cells that were grown in 96-well plates or in 30-mm petri dishes to 40-50% confluence. Transfection with DEAE-dextran was used both as a positive control and as a reference method. Transfection efficiency was determined by counting the number of transfected cells (green fluorescent cells) per total number of cells seen in the same field by a fluorescent microscope.

The transfection efficiency was dependent on the concentration of the amphiphilic derivative used for the vesicle formation. When the concentration of the amphiphilic derivative was increased from 5 to 10 mg/ml, the transfection efficiency was almost doubled that of the DEAE-dextran. The higher transfection efficiency with nanoparticles was also expressed in terms of the amount of cDNA needed for transfection, i.e., with vesicles less cDNA yielded more transfected cells than did a larger amount of cDNA complexed with DEAE-dextran This example clearly demonstrates the high potential of the nanoparticles of the invention to enhance transfection of polynucleotides such as DNA and RNA.

Scheme 1

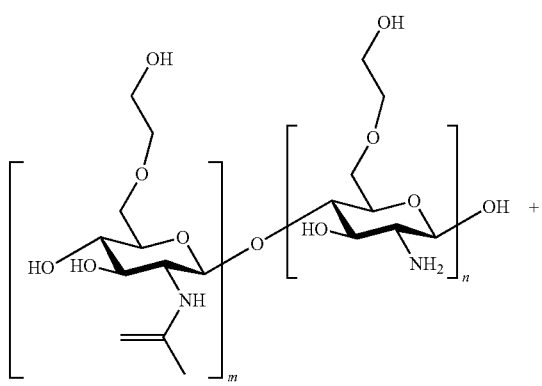

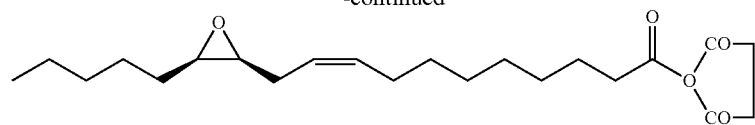
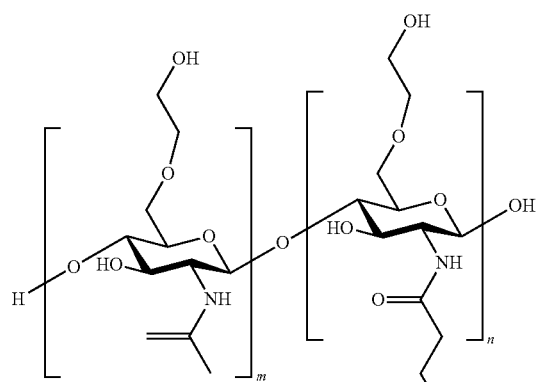
50
Scheme 2
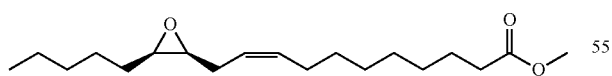
55
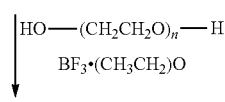
60
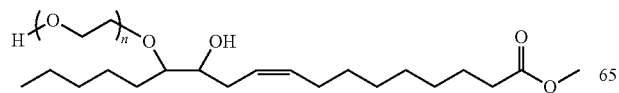
65

Scheme 3
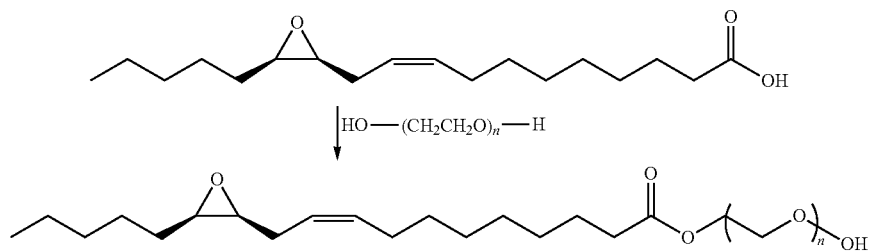
Scheme 4
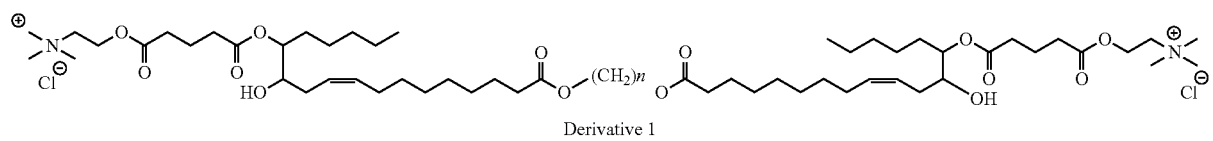
Derivative 1
Scheme 5
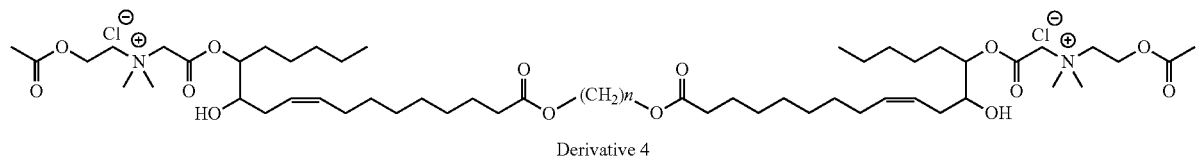
Derivative 4

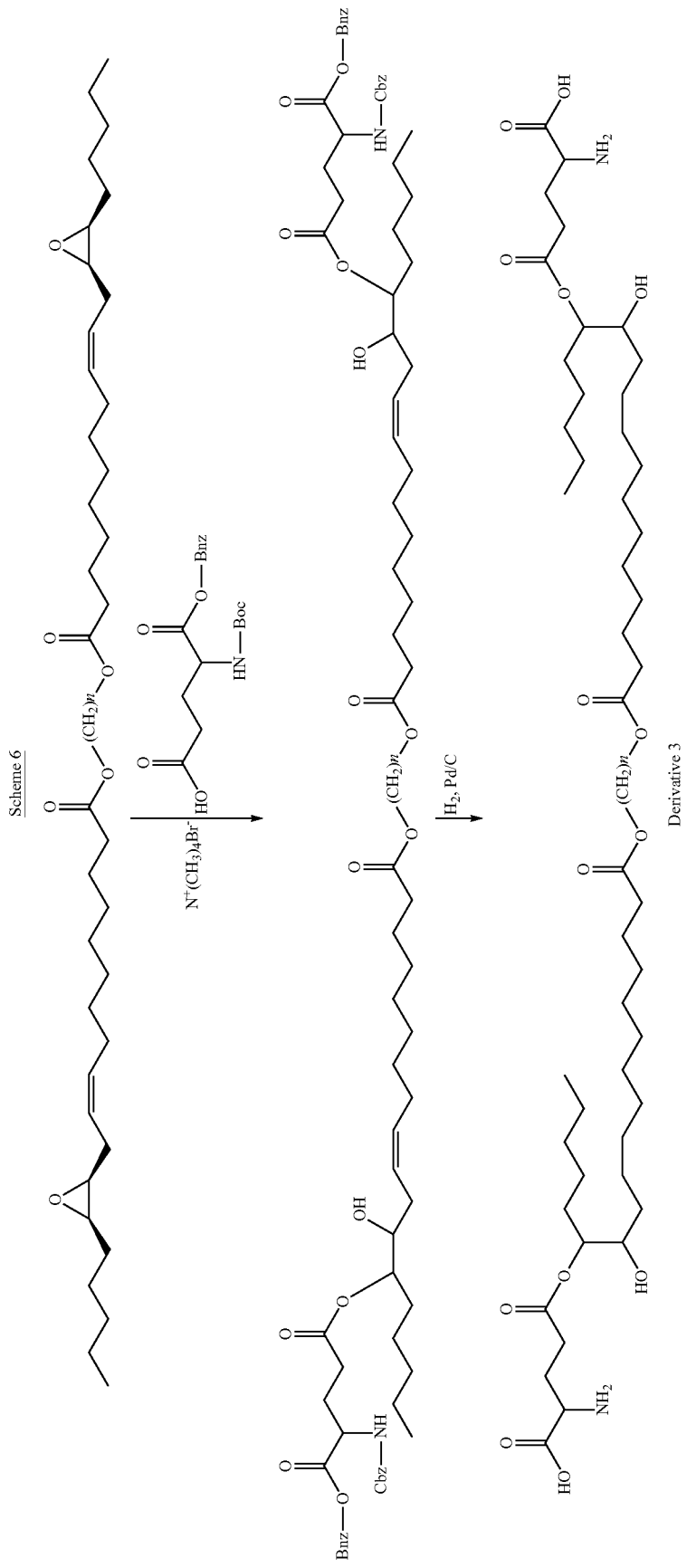

REFERENCES

Danoff, E J. X Wang, S H Tung, N A. Sinkov, A M. Kemrne, S R. Raghavan, and D S. English Surfactant vesicles for high-efficiency capture and separation of charged organic solutes Langmuir, 2007, 23(17): 8965-71

Grinberg S, Kolot V, Linder C, Shaubi E, Kas'yanov V, Deckelbaum R J, Heldman E. Synthesis of novel cationic bolaamphiphiles from vernonia oil and their aggregated structures. Chem Phys Lipids, 2008, Feb. 12

Wang, X.: Danoff, E. J.: Sinkov, N. A.: Lee, J.-H.: Raghavan. S. R.: English, D. S. Lcmgrmiir 2006, 22, 6461

Y. Lapidot, S. Rappaport, Y. Wolman, *J. Lipid Res.* 8, Use of esters of N-hydroxysuccinimide in the synthesis of N-acylaminoacids, 1967, 142-145

Y. Wu, Y. Zheng, W. Yang, C. Wang, Y. Hu, S. Fu) Carbohydrate Polymers, 59, Synthesis and characterization of a novel amphiphilic chitosan-polylactide graft copolymer 2005, 165-171

The invention claimed is:

1. A nano-sized particle comprising at least one multi-headed amphiphilic compound, in which at least one head-group of said multi-headed amphiphilic compound is selectively cleavable or contains a selectively cleavable group, and at least one biologically active agent, which is both encapsulated within the nano-particle and non-covalently associated thereto, wherein at least one amphiphilic compound is Derivative 4

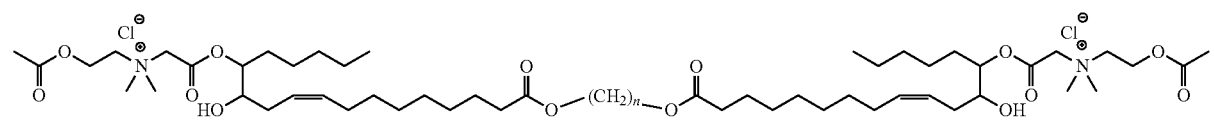

further comprising at least one of Derivatives 1, 2, 3, 5, 6, 7, 8, 9, or 10 wherein the derivatives are

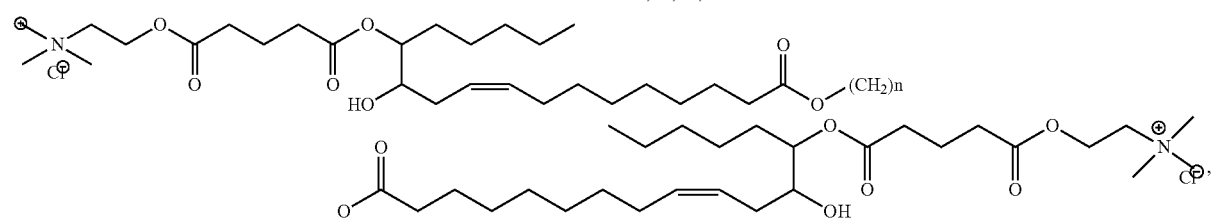

Derivative 1

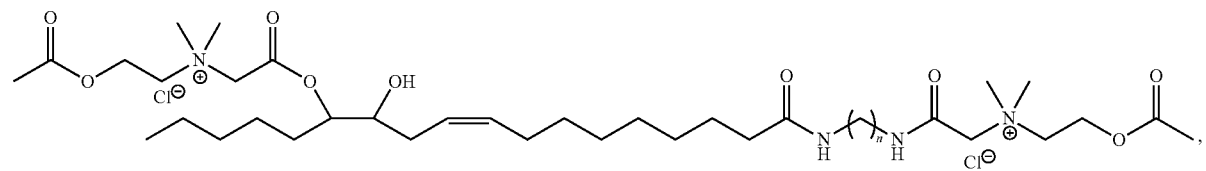

n = 12
Derivative 2

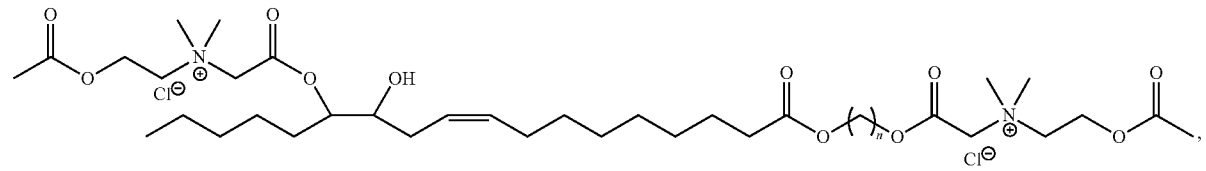

n = 10
Derivative 3

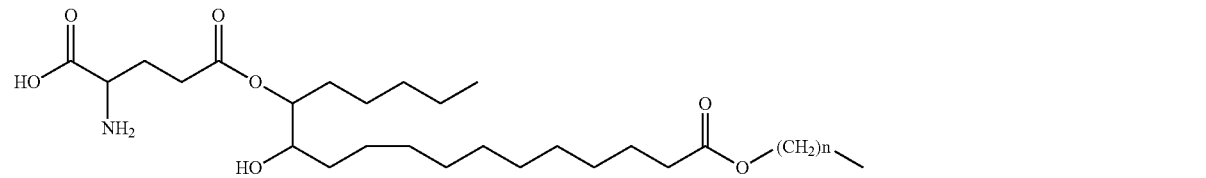

Derivative 5

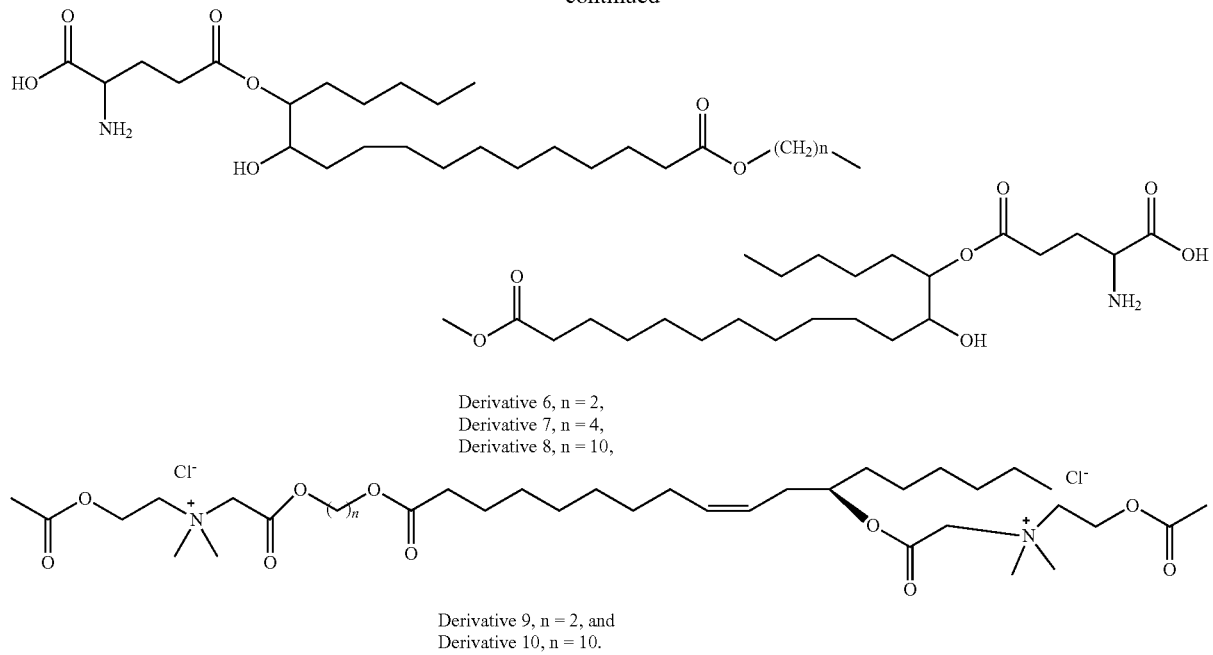

Derivative 6, n = 2,
Derivative 7, n = 4,
Derivative 8, n = 10,

Derivative 9, n = 2, and
Derivative 10, n = 10.

2. The nano-sized particle of claim 1, wherein the biologically active agent is associated to the nano-particle via non-covalent interactions selected from ionic and polar interactions, electrostatic forces, hydrophobic interactions, VanderWaals forces, or hydrogen bonds.

3. The nano-sized particle of claim 1, wherein the biologically active agent forms a salt complex with the at least one multi-headed amphiphilic compound.

4. The nano-sized particle of claim 1, wherein the biologically active agent is embedded or incorporated in the nano-sized particle matrix.

5. The nano-sized particle of claim 1, wherein the biologically active agent is further ionically associated with the nano-sized particle.

6. The nano-sized particle of claim 1, in the form of a vesicle or liposome formed from said at least one multi-headed amphiphilic compound.

7. The nano-sized particle of claim 6, wherein said vesicle is a monolayer vesicle.

8. The nano-sized particle of claim 6, wherein the biologically active agent is encapsulated within the core of said vesicle and associated via one or more non-covalent interactions to the vesicular membrane on the outer surface and/or the inner surface, optionally as pendant decorating the outer or inner surface, and optionally further incorporated into the vesicular membrane.

9. The nano-sized particle of claim 1, comprising a mixture of at least one multi-headed amphiphile and at least one single-headed amphiphile.

10. The nano-sized particle of claim 1, wherein said at least one multi-headed amphiphile is a bolaamphiphile.

11. The nano-sized particle of claim 1, wherein at least one of the headgroups of said multi-headed amphiphilic compound serve as substrates to enzymes at a target site in a biological environment, enhance transport of the nano-sized particle through biological barriers and/or stabilize the vesicular structure of the nano-sized particle.

12. The nano-sized particle of claim 11, wherein at least one of said headgroups is ionically charged.

13. The nano-sized particle of claim 1, wherein said selectively cleavable headgroup is cleaved under selective conditions selected from chemical, physical, or biological conditions selected from change of pH, change in temperature, oxidative or reducing conditions, and/or enzymatic conditions.

14. The nano-sized particle of claim 13, wherein said selectively cleavable headgroup is cleaved enzymatically in a biological environment by degradative enzymes selected from hydrolases, esterases, phosphatases, oxidases, decarboxylases, deaminases, and isomerases.

15. The nano-sized particle of claim 11, wherein said headgroup is selected from: (i) choline, thiocholine, O-alkyl, N-alkyl, or ester derivatives thereof; (ii) non-aromatic amino acids with functional side chains, or an aromatic amino acid; (iii) a peptide or a peptide derivative that is specifically cleaved by an enzyme at a diseased site selected from enkephalin, N-acetyl-ala-ala, a peptide that constitutes a domain recognized by beta and gamma secretases, and a peptide that is recognized by stromelysins; (iv) saccharides; and (v) other compounds.

16. The nano-sized particle of claim 10, wherein said bolaamphiphile is a symmetric or asymmetric bolaamphiphile optionally containing at least one hydrogen-bonding group selected from —OH, —SH, —NH—, —N+H$_2$—, —NH$_2$, —WH$_3$, —O—CO—NH—, —NH—CO—NH—, —C=NOH, —C(NHz)=NOH, —C(NH$_2$)=NO—, and —CO—NH$_2$, located either within the selectively cleavable headgroup or within the headgroup containing the selectively cleavable group or moiety and/or in close proximity thereto.

17. The nano-sized particle of claim 16, wherein said symmetric or asymmetric bolaamphiphile further contains one or more branching alkyl chains bearing pendants selected from chitosan derivatives, polyamines or certain peptides, which enhance penetration through various biological barriers.

18. The nano-sized particle of claim 16, wherein said bolaamphiphile contains at least one hydrogen-bonding group.

19. The nano-sized particle of claim 16, wherein said bolaamphiphile does not contain a hydrogen-bonding group.

20. The nano-sized particle of claim 1, further comprising at least one additive for targeting purposes, enhancing permeability and/or increasing the stability of the nano-sized particle, wherein said additives are selected from: (i) a single headed amphiphilic derivative comprising one, two, or multiple aliphatic chains, preferably two aliphatic chains linked to a midsection/spacer region and a sole headgroup, optionally a selectively cleavable headgroup or one containing a polar or ionic selectively cleavable group or moiety, attached to the N atom in the middle of said midsection; (ii) cholesterol and cholesterol derivatives; (iii) phospholipids, zwitterionic, acidic, or cationic lipids; (iv) chitosan and chitosan derivatives; (vi) ligands of specific receptors at a target site of a biological environment; (vii) polycationic polymers; (viii) peptides that enhance transport through the BBB; (ix) monosaccharides and derivatives thereof; (x) modified proteins or antibodies that undergo absorptive-mediated or receptor-mediated transcytosis through the blood-brain barrier; (xi) mucoadhesive polymers; and (xii) $Ca^{2+}$ chelators.

21. The nano-sized particle of claim 1, wherein at least one said biologically active agent is selected from: (i) a natural or synthetic peptide or protein; (ii) nucleosides and polynucleotides; (iii) an antiviral or antibacterial; and (iv) antineoplastic or chemotherapy agents.

22. The nano-sized particle of claim 1 having a spherical shape and a diagonal of less than 200 nm.

23. The nano-sized particles of claim 1, further comprising at least one bolaamphiphile selected from Derivative 1, Derivative 2, and Derivative 3, an active agent selected from leu-enkephalin, carboxyfluorescein, $^{125}$I-5 GDNF, and ovalbumin, and at least one additive selected from vemolyl chitosan, Derivative 5, PEG-vernonia conjugate, cholesterol and cholesteryl hemisuccinate.

24. A pharmaceutical composition comprising a nano-sized particle of claim 1 and a pharmaceutically acceptable carrier.

25. A method for the treatment or diagnosis of a disease or disorder selected from: (i) a disease or disorder associated with the CNS; (ii) cancer; (iii) diabetes; (iv) an immunodeficiency disease; and (v) viral and bacterial infections, which comprises administering to an individual in need thereof a nano-sized particle of claim 1.

26. A method for treatment of a disease or disorder selected from: (i) a disease or disorder associated with the CNS; (ii) cancer; (iii) diabetes; (iv) an immunodeficiency disease; and (v) viral and bacterial infections,
which comprises administering to an individual in need thereof a nano-sized particle of claim 1 optionally together with a suitable peripheral enzyme inhibitor to prevent premature disruption of the nano-sized particle.

27. The nano-sized particle of claim 14, wherein the biological environment is the brain or blood and the degradative enzyme is selected from cholinesterase (ChE), acetylcholine esterase (AChE), and L-amino acid decarboxylase (AADC).

28. The nano-sized particle of claim 15, wherein said headgroup is selected from the group consisting of glutamic acid, aspartic acid, lysine, cysteine, tyrosine, tryptophan, phenylalanine, levodopa (3,4-dihydroxy-phenylalanine), p-aminophenylalanine, glucose, mannose, ascorbic acid, nicotine, cytosine, lobeline, polyethylene glycol, a cannabinoid, and folic acid.

29. The nano-sized particle of claim 20 comprising at least one of: cholesteryl hemrnisuccinate, vemolic acid-chitosan conjugate, quatemized chitosan, chitosan-polyethylene glycol (PEG) conjugates, chitosan-polypropylene glycol (PPG) conjugates, chitosan N-conjugated with different amino acids, carboxyalkylated chitosan, sulfonyl chitosan, carbohydrate-branched N-(carboxymethylidene) chitosan, N-(carboxymethyl) chitosan, protamine, polylysine, polyarginine, nicotine, cytisine, lobeline, 1-glutamic acid, MK801, morphine, enkephalins, diazepam (valium), librium, dopamine agonists, dopamine antagonists, tricyclic antidepressants, muscarinic agonists, muscarinic antagonists, cannabinoids, arachidonyl ethanol amide; polyethylene amine, OX 26, transferrins, polybrene, histone, cationic dendrimer, synthetic peptides, polymyxin B nonapeptide (PMBN), glucose and derivatives thereof, mannose and derivatives thereof, ascorbic acid and derivatives thereof, bradykinin B2 agonist RMP-7, monoclonal antibody to the transferrin receptor, glycerides, and steroidal detergents, and, optionally, a midsection/spacer region which is —NH—$(CH_2)_2$—N—$(CH_2)_2$—N—, or —O—$(CH_2)_2$—N—$(CH_2)_2$—O—.

30. The nano-sized particle of claim 21 comprising at least one of: an analgesic, a peptide from the nkephalin class, insulin, insulin analogs, oxytocin, calcitonin, tyrotropin releasing hormone, follicle stimulating hormone, luteinizing hormone, vasopressin, vasopressin analogs, catalase, interleukin-II, interferon, colony stimulating factor, tumor necrosis factor (TNF), melanocyte-stimulating hormone, superoxide dismutase, glial-cell derived neurotrophic factor (GDNF), the Gly-Leu-Phe (GLF) families, small interfering RNA (siRNA), a DNA plasmid, cyclosporin, doxorubicin, epirubicin, bleomycin, cisplatin, carboplatin, vinca alkaloids, vincristine, Podophyllotoxin, Taxol, Docetaxel, irinotecan, or topotecan.

31. The nano-sized particle of claim 22 having a spherical shape and a diagonal of less than 100 nm.

32. A method of claim 25, wherein the disease or disorder is Parkinson's disease, Alzheimer's disease, multiple sclerosis, breast cancer, prostate cancer, or brain tumors.

33. A method of claim 26, wherein the disease or disorder is Parkinson's disease, Alzheimer's disease, multiple sclerosis, breast cancer, and brain tumors.

34. The nano-sized particle of claim 1, further comprising at least one of Derivatives 1, 2, 3, or 5
wherein the derivatives are

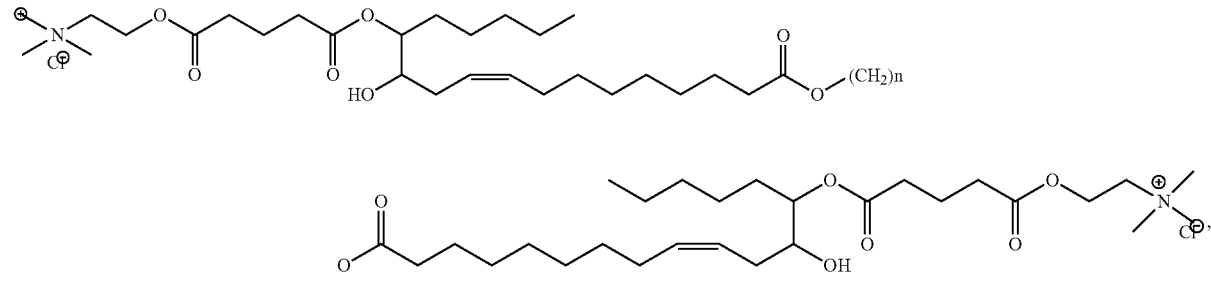

Derivative 1

-continued
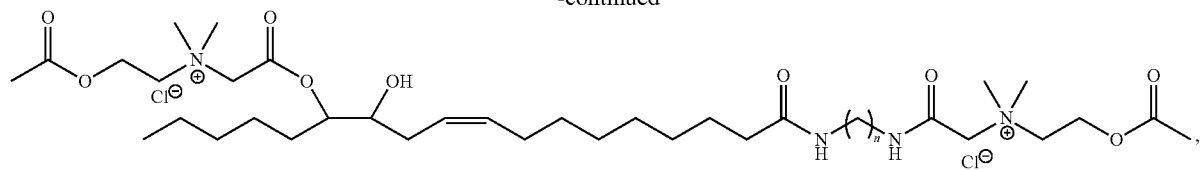
n = 12
Derivative 2
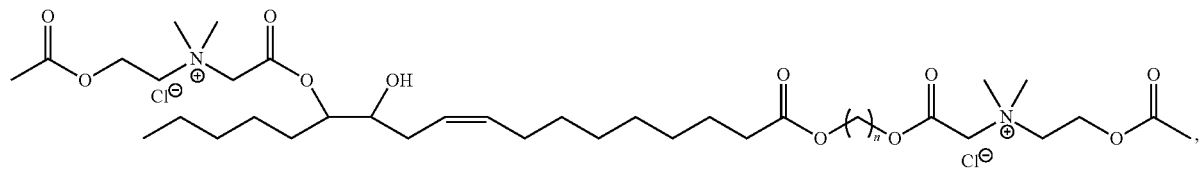
n = 10
Derivative 3
and
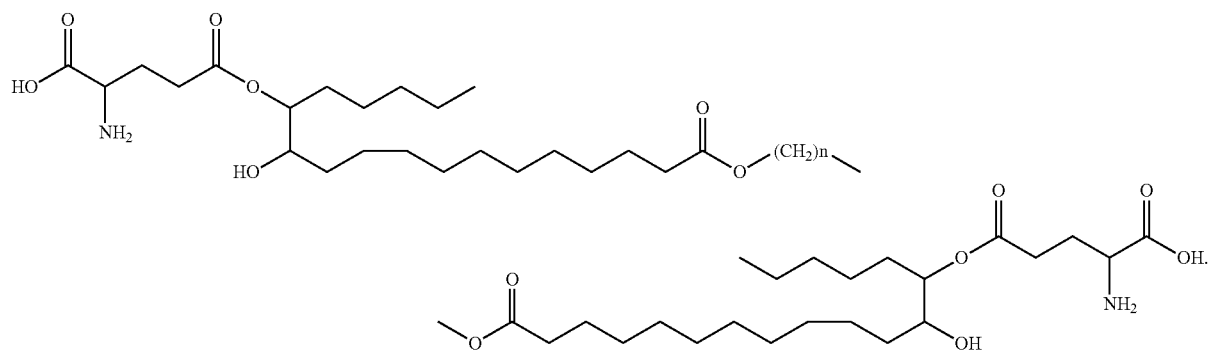
Derivative 5
35. The nano-sized particle of claim 1, further comprising at least one of Derivatives 6, 7, 8, 9, or 10 wherein the derivatives are
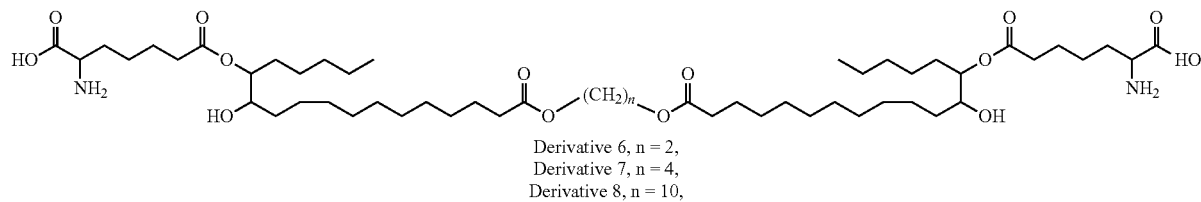
Derivative 6, n = 2,
Derivative 7, n = 4,
Derivative 8, n = 10,
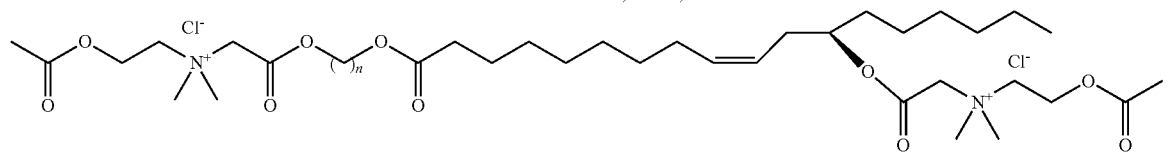
Derivative 9, n = 2, and
Derivative 10, n = 10.
* * * * *